(12) United States Patent
Wang et al.

(10) Patent No.: US 11,471,418 B2
(45) Date of Patent: Oct. 18, 2022

(54) PHARMACEUTICAL COMPOSITIONS OF AMORPHOUS SOLID DISPERSIONS AND METHODS OF PREPARATION THEREOF

(71) Applicant: Shenzhen Pharmacin Co., Ltd., Shenzhen (CN)

(72) Inventors: Zeren Wang, Southbury, CT (US); Shun Chen, Shenzhen (CN); Longwei Sun, Shenzhen (CN); Yanxin Zhao, Shenzhen (CN)

(73) Assignee: Shenzhen Pharmacin Co., Ltd., Shenzhen (CN)

( * ) Notice: Subject to any disclaimer, the term of this patent is extended or adjusted under 35 U.S.C. 154(b) by 0 days.

(21) Appl. No.: 17/097,789

(22) Filed: Nov. 13, 2020

(65) Prior Publication Data
US 2022/0096389 A1     Mar. 31, 2022

(30) Foreign Application Priority Data
Sep. 29, 2020   (CN) .......................... 202011046895.4

(51) Int. Cl.

| A61K 9/48 | (2006.01) |
|---|---|
| A61K 47/12 | (2006.01) |
| A61K 47/32 | (2006.01) |
| A61K 47/02 | (2006.01) |
| A61P 35/00 | (2006.01) |
| A61K 9/14 | (2006.01) |
| A61K 31/519 | (2006.01) |

(52) U.S. Cl.
CPC .............. *A61K 9/4866* (2013.01); *A61K 9/14* (2013.01); *A61K 9/485* (2013.01); *A61K 9/4858* (2013.01); *A61K 31/519* (2013.01); *A61K 47/02* (2013.01); *A61K 47/12* (2013.01); *A61K 47/32* (2013.01); *A61P 35/00* (2018.01)

(58) Field of Classification Search
CPC .......... A61K 9/14; A61K 9/141; A61K 9/145; A61K 9/146; A61K 9/16; A61K 9/1605; A61K 9/1617; A61K 9/1623; A61K 9/1647; A61K 9/1652; A61K 9/167; A61K 9/20; A61K 9/204; A61K 9/2013; A61K 9/2018; A61K 9/2022; A61K 9/2036; A61K 9/2004; A61K 9/205; A61K 9/2054; A61K 9/2833; A61K 9/286; A61K 9/2866
See application file for complete search history.

(56) References Cited

U.S. PATENT DOCUMENTS

| 745,168 | A | 11/1903 | Eastwood |
|---|---|---|---|
| 4,696,745 | A | 9/1987 | Itagaki et al. |
| 4,847,092 | A | 7/1989 | Thakkar et al. |
| 6,087,380 | A | 7/2000 | Hauel et al. |
| 6,936,612 | B2 | 8/2005 | Barvian et al. |
| 7,022,711 | B2 | 4/2006 | Hamby et al. |
| 7,208,489 | B2 | 4/2007 | Barvian et al. |
| 7,345,171 | B2 | 3/2008 | Beylin et al. |
| 7,456,168 | B2 | 11/2008 | Barvian et al. |
| 7,863,278 | B2 | 1/2011 | Beylin et al. |
| 7,866,474 | B2 | 1/2011 | Geser et al. |
| 7,932,273 | B2 | 4/2011 | Schmid et al. |
| 8,557,995 | B2 | 10/2013 | Miller et al. |
| 8,669,257 | B2 | 3/2014 | Liu et al. |
| 9,034,822 | B2 | 5/2015 | Van et al. |
| 9,259,399 | B2 | 2/2016 | Chen-Kiang et al. |
| 9,889,135 | B2 | 2/2018 | Koff et al. |
| 9,925,174 | B2 | 3/2018 | Brauns et al. |
| 10,160,759 | B2 | 12/2018 | Wu et al. |
| 10,258,604 | B2 | 4/2019 | Andreano et al. |
| 10,449,195 | B2 * | 10/2019 | Wang ................... A61K 9/1652 |
| RE47,739 | E | 11/2019 | Barvian et al. |
| 10,813,937 | B2 * | 10/2020 | Wang ...................... A61K 9/146 |
| 10,894,049 | B2 * | 1/2021 | Wang ................... A61K 31/519 |
| 2003/0149001 | A1 | 8/2003 | Barvian et al. |
| 2005/0019399 | A1 | 1/2005 | Fischer et al. |
| 2007/0015802 | A1 | 1/2007 | Lal et al. |
| 2007/0141141 | A1 | 6/2007 | Bateman et al. |
| 2009/0030005 | A1 | 1/2009 | Kamb et al. |
| 2009/0214645 | A1 | 8/2009 | Kramer et al. |
| 2011/0009353 | A1 | 1/2011 | Chen-Kiang et al. |
| 2011/0030662 | A1 | 2/2011 | Zitzler et al. |
| 2011/0306632 | A1 | 12/2011 | Miller et al. |
| 2014/0220112 | A1 | 8/2014 | Szoka, Jr. et al. |

(Continued)

FOREIGN PATENT DOCUMENTS

| CN | 1638771 A | 7/2005 |
|---|---|---|
| CN | 101001857 A | 7/2007 |

(Continued)

OTHER PUBLICATIONS

Beeton, C. et al. Kv1.3 channels are a therapeutic target for T cell-mediated autoimmune diseases. PNAS 103(46):17414-17419 (Nov. 14, 2006).
EP Search Report for EP15875281.6 dated Jul. 9, 2018.
Non-Final Office Action dated Dec. 20, 2019, for U.S. Appl. No. 16/554,103.
Rocca et al. expert opinion on pharmacotherapy, 2013, Taylor & Francis vol. 15(3), pp. 407-420.
Shuangping, Yu et al., Progress in Surface Modification of Superfine Powder, Journal of Guangdong University of Technology, Jun. 30, 2003, pp. 70-76.
Office Action in corresponding Brazilian Patent Application BR112018070198-0 dated Sep. 14, 2021.
Affymetrix GeneChip Human Genome U1 33 Array Set HG-U133A, Geo Expression, Mar. 11, 2002 (XP002361324).

(Continued)

*Primary Examiner* — Micah Paul Young
(74) *Attorney, Agent, or Firm* — Wilson Sonsini Goodrich & Rosati

(57) ABSTRACT

Provided are amorphous solid dispersions comprising an active pharmaceutical ingredient and pharmaceutical compositions comprising the amorphous solid dispersions. Also described herein are methods for preparing and using such compositions. In some embodiments, an amorphous solid dispersion comprises an active pharmaceutical ingredient such as palbociclib or neratinib, one or more acids, and a high-molecular weight material.

21 Claims, 21 Drawing Sheets

(56) References Cited

U.S. PATENT DOCUMENTS

| | | | |
|---|---|---|---|
| 2014/0309250 A1 | 10/2014 | Verma et al. | |
| 2015/0099737 A1 | 4/2015 | Brain et al. | |
| 2015/0111896 A1 | 4/2015 | Sharpless et al. | |
| 2015/0140036 A1 | 5/2015 | Mannick et al. | |
| 2015/0273070 A1 | 10/2015 | Li et al. | |
| 2016/0310482 A1 | 10/2016 | Haber et al. | |
| 2017/0281631 A1* | 10/2017 | Wang | A61K 9/4808 |
| 2018/0098963 A1 | 4/2018 | Andreano et al. | |
| 2018/0207100 A1* | 7/2018 | Ibrahim | A61K 9/28 |
| 2018/0280392 A1 | 10/2018 | Zeng et al. | |
| 2019/0046533 A1 | 2/2019 | Chen et al. | |
| 2019/0091227 A1 | 3/2019 | Czibere et al. | |
| 2019/0120844 A1 | 4/2019 | Lou et al. | |
| 2019/0231718 A1 | 8/2019 | Andreano et al. | |
| 2019/0292605 A1 | 9/2019 | Slamon et al. | |
| 2019/0345558 A1 | 11/2019 | Raspe et al. | |
| 2019/0381051 A1 | 12/2019 | Wang et al. | |
| 2021/0000835 A1 | 7/2021 | Wnag et al. | |

FOREIGN PATENT DOCUMENTS

| | | | |
|---|---|---|---|
| CN | 101410093 A | 4/2009 | |
| CN | 101632668 A | 1/2010 | |
| CN | 1835951 B | 6/2010 | |
| CN | 102106806 A | 6/2011 | |
| CN | 102106807 A | 6/2011 | |
| CN | 101906104 B | 6/2013 | |
| CN | 104224754 A | 12/2014 | |
| CN | 104434809 A | 3/2015 | |
| CN | 104887641 A | 9/2015 | |
| CN | 105085517 A | 11/2015 | |
| CN | 105213322 A | 1/2016 | |
| CN | 105616418 A | 6/2016 | |
| CN | 105616419 A | 6/2016 | |
| CN | 105816437 A | 8/2016 | |
| CN | 106474129 A | 3/2017 | |
| CN | 106667952 A | 5/2017 | |
| CN | 106794183 A | 5/2017 | |
| CN | 106831710 A | 6/2017 | |
| CN | 106967061 A | 7/2017 | |
| CN | 107510847 A | 12/2017 | |
| CN | 107666914 A | 2/2018 | |
| CN | 107759594 A | 3/2018 | |
| CN | 108014343 A | 5/2018 | |
| CN | 108017629 A | 5/2018 | |
| CN | 108066303 A | 5/2018 | |
| CN | 108272754 A | 7/2018 | |
| CN | 108653222 A | 10/2018 | |
| CN | 108864078 A | 11/2018 | |
| CN | 105748435 B | 3/2019 | |
| CN | 110099680 A | 8/2019 | |
| CN | 110573183 A | 12/2019 | |
| CN | 106794182 B | 2/2020 | |
| CN | 108066312 B | 3/2020 | |
| CN | 110997666 A | 4/2020 | |
| EP | 0962443 A1 | 12/1999 | |
| EP | 1648889 B1 | 10/2008 | |
| EP | 3255046 B1 | 10/2018 | |
| EP | 3302565 B1 | 11/2019 | |
| IN | 7086CHE2015 | 12/2015 | |
| IN | 20164100225 | 3/2016 | |
| JP | 2000309588 A | 11/2000 | |
| JP | 2008536913 A | 9/2008 | |
| JP | 2013528218 A | 7/2013 | |
| WO | WO-0155148 A1 | 8/2001 | |
| WO | WO-200107041 | 9/2001 | |
| WO | WO-03062236 A1 | 7/2003 | |
| WO | WO-03074056 A1 | 9/2003 | |
| WO | WO-2005005426 A1 | 1/2005 | |
| WO | WO-2006112649 A1 | 10/2006 | |
| WO | WO-2010055119 A2 | 5/2010 | |
| WO | WO-2011063309 A1 | 5/2011 | |
| WO | WO-2011156361 A2 | 12/2011 | |
| WO | WO-2014011398 A1 | 1/2014 | |
| WO | WO-2014128588 A1 | 8/2014 | |
| WO | WO-2015022609 A1 | 2/2015 | |
| WO | WO-2015160986 A2 | 10/2015 | |
| WO | WO-2015165571 A2 | 11/2015 | |
| WO | WO-2016015598 A1 | 2/2016 | |
| WO | WO-2016127963 A1 | 8/2016 | |
| WO | WO-2016156070 A1 | 10/2016 | |
| WO | WO-2016193860 A1 | 12/2016 | |
| WO | WO-2017036390 A1 | 3/2017 | |
| WO | WO-2017115315 A1 | 7/2017 | |
| WO | WO-2017130219 A1 * | 8/2017 | A61P 35/00 |
| WO | WO-2017211788 A1 | 12/2017 | |
| WO | WO-2018071440 A1 | 4/2018 | |
| WO | WO-2018191950 A1 | 10/2018 | |
| WO | WO-2019178239 A1 | 9/2019 | |
| WO | WO-2019220253 A1 | 11/2019 | |

OTHER PUBLICATIONS

"Anonymous: "NCT02311946—A Pilot Study To Investigate The Effect of Concurrent Antacid Administration on the Bioavailability of Six Expermental formulations of Palbociclib" retried from the internet: https://clinicaltrials.gov/ct2/show/NCT02311946—May 28, 2015".

Babic, S. et al. Determination of pKa Values of active pharmaceutical ingredients. Trends in Analytical Chemistry, 26(11):1043-1061 (2007).

Barvian, M., et al., "Pyrido[2,3-d]pyrimidin-7-one Inhibitors of Cyclin-Dependent Kinases" J. Med. Chem. (2000), 43, pp. 4606-4616.

Baselga, Jose et al., Everolimus in Postmenopausal Hormone-Receptor-Positive Advanced Breast Cancer, New England Journal of Medicine, Massachusetts Medical Society, US, vol. 366, No. 6, Feb. 9, 2012 (Feb. 9, 2012), pp. 520-529, XP002684647, ISSN: 0028-4793, DOI: 10.1056/NEJMOALL09653.

Baughn, Linda et al., A novel orally active small molecule potently induces G1 arrest in primary, myeloma cells and prevents tumor growth by specific inhibition of Cdk4/6, Blood, vol. 108, No. 11, Part 1, Nov. 2006 (Nov. 2006), pp. 113A-114A, XP002509897 & 48th. Annual Meeting of the American-Society of Hematology, Orlando, FL, USA; Dec. 9-12, 2006 ISSN: 00064971.

Bhatia, Sangeeta et al., The challenges posed by cancer heterogeneity, Nature Biotechnology, vol. 30, No. 7, Jul. 2012, pp. 604-610.

Chuaprapaisilp, T. et al. Treatment of pustular psoriasis with clofazimine. Br. J. Dermatol. 99(3):303-305 (Sep. 1978).

Conalty, M.L. et al. The antileprosy agent B.663 (Clofazimine) and the reticuloendothelial system. Int. J. Lepr. Other Mycobact Dis. 39(2):479-492 (Apr.-Jun. 1971).

Conklin, Dylan Francis, Identification of Genomic Predictors of Response to the CDK4/6 Inhibitor Palbociclib using the UCLATORL Panel of Human Cancer Cell Lines, University of California, Los Angeles, PhD. Dissertation, 2013, 125 pages.

Curley, Michael D. et al., Seribantumab, an Anti-ERBB3 Antibody, Delays the Onset of Resistance and Restores Sensitivity to Letrozole in an Estrogen Receptor-Positive Breast Cancer Model, Molecular Cancer Therapeutics, vol. 14, No. 11, Nov. 1, 2015 (Nov. 1, 2015), pp. 2642-2652, XP055374862, US ISSN: 1535-7163, DOI: 1158/1535-7163.MCT-15-0169.

Dai Y, et al., Bortezomib and flavopiridol interact synergistically to induce apoptosis in chronic myeloid leukemia cells resistant to imatinib mesylate through both Bcr/Abl-dependent and -independent mechanisms, Blood 20040715 US, vol. 104, No. 2, Jul. 15, 2004 (Jul. 15, 2004), pp. 509-518, XP002509901 ISSN: 006-4971.

El-Deiry, Wafik S., Meeting report: The international conference on tumor progression and therapeutic resistance, Cancer Research, American Association for Cancer Research, American Association for Cancer Reearch, Baltimore, MD, US, vol. 65, No. 11, Jun. 1, 2005 (Jun. 1, 2005), pp. 4475-4484, XP002402154.

Ellis, BP et al. Clofazimine ointment in the treatment of trophic ulcers. S Afr Med J. 47(9):378-9 (Mar. 3, 1973).

Final Office Action dated Jul. 1, 2019, for U.S. Appl. No. 15/613,853.

Final Office Action dated May 4, 2020 for U.S. Appl. No. 16/554,103.

(56) References Cited

OTHER PUBLICATIONS

Finn et al., PD 0332991, a selective cyclin D kinase 4/6 inhibitor, preferentially inhibits proliferation of luminal estrogen receptor-positive human breast cancer cell lines in vitro. Breast Cancer Res. 11 (5):R77 (2009).
Fischer, Peter M. et al., Recent progress in the discovery and development of cyclin-dependent kinase inhibitors, Expert Opinion On Investigational Drugs 200504, GB, vol. 14, No. 4, Apr. 2005 (Apr. 2005), pp. 457-477, XP002509899 ISSN: 1354-3784.
Gartner, E.M. et al. The in vitro and in vivo effects of clofazimine on the motility of neutrophils and transformation of lymphocytes from normal individuals. Lepr Rev. Jun. 1982;53(2):85-90.
Huang, Y. et al. Fundamental aspects of solid dispersion technology for poorly soluble drugs. Acta Pharmaceutica Sinica B, 4(1):18-25 (2014).
Ibrance Drug Label Feb. 2018.
Ibrance product insert, Pfizer Labs, Division of Pfizer Labs Inc., NY, NY 10017, Issued Feb. 2015, https://www.accessdata.fda.gov/drugsatfda_docs/label/2015/207103s000lbl.pdf.
International Search Report and Written Opinion for PCT/CN2021/121696 dated Jan. 5, 2022.
International Search Report and Written Opinion (translated) dated Jan. 11, 2017 for PCT/CN2016/086546.
Kaiser, Cancer Genetics With an Edge, Science, AAAS, vol. 337, pp. 282-284 (2012).
Kelleher, D. et al. Preliminary trial of clofazimine in chronic inflammatory bowel disease. Gut. 1982;23:A432-A463.
Leaf, Clifton, Why We're Losing the War on Cancer—and How to Win It, (2004) Fortune, Time Inc., pp. 1-26.
Lee, S.J. et al. Treatment of chronic graft-versus-host disease with clofazimine. Blood. 89(7):2298-2302 (Apr. 1, 1997).
Liu, Da David, MDM2 Levels Modulate the Cellular Senescence Response to CDK4 Inhibition, Dissertation Presented to the Faculty of the Cornell Graduate School, Mar. 2013, pp. 1-11.
Mackey, JP et al. Clofazimine in the treatment of discoid lupus erythematosus. Br. J. Dermatol. 91(1):93-96 (Jul. 1974).
Merck Millipore, ASK26/MDM2 Antibody Sampler Kit-Human.
Miller, Todd W., et al., ER[alpha]-dependent E2F transcription can mediate resistance to estrogen deprivation in human breast cancer, Cancer Discovery, American Association for Cancer Research, US, vol. 1, No. 4, Sep. 1, 2011 (Sep. 1, 2011), pp. 338-351, XP002683182, ISSN: 2159-8274, DOI: 10.1158/2159-8290.CD-11-0101.
"Mitra, et al., "Impaired Drug Absorption Due to High Stomach pH: A Review of Strategies for Mitigation of Such Effect to Enable Pharmaceutical Product Development", Mol. Pharm., vol. 10, No. 11, pp. 3970-3979".
Dragicevic, N. Eds., Percutaneous Penetration Enhancers Chemical Methods in Penetration Enhancement[M], Springer, 2015.
NCI, What is Cancer?, National Institutes of Health, Published Feb. 9, 2015, pp. 1-16.
Non-Final Office Action dated Dec. 20, 2019, for U.S. Appl. No. 16/554,112.
Office Action issued for JP2020-191821 dated Nov. 5, 2021 (English).
Office Action issued for JP2020-191821 dated Nov. 5, 2021 (Non-English).
Patani et al. Bioisosterism: A Rational Approach in Drug Design. Chem. Rev. 96:3147-3176 (1996).
Patel, VB et al. A topical dosage form of liposomal clofazimine: research and clinical implications. Pharmazie. 54(6):448-451 (Jun. 1999).
Podmore, P. et al. Clofazimine—an effective treatment for Melkersson-Rosenthal syndrome or Miescher's cheilitis. Clin Exp Dermatol. Mar. 1986;11(2):173-178.
Pradaxa Drug Label—Revised Mar. 2018; 27 pages.
Ren, Yunzhao R. et al. Clofazimine Inhibits Human Kv1.3 Potassium Channel by Perturbing Calcium Oscillation in T Lymphocytes. PLoS One 3(12):e4009:1-11 (2008).
Richard S Finn, et al., The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase study, The Lancet. Oncology, Jan. 1, 2015 (Jan. 1, 2015), pp. 25-35.
Rocca, et al. Palbociclib (PD 0332991) : targeting the cell cycle machinery in breast cancer. Expert Opinion Pharmacother. Feb. 2014;15(3):407-20. Epub Dec. 26, 2013.
Sabbioni, et al., Biomonitoring of arylamines and nitroarenes Biomarkers, 2002, 7(5), pp. 347-421.
Schwartz, G.K., et al., Targeting the cell cycle: A new approach to cancer therapy, Journal of Clinical Oncology 2005 US, vol. 23, No. 36, 2005, pp. 9408-9421, XP002509900 ISSN: 0732-183X.
Slamon, Dennis J., 2013 Breast Cancer Highlight—Palbociclib (PD-0332991), a Breakthrough Therapy for Breast Cancer, Breast Cancer Research Program, Congressionally Directed Medical Research Programs, May 15, 2013 (May 15, 2013), pp. 1-2, XP055158107, Retrieved from the Internet: URL:http://cdmrp.army.mil/bcrp/research_highlights/13slamon_highlight.shtml.
Sun, W. et al., Impact of acid-reducing agents (ARAS) on the pharmacokinetics of palbociclib, a weak base with a ph-dependent solubility, under different food intake conditions, European Journal of Cancer, Dec. 31, 2015, XP055426702.
Sun, W. et al., Impact of acid-reducing agents (ARAS) on the pharmacokinetics of palbociclib, a weak base with ph-dependent solubility under differing food intake conditions, European Journal of Cancer, (Dec. 31, 2015), S59.
Sutherland, Robert L., et al., CDK inhibitors as potential breast cancer therapeutics: new evidence for enhanced efficacy in ER+ disease, Breast cancer research : BCR, Jan. 1, 2009 (Jan. 1, 2009), pp. 112-112, XP055145540, England DOI: 10.1186/bcr2454.
Toogood. Cyclin-dependent kinase inhibitors for treating cancer. Med Res Rev. Nov. 2001;21(6):487-98.
Toogood, et al., Discovery of a Potent and Selective Inhibitor of Cyclin-Dependent Kinase 4/,J. Med. Chem., 48:2388-2406 (2005).
Trumpp-Kallmeyer et al. Development of a Binding Model to Protein Tyrosine Kinases for Substituted Pyrido[2,3-d]pyrimidine Inhibitors. J. Med. Chem. 41 (11):1752-1763 (Apr. 28, 1998).
U.S. Appl. No. 15/613,853 Office Action dated Jan. 18, 2019.
Van Tine, B.A., et al., ER and PI3K Independently Modulate Endocrine Resistance in ER-PositiveBreast Cancer, Cancer Discovery, vol. 1, No. 4, Sep. 1, 2011 (Sep. 1, 2011), pp. 287-288, XP055145623. ISSN: 2159-8274, DOI: 10.1158/2159-8290.CD-11-0192.
Wistuba, Ignacio I., et al., Methodological and practical challenges for personalized cancer therapies, Nature Rev. Clinical Oncology, 2011, Nature Publishing Group, vol. 8, pp. 135-141.

\* cited by examiner

PHARMACEUTICAL COMPOSITIONS OF AMORPHOUS SOLID DISPERSIONS AND METHODS OF PREPARATION THEREOF

CROSS REFERENCE TO RELATED APPLICATION

This application claims the benefit of patent application CN 202011046895.4, filed Sep. 29, 2020, the disclosure of which is hereby incorporated by reference in its entirety.

BACKGROUND

Poorly water-soluble drugs pose a challenge in drug formulation due to their limited solubilities and in some cases the food effect on the solubilities. For example, 6-acetyl-8-cyclopentyl-5-methyl-2-[(5-piperazin-1-ylpyridin-2-yl)amino]pyrido[2,3-d]pyrimidin-7-one, also known as palbociclib, is depicted below.

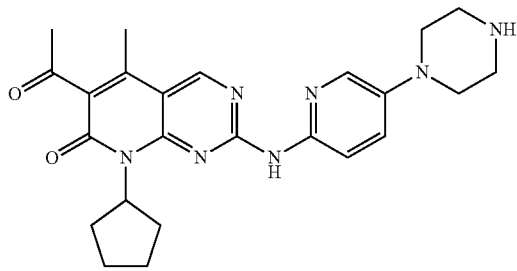 [SMILES: CC(=O)c1c(C)c2cnc(Nc3ccc(N4CCNCC4)cn3)nc2n(C2CCCC2)c1=O]

An additional example, (E)-N-{4-[3-chloro-4-(pyridin-2-yl methoxy)anilino]-3-cyano-7-ethoxyquinolin-6-yl}-4-(dimethylamino)but-2-enamide maleate, also known as neratinib maleate, is depicted below.

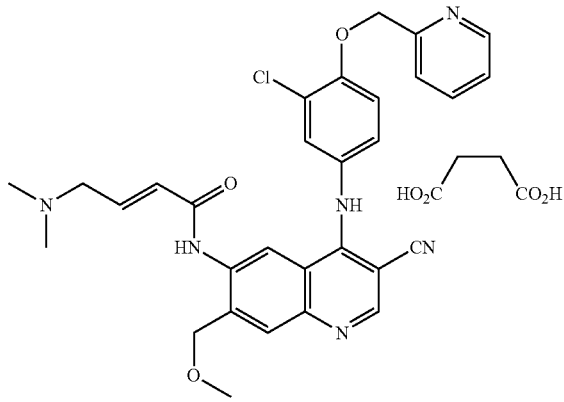

At present, palbociclib has been approved for sale in the United States. According to the instructions for the approved product of palbociclib in the United States, one of seven patients has poor absorption upon administration of the palbociclib product. The poor solubility of the drug contributes to the poor absorption in patients. It is therefore necessary to improve the dosage form of poorly water-soluble drugs (such as palbociclib or neratinib), so as to increase the dissolution and bioavailability thereof.

BRIEF SUMMARY

Disclosed herein are compositions of amorphous solid dispersions and pharmaceutical compositions comprising an API, or a salt or solvate thereof, and methods of making and using the same.

Disclosed herein is an amorphous solid dispersion, wherein the amorphous solid dispersion comprises: a first acid, wherein the first acid is an organic acid that has a pKa of at most 2; a second acid, wherein the second acid has a pKa greater than 2; a hydrophilic high-molecular weight material; and palbociclib, a salt of palbociclib, or any combination thereof, wherein the salt of palbociclib comprises the palbociclib and the first acid, wherein the molar ratio of the first acid to palbociclib is from about 0.5:1 to about 5:1, and wherein the weight ratio of the second acid to palbociclib is from about 0.1:1 to about 10:1.

Disclosed herein is an amorphous solid dispersion, wherein the amorphous solid dispersion comprises: a first acid, wherein the first acid is an acid that has a pKa of at most 2; a second acid, wherein the second acid has a pKa greater than 2; a hydrophilic high-molecular weight material; and palbociclib, a salt of palbociclib, or any combination thereof, wherein the salt of palbociclib comprises the palbociclib and the first acid, wherein a molar ratio of the first acid to palbociclib is from about 0.5:1 to about 3:1, and wherein a weight ratio of the second acid to palbociclib is from about 0.2:1 to about 1.5:1.

Disclosed herein is an amorphous solid dispersion, wherein the amorphous solid dispersion comprises:
a) an active pharmaceutical ingredient (API), wherein the API comprises a compound of Formula

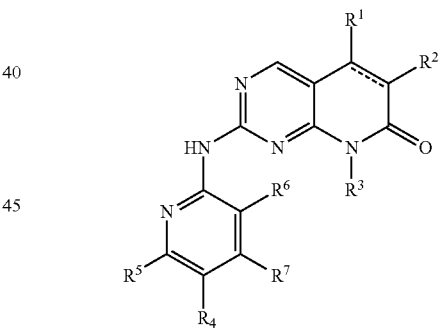

Formula (I)

or a pharmaceutically acceptable salt thereof, wherein,

------- represents a single bond or a double bond;

$R^1$ is $C_1$-$C_6$ alkyl;

$R^3$ is $C_1$-$C_8$ alkoxy, $C_3$-$C_7$ cycloalkyl, or $C_3$-$C_7$-heterocyclyl;

$R^2$ and $R^4$ are each independently selected from hydrogen, halogen, $C_1$-$C_8$ alkyl, $C_3$-$C_7$ cycloalkyl, $C_3$-$C_7$ heterocycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^{10}$, $SR^{10}$, $NR^{10}R^{11}$, $N(O)R^{10}R^{11}$, $P(O)(OR^{10})(OR^{11})$, $(CR^{10}R^{11})_m NR^{12}R^{13}$, $COR^{10}$, $(CR^{10}R^{11})_m C(O)R^{12}$, $CO_2R^{10}$, $CONR^{10}R^{11}$, $C(O)NR^{10}SO_2R^{11}$, $NR^{10}SO_2R^{11}$, $C(O)NR^{10}R^{11}$, $S(O)_2R^{10}$, $SO_2NR^{10}R^{11}$, $P(O)(OR^{10})(OR^{11})$, $(CR^{10}R^{11})_m P(O)(OR^{12})(OR^{13})$, $(CR^{10}R^{11})_m$-aryl, $(CR^{10}R^{11})_m$-heteroaryl, and $-CR^{10}=CR^{11}C(O)R^{12}$;

each of $R^5$, $R^6$, and $R^7$ is independently hydrogen, halogen, $C_1$-$C_6$ alkyl, $C_1$-$C_6$ haloalkyl, $C_1$-$C_8$ alkoxy, $C_1$-$C_8$ alkoxyalkyl, CN, $NO_2$, $OR^{10}$, $NR^{10}R^{11}$, $CO_2R^{10}$, $COR^{10}$, $S(O)_nR^{10}$, $CONR^{10}R^{11}$, $NR^{10}COR^{11}$, $NR^{10}SO_2R^{11}$, $SO_2NR^{10}R^{11}$, or $P(O)(OR^{10})(OR^{11})$;

each of $R^{10}$, $R^{11}$, $R^{12}$ and $R^{13}$ is independently hydrogen, $C_1$-$C_8$ alkyl, $C_2$-$C_8$ alkenyl, $C_2$-$C_8$ alkynyl, arylalkyl, cycloalkyl, heterocycloalkyl, aryl, or heteroaryl;

m is 0, 1, 2, 3, 4, 5, or 6; and n is 0, 1 or 2;

b) a first acid, wherein the first acid is an organic acid that has a pKa of at most 2; c) a second acid, wherein the second acid has a pKa greater than 2; and d) a hydrophilic high-molecular weight material, wherein the salt of Formula (I) comprises the API and the first acid, wherein a molar ratio of the first acid to Formula (I) is from about 0.5:1 to about 5:1, and wherein a weight ratio of the second acid to Formula (I) is from about 0.1:1 to about 10:1.

Disclosed herein is an amorphous solid dispersion, wherein the amorphous solid dispersion comprises: a) a pharmaceutically acceptable salt of neratinib; and b) a hydrophilic high-molecular weight material.

Disclosed herein is an amorphous solid dispersion, wherein the amorphous solid dispersion comprises: a) neratinib, or a pharmaceutically acceptable salt thereof; b) two or more pharmaceutically acceptable acids; and c) a hydrophilic high-molecular weight material, wherein the pharmaceutically acceptable salt of neratinib comprises neratinib and at least one of the two or more pharmaceutically acceptable acids, and wherein a molar ratio of the two or more acids to the API is from about 0.1:1 to about 20:1.

Disclosed herein is an amorphous solid dispersion, wherein the amorphous solid dispersion comprises:
a) an active pharmaceutical ingredient (API), wherein the API comprises a compound of Formula (II),

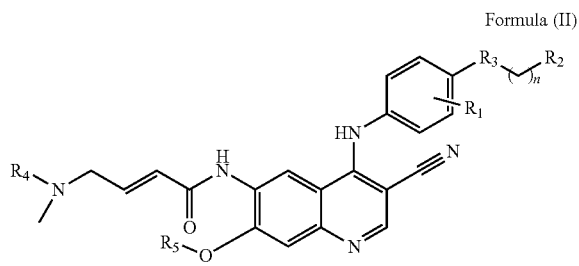

Formula (II)

or a pharmaceutically acceptable salt thereof,
wherein,
$R_1$ is halogen;
$R_2$ is a pyridinyl, thiophene, pyrimidine, thiazole, or phenyl optionally substituted with up
to three substituents;
$R_3$ is —O— or —S—;
$R_4$ is $C_{1-3}$ alkyl or $C_{1-3}$ heteroalkyl;
$R^5$ is ethyl or methyl;
n is 0 or 1;
b) one or more acids; and c) a hydrophilic high-molecular weight material.

Disclosed herein is an amorphous solid dispersion, wherein the amorphous solid dispersion comprises: a) an active pharmaceutical ingredient (API), wherein the API is at least partially protonated, and wherein the API has a log P of at least 2; b) one or more acids; and c) a hydrophilic high-molecular weight material, wherein a molar ratio of the one or more acids to the API is from about 0.1:1 to about 20:1.

Disclosed herein is an amorphous solid dispersion, wherein the amorphous solid dispersion comprises: a) a first acid, wherein the first acid is an organic acid that has a pKa of at most 2; b) a second acid, wherein the second acid has a pKa greater than 2; c) a hydrophilic high-molecular weight material; and d) an active pharmaceutical ingredient (API), a pharmaceutically acceptable salt of the API, or any combination thereof, wherein the pharmaceutically acceptable salt of the API comprises the API and the first acid, wherein the molar ratio of the first acid to API is from about 0.5:1 to about 5:1, and wherein the weight ratio of the second acid to API is from about 0.1:1 to about 10:1.

Disclosed herein is a pharmaceutical composition, wherein the pharmaceutical composition comprises: a) an amorphous solid dispersion described herein, and b) one or more pharmaceutically acceptable carriers or excipients.

Disclosed herein is a pharmaceutical composition, wherein the pharmaceutical composition comprises: a) an amorphous solid dispersion, the amorphous solid dispersion comprising: i. an active pharmaceutical ingredient (API), a pharmaceutically acceptable salt thereof, or any combination thereof; ii. one or more interior acids; iii. a hydrophilic high-molecular weight material; and iv. optionally, an adsorbent; b) one or more exterior acids; c) one or more pharmaceutically acceptable carriers or excipients, wherein the mass ratio of the one or more exterior acids to API is from about 0.1 to about 1:1.

Disclosed herein is a method of manufacturing a pharmaceutical composition comprising an amorphous solid dispersion, the method comprising: (a) combining (i) a first acid, wherein the first acid is an organic acid that has a pKa of at most 2; (ii) a second acid, wherein the second acid has a pKa greater than 2; and (iii) a hydrophilic high-molecular weight material, (iv) palbociclib, a salt of palbociclib, or any combination thereof, wherein the salt of palbociclib comprises palbociclib and the first acid; wherein the molar ratio of the first acid to palbociclib is from about 0.5:1 to about 5:1, and wherein the weight ratio of the second acid to palbociclib is from about 0.1:1 to about 10:1, (v) a solvent; thereby producing a mixture; and (b) removing at least a portion of the solvent from the mixture, thereby producing an amorphous solid dispersion.

Disclosed herein is a method of manufacturing an amorphous solid dispersion comprising an amorphous solid dispersion, the method comprising: (a) combining (i) palbociclib, wherein the palbociclib is at least partially protonated; (ii) a first acid, wherein the first acid is an organic acid that has a pKa of at most 2; (iii) a second acid, wherein the second acid has a pKa greater than 2; and (iv) a hydrophilic high-molecular weight material, wherein the molar ratio of the first acid to palbociclib is from about 0.5:1 to about 5:1, and wherein the weight ratio of the second acid to palbociclib is from about 0.1:1 to about 10:1 (v) a solvent; thereby producing a mixture; and (b) removing at least a portion of the solvent from the mixture, thereby producing an amorphous solid dispersion.

Disclosed herein is a method of treating cancer, comprising administering to a subject in need thereof a pharmaceutical composition or an amorphous solid dispersion described herein.

Disclosed herein is use of the pharmaceutical composition or the amorphous solid dispersion or pharmaceutical composition described herein for the treatment of cancer in a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
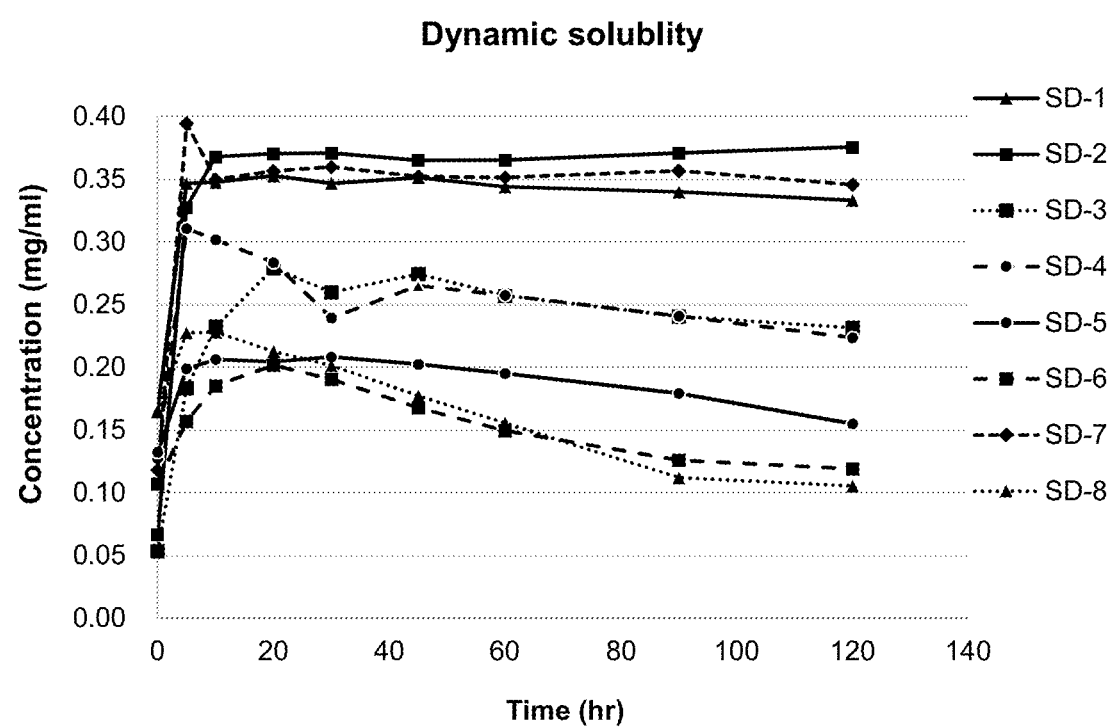
FIG. 1 is a plot of the dissolution rate for amorphous solid dispersions.

The present disclosure relates to pharmaceutical compositions and methods of administering thereof, the pharmaceutical compositions comprising an amorphous solid dispersion comprising an API. In some embodiments, the disclosed pharmaceutical composition has an increased solubility and bioavailability compared to a corresponding pharmaceutical composition without an amorphous solid dispersion. In some embodiments, the disclosed pharmaceutical composition is less susceptible to food effect compared to a corresponding pharmaceutical composition without an amorphous solid dispersion. An exemplary amorphous solid dispersion disclosed herein comprising palbociclib as the API has increased solubility and bioavailability relative to commercially available compositions. Increasing the solubility and bioavailability of drugs can lead to lower drug loadings in pharmaceutical formulations. Such lower loadings benefit the patient by reducing the costs and side effects of the medication.

In one aspect, the present disclosure relates to an amorphous solid dispersion comprising a protonated API. The solubility of a drug can be accomplished by the ionization of the drug through protonation of one or more basic sites on the drug, e.g., forming an acidic salt of the drug and administering the salt. However, in some cases, protonated drugs can suffer from a loss of stability and may decompose more quickly under storage conditions. Amorphous solid state dispersions of protonated APIs can enhance stability. Therefore, there is a need for pharmaceutical formulations comprising the described amorphous solid dispersions comprising a protonated API.

The need for the formulations described herein is particularly acute in patients with conditions that require treatments that result in the elevation stomach pH. For example, patients suffering from Gastroesophageal Reflux Disease (GERD) may alleviate symptoms by administering pharmaceutical formulations comprising proton pump inhibitors (PPI) or antacids and raise the pH of the stomach. However, if a subsequent drug relies on protonation in the stomach to increase dissolution and bioavailability of the drug, an elevated pH in the stomach will reduce its efficacy. The pharmaceutical compositions and methods described herein increase the dissolution and bioavailability of particular APIs in subjects with stomachs having elevated pH levels.

In one aspect, the present disclosure relates to an amorphous solid dispersion comprising a protonated API. In some embodiments, the unprotonated API is poorly soluble in water or other polar protic solvents. To form an amorphous solid dispersion of the API, the API is first dissolved to form a solution. A strong acid (pKa of less than 2) can be useful to ionize the poorly soluble API such that the protonated API can be dissolved into a solution.

In some embodiments, large scale manufacturing of an amorphous solid dispersion of a protonated API presents challenges. The corrosivity of the acid, with respect to the manufacturing equipment being utilized, can affect the cost of production. In some embodiments, a strong organic acid is used to decrease corrosion of the manufacturing equipment. In some embodiments, the strong organic acid is an aliphatic sulfonic acid or aromatic sulfonic acid.

In one aspect, the present disclosure relates to an amorphous solid dispersion comprising a protonated API, a first acid with a pKa of less than 2, and a second acid with a pKa more than 2. In some embodiments, the first acid is useful in ionizing the API such that the protonated API can dissolve into a solution. Therefore, the molar ratio of the API to the first acid can be an useful parameter. The second acid is useful for maintaining the solubility of the API as the progresses through the gastrointestinal tract. Therefore, the mass ratio of the second acid can be a useful parameter. In some embodiments, the first and/or second acids are physically stable and unlikely to form crystals.

In some embodiments, an API disclosed herein is palbociclib. Palbociclib has two pKa values, 3.9 and 7.4 respectively. When the pH value is below 4, the solubility is high. When the pH value is higher than 4, the solubility of the drug drops significantly to less than about 0.02 mg/ml. In some embodiments, the pharmaceutical compositions disclosed herein comprise an amorphous solid dispersion comprising protonated palbociclib. The amorphous solid dispersion substantially increases the bioavailability of palbociclib upon administration, particularly in stomachs with elevated pH levels.

In some embodiments, an API disclosed herein is neratinib maleate. Neratinib maleate has two pKa values, 4.7 and 7.7 respectively. When the pH value is 1.2, neratinib maleate has a solubility of 32.90 mg/mL. When the pH value is approximately 5.0, the solubility of the drug drops significantly to about 0.08 mg/ml or less. In some embodiments, the pharmaceutical compositions disclosed herein comprise an amorphous solid dispersion comprising neratinib maleate.

Definitions

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The singular forms "a," "an," and, "the" include plural referents unless the context clearly dictates otherwise. Thus, for example, reference to "the surfactant" includes reference to one or more specific surfactants, reference to "an antioxidant" includes reference to one or more of such additives.

The term "subject" as used herein refers to a mammal (e.g., a human, mouse, rat, guinea pig, dog, cat, horse, cow, pig, or non-human primate, such as a monkey, chimpanzee or baboon).

"AUC" as used herein refers to the area under the plasma drug concentration-versus-time curve extrapolated from zero time to infinity. "$C_{max}$" as used herein refers to the highest drug concentration observed in plasma following an extravascular dose of drug. "$T_{max}$" as used herein refers to the time after administration of a drug when the maximum plasma concentration is reached.

"Therapeutically equivalent" when used in connection with a pharmaceutical composition described herein refers to an amount or quantity of a pharmaceutically acceptable salt of a pharmaceutically active agent that is equivalent to the therapeutically effective amount of the free base of the pharmaceutically active agent.

The use of the term "or" in the claims is used to mean "and/or" unless explicitly indicated to refer to alternatives only or the alternatives are mutually exclusive, although the disclosure supports a definition that refers to only alternatives and to "and/or."

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has," or "includes" one or more steps is not limited to possessing only those one or more steps and also covers other unlisted steps.

As used herein, the term "therapeutic" means an agent utilized to treat, combat, ameliorate, prevent, or improve an unwanted condition or disease of a patient.

"Administering", when used in conjunction with a therapeutic, means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with Compound A formulation, can include, but is not limited to, providing Compound A formulation into or onto the target tissue; providing Compound A formulation systemically to a patient by, e.g., oral administration whereby the therapeutic reaches the target tissue or cells. "Administering" a formulation may be accomplished by oral administration or by other methods alone or in combination with other known techniques.

A "therapeutically effective amount" or "effective amount" as used herein, refers to the amount of active compound or pharmaceutical agent that elicits a biological or medicinal response in a tissue, system, animal, individual, or human that is being sought by a researcher, veterinarian, medical doctor, or other clinician, which includes one or more of the following: (1) preventing the disease; for example, preventing a disease, condition, or disorder in an individual that may be predisposed to the disease, condition, or disorder but does not yet experience or display the pathology or symptomatology of the disease, (2) inhibiting the disease; for example, inhibiting a disease, condition, or disorder in an individual that is experiencing or displaying the pathology or symptomatology of the disease, condition, or disorder (i.e., arresting further development of the pathology and/or symptomatology), and (3) ameliorating the disease; for example, ameliorating a disease, condition, or disorder in an individual that is experiencing or displaying the pathology or symptomatology of the disease, condition, or disorder (i.e., reversing the pathology and/or symptomatology).

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Methoxyl" refers to the —O-Me radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Hydroxy" or "hydroxyl" refers to the —OH radical.
"Hydroxyamino" refers to the —NH—OH radical.
"Acyl" refers to a substituted or unsubstituted alkylcarbonyl, substituted or unsubstituted alkenylcarbonyl, substituted or unsubstituted alkynylcarbonyl, substituted or unsubstituted cycloalkylcarbonyl, substituted or unsubstituted heterocycloalkylcarbonyl, substituted or unsubstituted arylcarbonyl, substituted or unsubstituted heteroarylcarbonyl, amide, or ester, wherein the carbonyl atom of the carbonyl group is the point of attachment. Unless stated otherwise specifically in the specification, an alkylcarbonyl group, alkenylcarbonyl group, alkynylcarbonyl group, cycloalkylcarbonyl group, amide group, or ester group is optionally substituted, for example, with oxo, halogen, amino, nitrile, nitro, hydroxyl, haloalkyl, alkoxy, aryl, cycloalkyl, heterocycloalkyl, heteroaryl, and the like.

"Acyl-sulfonamide" refers to a monovalent radical where the carbon atom of a carbonyl is bound to a sulfonamide group. Exemplary acyl-sulfonamides include —C(O)NR$^a$S (O)$_2$R$^a$, —C(O)NR$^a$S(O)$_2$N(R$^a$)$_2$, —NR$^a$S(O)$_2$C(O)R$^a$, —NR$^a$S(o)$_2$C(O)N(R$^a$)$_2$, —C(O)NR$^a$S(o)$_2$C(O)N(R$^a$)$_2$, —NR$^a$S(O)$_2$NR$^a$C(O)N(R$^a$)$_2$, —C(O)NR$^a$S(O)$_2$NR$^a$C(O)N(R$^a$)$_2$, and —C(O)S(O)$_2$N(R$^a$)$_2$, where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkyl" refers to an optionally substituted straight-chain, or optionally substituted branched-chain saturated hydrocarbon monoradical. An alkyl group can have from one to about twenty carbon atoms, from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, —NO$_2$, or —C≡CH. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds. In some embodiments, an alkenyl group has from two to about ten carbon atoms, or two to about six carbon atoms. The group may be in either the cis or trans configuration about the double bond(s), and should be understood to include both isomers. Examples include, but are not limited to, ethenyl (—CH═CH$_2$), 1-propenyl (—CH$_2$CH═CH$_2$), isopropenyl [—C(CH$_3$)═CH$_2$], butenyl, 1,3-butadienyl, and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds. In some embodiments, an alkynyl group has from two to about ten carbon atoms, more preferably from two to about six carbon atoms. Examples include, but are not limited to, ethynyl, 2-propynyl, 2-butynyl, 1,3-butadiynyl, and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms, or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkylamino" refers to a radical of the formula —N(R$_a$)$_2$ where R$_a$ is an alkyl radical as defined, or two R$_a$, taken together with the nitrogen atom, can form a substituted or unsubstituted $C_2$-$C_7$ heterocyloalkyl ring. Unless stated otherwise specifically in the specification, an alkylamino group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylamino is optionally substituted with oxo, halogen, —CN, —CF$_3$, —OH, —OMe, —NH$_2$, or —NO$_2$. In some embodiments, an alkylamino is optionally substituted with oxo, halogen, —CN, —CF$_3$, —OH, or —OMe. In some embodiments, the alkylamino is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising at least one aromatic ring. In some embodiments, an aryl comprises hydrogens and 6 to 30 carbon atoms. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, alkylamino, aminoalkyl, nitrile, nitro, hydroxyl, alkyl, alkenyl, alkynyl, haloalkyl, heteroalkyl, alkoxy, aryl, cycloalkyl, heterocycloalkyl, heteroaryl, —S(O)$_2$NH—C$_1$-C$_6$alkyl, and the like. In some embodiments, an aryl is optionally substituted with halogen, methyl, ethyl, —CN, —CF$_3$, —OH, —OMe, —NH$_2$, —NO$_2$, —S(O)$_2$NH$_2$, —S(O)$_2$NHCH$_3$, —S(O)$_2$NHCH$_2$CH$_3$, —S(O)$_2$NHCH(CH$_3$)$_2$, —S(O)$_2$N(CH$_3$)$_2$, or —S(O)$_2$NHC(CH$_3$)$_3$. In some embodiments, an aryl is optionally substituted with halogen, methyl, ethyl, —CN, —CF$_3$, —OH, or —OMe. In some embodiments, the aryl is optionally substituted with halogen. In some embodiments, the aryl is substituted with alkyl, alkenyl, alkynyl, haloalkyl, or heteroalkyl, wherein each alkyl, alkenyl, alkynyl, haloalkyl, heteroalkyl is independently unsubstituted, or substituted with halogen, methyl, ethyl, —CN, —CF$_3$, —OH, —OMe, —NH$_2$, or —NO$_2$.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged, or spiro ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halogens. In some embodiments, the alkyl is substituted with one, two, or three halogens. In some embodiments, the alkyl is substituted with one, two, three, four, five, or six halogens. Haloalkyl can include, for example, iodoalkyl, bromoalkyl, chloroalkyl, and fluoroalkyl. For example, "fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocyclyl," "heterocycle," or "heterocyclic" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused, bridged, or spirocyclic ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$CN$, —$R^b$—$O$—$R^e$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^e$ is a straight or branched alkylene or alkenylene chain, and where each of the above substituents is unsubstituted unless otherwise indicated.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous, and sulfur. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized.

Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides, and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —$CF_3$, —OH, —OMe, —$NH_2$, or —$NO_2$. In some embodiments, a heterocycloalkyl is optionally substituted with oxo, halogen, methyl, ethyl, —CN, —$CF_3$, —OH, or —OMe. In some embodiments, the heterocycloalkyl is optionally substituted with halogen.

"Heteroaryl" refers to a ring system radical comprising carbon atom(s) and one or more ring heteroatoms that are selected from the group consisting of nitrogen, oxygen, phosphorous, and sulfur, and at least one aromatic ring. In some embodiments, a heteroaryl is a 5- to 14-membered ring system radical comprising one to thirteen carbon atoms, one to six heteroatoms selected from the group consisting of nitrogen, oxygen, phosphorous, and sulfur. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

As used herein, C$_1$-C$_x$ (or C$_{1-x}$) includes C$_1$-C$_2$, C$_1$-C$_3$ . . . C$_1$-C$_x$. By way of example only, a group designated as "C$_1$-C$_4$" indicates that there are one to four carbon atoms in the moiety, i.e. groups containing 1 carbon atom, 2 carbon atoms, 3 carbon atoms or 4 carbon atoms. Thus, by way of example only, "C$_1$-C$_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof. As used herein, "treating" includes the concepts of "alleviating", which refers to lessening the frequency of occurrence or recurrence, or the severity, of any symptoms or other ill effects related to a disorder and/or the associated side effects. The term "treating" also encompasses the concept of "managing" which refers to reducing the severity of a particular disease or disorder in a patient or delaying its recurrence, e.g., lengthening the period of remission in a patient who had suffered from the disease. The term "treating" further encompasses the concept of "prevent," "preventing," and "prevention," that is, reducing the probability of developing a disease or condition in a subject, who does not have, but is at risk of or susceptible to developing a disease or condition.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.).

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure. A person of ordinary skill in the art would understand that, while only a single bond is shown, a double bond is intended for those substituents.

Amorphous Solid Dispersion

In one aspect, the present disclosure relates to an amorphous solid dispersion comprising an API and pharmaceutical compositions comprising the amorphous solid dispersion. In some embodiments, a disclosed amorphous solid dispersion comprises an API, a first acid, a second acid, and a hydrophilic high-molecular weight material. In some embodiments, a disclosed amorphous solid dispersion comprises an API, a surfactant, a non-ionic hydrophilic polymer, and optionally an adsorbent. In some embodiments, a disclosed amorphous solid dispersion comprises an adsorbent such as silica. In some embodiments, a disclosed amorphous solid dispersion comprises a protonated API, an anion of an organic acid, an anion of an inorganic acid, and a high-molecular weight material. In some embodiments, the API comprises palbociclib. In some embodiments, the API comprises neratinib. In some embodiments, the API is at least partially protonated. In some embodiments, the API has a log P of at least about 1 in an unprotonated form and has a pKa of about 3 to about 10. In some embodiments, the first acid is an organic acid that has a pKa of at most 2. In some embodiments, a molar ratio of the second acid to the first acid is from about 0.2:1 to about 20:1. In some embodiments, the surfactant is selected from polymeric non-ionic surfactants and phospholipids. In some embodiments, amorphous solid dispersions described herein comprise an API, an auxiliary acid, and a hydrophilic high-molecular weight material, wherein the auxiliary acid is an organic acid, an inorganic acid, or a combination thereof. In some embodiments, the amorphous solid dispersions described here are homogenous amorphous solid dispersions.

In some embodiments, a solid dispersion is a solid state solution wherein an API (or acidic API salt) and high-molecular weight material act as solute and solvent, respectively. The solid dispersion can form multiple structures depending on the composition and sample processing history. When the API loading is lower than the equilibrium solubility of API in the high-molecular weight material, the drug is molecularly dispersed within the polymer matrix and forms a thermodynamically stable, homogeneous solution. A homogenous solution is often attainable at very low API loading and/or high temperature. For higher loadings, the mixture can become a supersaturated solution and the drug precipitates out. This can result in a dispersion of crystalline API particles in a high-molecular weight material matrix, in which the drug concentration corresponds to its equilibrium solubility at that temperature. Alternatively, as API crystallization can be a slow and unpredictable process, an intermediate meta-stable structure may form in which amorphous API is dispersed molecularly or dispersed as aggregates in a high-molecular weight material matrix containing the API in a non-crystalline amorphous state. Such amorphous solid dispersions can increase apparent solubility of the API and provide superior dissolution properties, as compared to the crystalline API.

In some embodiments, the amorphous solid dispersions described herein comprise APIs that are poorly soluble in free base form. In some embodiments, the poorly soluble APIs exhibit enhanced solubility when protonated to form the mono-, di-, or tri-protonated API salt (or an equilibrium mixture thereof). Generally, as the protonation state of the API increases, the solubility of the protonated API also increases.

The formation of an amorphous solid dispersion comprising a protonated API salt presents challenges. Protonated API salts with high lattice energies tend to be driven to crystalize out of any initially formed amorphous solid dispersions due to the high stability of the crystalline state. Lattice energies increase with the valency/charge or the cations and anions in the API salt. Therefore, as the protonation state of the API increases (e.g. from mono-protonated to di-protonated to tri-protic salts), so too does the lattice energy of the API salt. These effects can compound to yield highly protonated API salts that easily crystalize and are therefore difficult to formulate as amorphous solid dispersions.

In the case of acidic salts of APIs, another contributor to the strength of the lattice energy is the strength of the acid. Stronger acids often result in stronger lattices due to the higher dissociation of the proton and conjugate base. In addition, the size of the conjugate base relative to the protonated API salt can also be a factor in determining lattice energy. Like size cations and anions generally form stronger lattices.

Described herein are amorphous solid dispersions of protonated APIs. In some embodiments, the APIs are protonated by two distinct acids of specific classes and strengths. For example, described herein are amorphous solid dispersions of palbociclib comprising a first acid, wherein the first acid is an organic acid that has a pKa of at most 2; and a second acid, wherein the second acid has a pKa greater than 2; and a hydrophilic high-molecular weight material. Applicant has found, surprisingly, that amorphous solid dispersions of palbociclib with the above described parameters are stable as amorphous solid dispersions and show superior bioavailability to the equivalent marketed drug product.

A herein described amorphous solid dispersion can have a particle size distribution. In some embodiments, a median diameter of the amorphous solid dispersion is from about 10 nm to about 500 µm. In some embodiments, a median diameter of the amorphous solid dispersion is from about 100 nm to about 300 µm. In some embodiments, a median diameter of the amorphous solid dispersion is from about 500 nm to about 50 µm. In some embodiments, a median diameter of the amorphous solid dispersion is from about 1 µm to about 20 µm. In some embodiments, a median diameter of the amorphous solid dispersion is from about 1 µm to about 15 µm.

In some embodiments, the terms D10, D50, and D90 are used to describe a particle size distribution. D50 value, the median diameter, refers to a diameter value where half of the particle population (by volume) have a diameter larger than and half of the particle population have a diameter smaller than the D50 value. Similarly, D90 refers to a diameter value where 10% of the particle population (by volume) have a diameter larger than and 90% of the particle population have a diameter smaller than the D90 value. D10 refers to a diameter value where 90% of the particle population (by volume) have a diameter larger than and 10% of the particle population have a diameter smaller than the D10 value. Particle size and size distribution can be measured by commercially available light scattering particle sizer analyzers, such as Malvern Particle Size Analyzer 3000.

In some embodiments, a herein described amorphous solid dispersion has a particle size distribution with a D50 value of about 100 nm to about 100 µm, or any ranges therebetween. In some embodiments, the D50 value is about 100 nm, about 500 nm, about 1 µm, about 5 µm, about 10 µm, about 15 µm, about 20 µm, about 25 µm, about 30 µm, about 40 µm, about 50 µm, about 60 µm, about 75 µm, or about 100 µm. In some embodiments, the D50 value is at least about 100 nm, at least about 500 nm, at least about 1 µm, at least about 5 pam, at least about 10 µm, at least about 15 µm, or at least about 20 µm. In some embodiments, the D50 value is at most about 500 nm, at most about 1 µm, at most about 5 µm, at most about 10 µm, at most about 15 µm, at most about 20 µm, at most about 50 m, or at most about 100 µm. In some embodiments, the D50 value is in a range of from about 500 nm, about 1 µm, about 2 µm, about 3 µm, about 4 µm, or about 5 µm to about 8 µm, about 10 µm, about 15 µm, about 20 µm, or about 30 µm. In some embodiments, the D50 value is about 1 µm to about 20 µm, or any ranges therebetween.

In some embodiments, a herein described amorphous solid dispersion has a particle size distribution with a D90 value of about 200 nm to about 200 µm, or any ranges therebetween. In some embodiments, the D90 value is about 100 nm, about 500 nm, about 1 µm, about 5 µm, about 10 µm, about 15 µm, about 20 µm, about 25 µm, about 30 µm, about 40 jam, about 50 µm, about 60 µm, about 75 µm, about 100 µm, about 200 µm, or about 500 µm, In some embodiments, the D90 value is at least about 100 nm, at least about 500 nm, at least about 1 µm, at least about 5 µm, at least about 10 µm, at least about 15 µm, or at least about 20 µm. In some embodiments, the D90 value is at most about 500 nm, at most about 1 µm, at most about 5 µm, at most about 10 µm, at most about 15 µm, at most about 20 µm, at most about 50 µm, at most about 100 µm, at most about 200 µm, or at most about 500 am. In some embodiments, the D90 value is in a range of from about 500 nm, about 1 μm, about 2 pam, about 3 μm, about 4 μm, or about 5 μm to about 10 μm, about 15 μm, about 20 μm, or about 50 am. In some embodiments, the D90 value is about 1 μm to about 50 μm, or any ranges therebetween.

In some embodiments, a herein described amorphous solid dispersion has a glass transition temperature (Tg) higher than 20° C. In some embodiments, the amorphous solid dispersion has a Tg of at least 25° C., at least 30° C., at least 40° C., at least 50° C., at least 60° C., at least 70° C., at least 80° C., at least 90° C., or at least 100° C. In some embodiments, a herein described amorphous solid dispersion has a Tg of at least 50° C.

Active Pharmaceutical Ingredient (API)

Disclosed herein are amorphous solid dispersions and pharmaceutical compositions comprising an API. In some embodiments, the API has a limited or low solubility in water at neutral pH. In some embodiments, the API is lipophilic. In some embodiments, the API comprises a free base of the API, a salt of the API, a solvate of the API, or a combination thereof. In some embodiments, the API comprises at least partially protonated API. The protonated API is a salt resulting from the reaction of the free base API and an acid.

In some embodiments, the API is at least partially protonated. In some embodiments, an at least partially protonated API contains about 1% or more of pronated API. In some embodiments, an at least partially protonated API contains about 1%, about 2%, about 3%, about 4%, about 5%, about 6%, about 7%, about 8%, about 9%, about 10%, about 20%, about 30%, about 40%, about 50%, about 60%, about 70%, about 80%, about 90%, or more of pronated API. In some embodiments, the at least partially protonated API includes an API which is mono-protonated, di-protonated, or tri-protonated. In some embodiments, at least partially protonated API includes an API which is in an equilibrium among one or more of non-protonation, mono-protonation, di-protonation and tri-protonation states. In some embodiments, an at least partially protonated API includes an API which is in an equilibrium between non-protonation and mono-protonation states. In some embodiments, an at least partially protonated API comprises mono-protonated, di-protonated, and/or tri-protonated API.

Protonated API can refer to the cationic portion of a salt that is formed when an acid is added to a basic API. In some embodiments, a protonated API is mono-protonated, di-protonated, or tri-protonated. In some embodiments, a protonated API is in an equilibrium among one or more of non-protonation, mono-protonation, di-protonation and tri-protonation states. In some embodiments, a protonated API is in an equilibrium between non-protonation, mono-protonation, and di-protonation states. In some embodiments, a protonated API is in an equilibrium between non-protonation and mono-protonation states. In some embodiments, a protonated API comprises mono-protonated, di-protonated, and/or tri-protonated API.

In some embodiments, a protonated API is an API salt. In some embodiments, an API salt is monovalent or divalent. In some embodiments, an API salt is a mixture of a monovalent API salt and divalent API salt. In some embodiments, a monovalent salt is a salt in which the API cation or has a +1 charge. In instances wherein the API is singly protonated and has distinct conjugate acids, the salt is monovalent. For example, a salt of monoprotonated API "[HAPI]+" with substoichiometric amounts of conjugate acids tartrate $[C_4H_5O_6]^-$ and chloride $[Cl]^-$ is a monovalent salt $[HAPI][C_4H_5O_6]_{0.5}[Cl]_{0.5}$. Additional example $[HAPI][SO_4]_{0.5}$ is also a monovalent salt. In some embodiments, a divalent salt is a salt in which the cation has a +2 charge. Non limiting examples include an API salt which is doubly protonated and has a conjugate acid with a −2 charge (e.g. $[H_2API][SO_4]$). An additional example is an API salt which is doubly protonated and has two conjugate acids with a −1 charge $[H_2API][C_4H_5O_6][Cl]$. In some embodiments, a trivalent salt is a salt in which the API cation has a +3 charge and is triply protonated.

The acid dissociation constant ($K_a$) is a quantitative measure of the strength of an acid in solution. It is the equilibrium constant for a chemical reaction known as dissociation in the context of acid-base reactions. In aqueous solution, the equilibrium of acid dissociation can be written symbolically as:

where HA is a generic acid that dissociates into A−, known as the conjugate base of the acid and a hydrogen ion which combines with a water molecule to make a hydronium ion. The chemical species HA, H2O, A− and H3O+ are said to be in equilibrium when their concentrations (written below in square brackets) do not change with the passing of time. The dissociation constant is usually defined for a simplified reaction equation in which the solvent H2O is ignored:

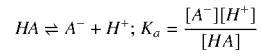

For many practical purposes it is more convenient to discuss the logarithmic constant, $pK_a$:

$pK_a = -\log_{10}(K_a)$

The more positive the value of $pK_a$, the smaller the extent of dissociation at any given pH that is, the weaker the acid.

In some embodiments, the protonated API is a weak acid, as determined by the $pK_a$ of the protonated API measured in water. In some embodiments, the protonated API is a weak acid, as determined by the calculated $pK_a$ of the protonated API. In some embodiments, the API has a $pK_a$ of about −2 to about 12, or any ranges therebetween. In some embodiments, the API has a pKa of about 1 to about 12. In some embodiments, the API has a pKa of about 3 to about 8. In some embodiments, the API has a $pK_a$ of about 1 to about 2, about 1 to about 3, about 1 to about 4, about 1 to about 5, about 1 to about 6, about 1 to about 7, about 1 to about 8, about 1 to about 9, about 1 to about 10, about 1 to about 11, about 1 to about 12, about 2 to about 3, about 2 to about 4, about 2 to about 5, about 2 to about 6, about 2 to about 7, about 2 to about 8, about 2 to about 9, about 2 to about 10, about 2 to about 11, about 2 to about 12, about 3 to about 4, about 3 to about 5, about 3 to about 6, about 3 to about 7, about 3 to about 8, about 3 to about 9, about 3 to about 10, about 3 to about 11, about 3 to about 12, about 4 to about 5, about 4 to about 6, about 4 to about 7, about 4 to about 8, about 4 to about 9, about 4 to about 10, about 4 to about 11, about 4 to about 12, about 5 to about 6, about 5 to about 7, about 5 to about 8, about 5 to about 9, about 5 to about 10, about 5 to about 11, about 5 to about 12, about 6 to about 7, about 6 to about 8, about 6 to about 9, about 6 to about 10, about 6 to about 11, about 6 to about 12, about 7 to about 8, about 7 to about 9, about 7 to about 10, about 7 to about 11, about 7 to about 12, about 8 to about 9, about 8 to about 10, about 8 to about 11, about 8 to about 12, about 9 to about 10, about 9 to about 11, or about 9 to about 12. In some embodiments, the API has a $pK_a$ of at least about −2, at least about −1, at least about 0, at least about 1, at least about 2, at least about 3, at least about 4, at least about 5, at least about 6, at least about 7, at least about 8, at least about 9, or at least about 10. In some embodiments, the API has a $pK_a$ of at most about 12, at most about 11, at most about 10, at most about 9, at most about 8, at most about 7, at most about 6, at most about 5, at most about 4, or at most about 3.

Exemplary small molecule APIs with calculated $pK_a$ of about −2 to about 12, include, without limitation, those APIs listed in Table A. Techniques for measuring the $pK_a$ of the APIs in Table A are known in the art, such as those described in Babic, S.; Horvat, J. M; Pavlovic, D. M; Kastelan-Macan, M; Trends in Anal. Chem.; 26, 11, 2007. For example, the pKa values of the APIs can be determined by potentiometric titration, by spectrophotometric methods, by NMR titration, by liquid chromatography, by capillary electrophoresis (CE), or by computational methods. In some embodiments, analysis methods used to derive pKa values from titration curves in a potentiometric titration include Grans plot, second-derivative ($\Delta^2 pH/\Delta V^2$), and least-squares non-linear regression.

TABLE A

Exemplary small molecule APIs

| Name | Measured or Calculated $pK_a$s |
|---|---|
| Sulfacetamide | 1.95 ± 0.11; 5.30 ± 0.05 |
| Sulfachloropyridazine | 1.87 ± 0.30; 5.45 ± 0.06 |
| Sulfadiazine | 2.10; 6.28 |
| Sulfadimethoxine | 2.13 ± 0.30; 6.08 ± 0.09 |
| Sulfaguanidine | 1.55; 11.24 |
| Sulfamerazine | 2.17; 6.77 |
| Sulfamethazine | 2.28; 7.42 |
| Sulfamethizole | 1.86 ± 0.30; 5.29 ± 0.04 |
| Sulfamethoxazole | 1.83; 5.57 |
| Sulfathiazole | 2.08; 7.07 |
| Chlortetracycline | 3.33 ± 0.30; 7.55 ± 0.02 |
| Demeclocycline | 3.37 ± 0.30; 7.36 ± 0.03 |
| Doxycycline | 3.02 ± 0.30; 7.97 ± 0.15 |
| Meclocycline | 4.05 ± 0.30; 6.87 ± 0.39 |
| Oxytetracycline | 3.04; 8.00 |
| Tetracycline | 3.32 ± 0.30; 7.78 ± 0.05; 9.58 ± 0.30 |
| Ciprofloxacin | 5.86 ± 0.05; 8.24 ± 0.07 |
| Danofloxacin | 6.07 ± 0.06; 8.56 ± 0.07 |
| Difloxacin | 5.66 ± 0.04; 7.24 ± 0.06 |
| Enoxacin | 5.05 ± 0.08; 6.25 ± 0.05 |
| Enrofloxacin | 5.88 ± 0.03; 7.74 ± 0.03 |
| Fleroxacin | 5.46; 8.00 |
| Flumequine | 6.35 ± 0.01 |
| Lomefloxacin | 5.00 ± 0.10; 6.25 ± 0.05; 9.00 ± 0.03 |
| Marbofloxacin | 5.69 ± 0.10; 8.02 ± 0.20 |
| Nalidixic acid | 6.01 ± 0.05 |
| Norfloxacine | 5.94 ± 0.05; 8.22 ± 0.07 |
| Pefloxacin | 6.21 ± 0.12; 7.87 ± 0.10 |
| Pipemidic acid | 5.42 ± 0.05; 8.18 ± 0.09 |
| Ofloxacin | 6.22 ± 0.05; 7.81 ± 0.08 |
| Sarafloxacin | 5.62 ± 0.08; 8.18 ± 0.09 |
| Azithromycin | 7.34 |
| Clarithromycin | 7.25 |
| Erythromycin | 8.90 ± 0.15 |
| Roxithromycin | 9.17 ± 0.30 |
| Tylosin | 3.31 ± 0.30; 7.50 ± 0.13 |
| Amoxicillin | 3.39, 6.71; 9.41 |
| Ampicillin | 2.55 ± 0.01; 7.14 ± 0.01 |
| Penicillin G | 3.42 |
| Acebutolol | 9.21 |
| Alprenolol | 9.38 ± 0.1 |
| Atenolol | 9.48 ± 0.01 |
| Labetalol | 7.35 |
| Metoprolol | 9.44 ± 0.1 |
| Omeprazole | 4.14; 8.90 |
| Oxprenolol | 9.62 |
| Pindolol | 9.16 |

TABLE A-continued

Exemplary small molecule APIs

| Name | Measured or Calculated $pK_a$s |
|---|---|
| Practolol | 9.41 |
| Propranolol | 9.49 ± 0.2 |
| Sotalol | 9.01 |
| Timolol | 9.34 |
| Butibufen | 4.64 |
| Carprofen | 4.63 |
| Diclofenac | 4.16 |
| Fenbufen | 4.56 |
| Flurbiprofen | 4.35 |
| Ibuprofen | 4.51 |
| Ketoprofen | 4.36 |
| Naproxen | 4.38 ± 0.03 |
| Piperazine | 5.33; 9.73 |
| Procaine | 2.28 ± 0.08; 9.02 ± 0.01 |
| Trimethoprim | 3.23 ± 0.30; 6.76 ± 0.12 |
| Gefitinib | 7.2 |
| Erlotinib | 5.4 |

The partition-coefficient (P) as referenced herein is a ratio of concentrations of a compound between two immiscible solvent phases at equilibrium. Most commonly, one of the solvents is water and the other is hydrophobic, typically 1-octanol. The logarithm of the ratio is log P, as shown below (conventionally the lipophilic phase is the numerator and hydrophilic phase is the denominator). Accordingly, log P is a measure of lipophilicity or hydrophobicity.

$$\log P_{octanol/water} = \log\left(\frac{[solute]_{octanol}}{[solute]_{water}}\right)$$

In some embodiments, the API is lipophilic. In some embodiments, the API free base is lipophilic. In some embodiments, the API has a log P of at least about 1, at least about 2, at least about 3, at least about 4, or at least about 5 in a free base or unprotonated form. In some embodiments, a ratio of a solubility of the protonated API to a solubility of the API as a free base is at least 1.5:1, at least 2:1, at least 3:1, at least 5:1, at least 10:1, at least 20:1, at least 50:1, at least 100:1 or at least 200:1 in water. In some embodiments, a ratio of a solubility of the protonated API to a solubility of the API as a free base is at least 10:1.

In some embodiments, the API has a low solubility at a pH of about 6-8. In some embodiments, the API has a solubility of less than 10 mg/ml, less than 1.0 mg/ml, less than 0.5 mg/ml, less than 0.1 mg/ml, less than 0.05 mg/ml, less than 0.04 mg/ml, less than 0.03 mg/ml, less than 0.02 mg/ml, less than 0.01 mg/ml, less than 0.002 mg/ml, or less than 0.001 mg/ml in an aqueous solution with a pH of between about 6-8. In some embodiments, the API has a higher solubility at a pH lower than 6. In some embodiments, the API has a solubility of at least 0.02 mg/ml, at least 0.05 mg/ml, at least 0.1 mg/ml, at least 0.2 mg/ml, at least 0.5 mg/ml, at least 0.7 mg/ml, at least 1 mg/ml, at least 5 mg/ml, or at least 10 mg/ml in an aqueous solution with a pH lower than 6.

In some embodiments, the API has a low solubility at a pH of 5 or higher. In some embodiments, the API has a solubility of less than 10 mg/ml, less than 1.0 mg/ml, less than 0.5 mg/ml, less than 0.1 mg/ml, less than 0.05 mg/ml, less than 0.04 mg/ml, less than 0.03 mg/ml, less than 0.02 mg/ml, less than 0.01 mg/ml, or less than 0.001 mg/ml in an aqueous solution with a pH of 5 or higher. In some embodiments, the API has a higher solubility at a pH of 4 or lower. In some embodiments, the API has a solubility of at least 0.02 mg/ml, at least 0.05 mg/ml, at least 0.1 mg/ml, at least 0.2 mg/ml, at least 0.5 mg/ml, at least 0.7 mg/ml, at least 1 mg/ml, at least 5 mg/ml, or at least 10 mg/ml in an aqueous solution with a pH of 4 or lower.

In one aspect, described herein is an amorphous solid dispersion that comprises: (a) an active pharmaceutical ingredient (API), wherein the API comprises a compound of Formula (I),

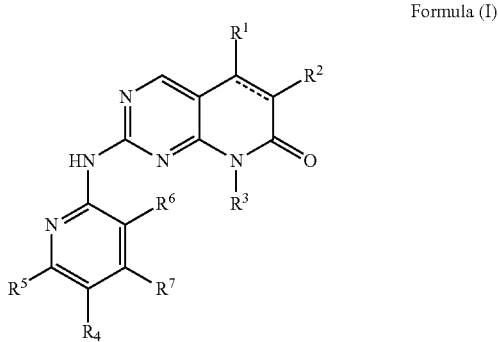

Formula (I)

wherein,
═══════ represents a single bond or a double bond;
$R^1$ is $C_1$-$C_6$ alkyl;
$R^3$ is $C_1$-$C_8$ alkoxy, $C_3$-$C_7$ cycloalkyl, or $C_3$-$C_7$-heterocyclyl;
$R^2$ and $R^4$ are each independently selected from hydrogen, halogen, $C_1$-$C_8$ alkyl, $C_3$-$C_7$ cycloalkyl, $C_3$-$C_7$ heterocycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^{10}$, $SR^{10}$, $NR^{10}R^{11}$, $N(O)R^{10}R^{11}$, $P(O)(OR^{10})(OR^{11})$, $(CR^{10}R^{11})_m NR^{12}R^{13}$, $COR^{10}$, $(CR^{10}R^{11})_m C(O)R^{12}$, $CO_2R^{10}$, $CONR^{10}R^{11}$, $C(O)NR^{10}SO_2R^{11}$, $NR^{10}SO_2R^{11}$, $C(O)NR^{10}R^{11}$, $S(O)_n R^{10}$, $SO_2NR^{10}R^{11}$, $P(O)(OR^{10})(OR^{11})$, $(CR^{10}R^{11})_m P(O)(OR^{12})(OR^{13})$, $(CR^{10}R^{11})_m$-aryl, $(CR^{10}R^{11})_m$-heteroaryl, and $CR^{10}$═$CR^1C(O)R^{12}$;
each of $R^5$, $R^6$, and $R^7$ is independently hydrogen, halogen, $C_1$-$C_6$ alkyl, $C_1$-$C_6$ haloalkyl, $C_1$-$C_8$ alkoxy, $C_1$-$C_8$ alkoxyalkyl, CN, $NO_2$, $OR^{10}$, $NR^{10}R^{11}$, $CO_2R^{10}$, $COR^{10}$, $S(O)_n R^{10}$, $CONR^{10}R^{11}$, $NR^{10}COR^{11}$, $NR^{10}SO_2R^{11}$, $SO_2NR^{10}R^{11}$, or $P(O)(OR^{10})(OR^{11})$;
each of $R^{10}$, $R^{11}$, $R^{12}$ and $R^{13}$ is independently hydrogen, $C_1$-$C_8$ alkyl, $C_2$-$C_8$ alkenyl, $C_2$-$C_8$ alkynyl, arylalkyl, cycloalkyl, heterocycloalkyl, aryl, or heteroaryl;
m is 0, 1, 2, 3, 4, 5, or 6; and
n is 0, 1 or 2;
and wherein the API is at least partially protonated;
(b) a first acid, wherein the first acid is an organic acid that has a pKa of at most 2; (c) a second acid, wherein the second acid has a pKa greater than 2; and (d) a hydrophilic high-molecular weight material, wherein a molar ratio of the second acid to the first acid is from about 0.2:1 to about 20:1. In some embodiments, the amorphous solid dispersion further comprises and optional adsorbent.

In one aspect, described herein is an amorphous solid dispersion that comprises: (a) an active pharmaceutical ingredient (API) or a pharmaceutically acceptable salt or solvate thereof, wherein the API comprises a compound of Formula (I); (b) a surfactant, wherein the surfactant is selected from polymeric non-ionic surfactants and phospholipids; (c) a non-ionic hydrophilic polymer; and (d) optionally an adsorbent. In some embodiments, the API, or a salt or solvate thereof, comprises about 5% to about 70% of a total weight of the amorphous solid dispersion. In some embodiments, the surfactant is a polymeric non-ionic surfactant. In some embodiments, the polymeric non-ionic surfactant comprises a block copolymer of polyethylene glycol and polypropylene glycol. In some embodiments, the polymeric non-ionic surfactant is Poloxamer 188. In some embodiments, the surfactant comprises one or more phospholipids. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the surfactant comprises lecithin. In some embodiments, the surfactant comprises about 5% to about 70% of a total weight of the amorphous solid dispersion. In some embodiments, a weight ratio of the API or a salt or solvate thereof to the surfactant is from about 10:1 to about 1:10.

In some embodiments, wherein the API comprises a compound of Formula (I) or a pharmaceutically acceptable salt thereof, ═══════ represents a double bond. In some embodiments, each of $R^5$, $R^6$, and $R^7$ is independently hydrogen, halogen, or $C_1$-$C_6$ alkyl. In some embodiments, each of $R^5$, $R^6$, and $R^7$ is hydrogen. In some embodiments, $R^1$ is methyl. In some embodiments, $R^2$ is hydrogen, halogen, $C_1$-$C_8$ alkyl, $C_3$-$C_7$ cycloalkyl, $C_3$-$C_7$ heterocycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $COR^{10}$ or $OR^{10}$. In some embodiments, $R^2$ is $C_3$-$C_7$ cycloalkyl. In some embodiments, $R^2$ is $COR^{10}$. In some embodiments, $R^2$ is $(CO)CH_3$. In some embodiments, $R^3$ is $C_3$-$C_7$ cycloalkyl. In some embodiments, $R^3$ is cyclopentyl. In some embodiments, $R^4$ is hydrogen, halogen, $C_1$-$C_8$ alkyl, $C_3$-$C_7$ cycloalkyl, $C_3$-$C_7$ heterocycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, or $OR^{10}$. In some embodiments, $R^4$ is $C_3$-$C_7$ cycloalkyl. In some embodiments, $R^4$ is $C_3$-$C_7$ heterocycloalkyl. In some embodiments, $R^4$ is 6-membered heterocycloalkyl containing 1 or 2 ring nitrogen atoms. In some embodiments, $R^4$ is piperazin-1-yl. In some embodiments, each of $R^{10}$, $R^{11}$, $R^{12}$ and $R^{13}$ is independently hydrogen or $C_1$-$C_8$ alkyl. In some embodiments, each of $R^{10}$, $R^{11}$, $R^{12}$ and $R^{13}$ is independently hydrogen or methyl.

In some embodiments, the API of Formula (I) is at least partially protonated. In some embodiments, the API of Formula (I) is palbociclib or a salt or solvate thereof.

Palbociclib is a selective inhibitor of CDK4/6 and its chemical name is 6-acetyl-8-cycic-5-methyl-2-[[5-(piperazine-1-based) pyridine-2-base]-8H-pyridine and [2, pyrimidine+ketone, belonging to the category of pyridine and pyrimidine. The IC50 (the concentration when the tumor cells account for 50% of total cells) of selective inhibitor CDK4 and CDK6 is 11 nmol/L and 15 nmol/L, respectively, while the IC50 of CDK2, CDK1, and CDK5 was more than 10 nmol/L.

In some embodiments, a pharmaceutical composition and/or an amorphous solid dispersion provided herein comprises an API that is palbociclib. Conjugate acids of palbociclib have a $pK_a$ of 3.9 and 7.4 in water. In some embodiments, the protonated API is protonated palbociclib. In some embodiments, the API comprises monoprotonated palbociclib. In some embodiments, the API comprises diprotonated palbociclib. In some embodiments, the API comprises palbociclib free base, monoprotonated palbociclib, diprotonated palbociclib, or any combination thereof. In some embodiments, the API comprises monoprotonated palbociclib, diprotonated palbociclib, or both. In some embodiments, the API comprises palbociclib free base, monoprotonated palbociclib, and/or diprotonated palbociclib, in an equilibrium state. In some embodiments, the API comprises palbociclib free base and monoprotonated palbociclib, in an equilibrium state. In some embodiments, the palbociclib is protonated on the secondary piperazine nitrogen. In some embodiments, the palbociclib is protonated on the pyridine nitrogen, the secondary piperazine nitrogen, or both.

In one aspect, described herein is an amorphous solid dispersion that comprises: a) an active pharmaceutical ingredient (API), wherein the API comprises a compound of Formula (II),

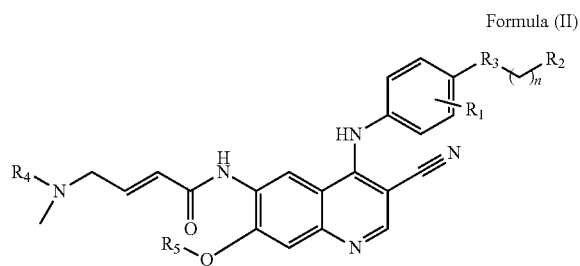

Formula (II)

or a pharmaceutically acceptable salt thereof,
wherein,
$R_1$ is halogen;
$R_2$ is a pyridinyl, thiophene, pyrimidine, thiazole, or phenyl optionally substituted with up to three substituents;
$R_3$ is —O— or —S—;
$R_4$ is $C_{1-3}$ alkyl or $C_{1-3}$ heteroalkyl;
$R^5$ is ethyl or methyl;
n is 0 or 1;
b) one or more acids; and
c) a hydrophilic high-molecular weight material.

In some embodiments, wherein the API comprises a compound of Formula (II) or a pharmaceutically acceptable salt thereof, $R_1$ is chlorine. In some embodiments, $R_2$ is pyridinyl. In some embodiments, $R_3$ is —O—. In some embodiments, $R_4$ is methyl. In some embodiments, $R_5$ is ethyl. In some embodiments, n is 1. In some embodiments, wherein the compound of Formula (II) is a maleate salt.

In some embodiments, the API of Formula (I) is at least partially protonated. In some embodiments, the API of Formula (II) is neratinib or a salt or solvate thereof.

In one aspect, described herein is an amorphous solid dispersion that comprises: (a) an active pharmaceutical ingredient (API) or a pharmaceutically acceptable salt or solvate thereof, wherein the API comprises a compound of Formula (II); (b) a surfactant, wherein the surfactant is selected from polymeric non-ionic surfactants and phospholipids; (c) a non-ionic hydrophilic polymer; and (d) optionally an adsorbent.

Neratinib is a kinase inhibitor indicated for the extended adjuvant treatment of adult patients with early stage HER2-overexpressed/amplified breast cancer, to follow adjuvant trastuzumab-based therapy. Neratinib is a member of the 4-anilino quinolidine class of protein kinase inhibitors. The molecular formula for neratinib maleate is $C_{30}H_{29}ClN_6O_3 \cdot C_4H_4O_4$ and the molecular weight is 673.11 Daltons. The chemical name is (E)-N-{4-[3-chloro-4-(pyridin-2-yl methoxy)anilino]-3-cyano-7-ethoxyquinolin-6-yl}-4-(dimethylamino)but-2-enamide maleate. Neratinib is a kinase inhibitor that irreversibly binds to Epidermal Growth Factor Receptor (EGFR), Human Epidermal Growth Factor Receptor 2 (HER2), and HER4. In vitro, neratinib reduces EGFR and HER2 autophosphorylation, downstream MAPK and AKT signaling pathways, and showed antitumor activity in EGFR and/or HER2 expressing carcinoma cell lines. Neratinib human metabolites M3, M6, M7 and M11 inhibited the activity of EGFR, HER2 and HER4 in vitro. In vivo, oral administration of neratinib inhibited tumor growth in mouse xenograft models with tumor cell lines expressing HER2 and EGFR.

In some embodiments, a pharmaceutical composition and/or an amorphous solid dispersion provided herein comprises an API that is neratinib. Conjugate acids of neratinib, such as neratinib maleate, have a $pK_a$ of 4.66 and 7.65 in water. In some embodiments, the protonated API is protonated neratinib. In some embodiments, the API comprises monoprotonated neratinib. In some embodiments, the API comprises diprotonated neratinib. In some embodiments, the API comprises neratinib free base, monoprotonated neratinib, diprotonated neratinib, or any combination thereof. In some embodiments, the API comprises monoprotonated neratinib, diprotonated neratinib, or both. In some embodiments, the API comprises neratinib free base, monoprotonated neratinib, and/or diprotonated neratinib, in an equilibrium state. In some embodiments, the API comprises neratinib free base and monoprotonated neratinib, in an equilibrium state.

In some embodiments, a described amorphous solid dispersion comprises an API that is at least partially protonated. In some embodiments, the amorphous solid dispersion comprises a protonated API, an anion of an organic or an inorganic acid, and a high-molecular weight material. In some embodiments, a described amorphous solid dispersion comprises a salt of the API, wherein the cation of the salt is the protonated API. In some embodiments, the salt of the API is a reaction product of the API free base (or a salt thereof) with an acid. In some embodiments, the amorphous solid dispersion comprises a salt of the API, wherein the salt is formed in situ. In some embodiments, the amorphous solid dispersion comprises a salt of palbociclib, wherein the salt is a reaction product of palbociclib free base with an acid. In some embodiments, the at least partially protonated API is a reaction product of a first acid with a freebase of the API. In some embodiments, the API comprises at least partially protonated palbociclib. In some embodiments, the partially protonated palbociclib is a reaction product of a first acid with palbociclib free base or a salt thereof. In some embodiments, the amorphous solid dispersion comprises a mesylate salt of the API such as palbociclib mesylate. In some embodiments, the mesylate salt of the API (e.g., palbociclib mesylate) is formed in situ. In some embodiments, the amorphous solid dispersion comprises a salt of neratinib, wherein the salt is a reaction product of neratinib free base with an acid. In some embodiments, the at least partially protonated API is a reaction product of a first acid with a freebase of the API. In some embodiments, the API comprises at least partially protonated neratinib. In some embodiments, the partially protonated neratinib is a reaction product of a first acid with neratinib free base or a salt thereof. In some embodiments, the amorphous solid dispersion comprises a maleate salt of the API such as neratinib maleate. In some embodiments, the maleate salt of the API (e.g., neratinib maleate) is formed in situ.

In some embodiments, an amorphous solid dispersion comprises the free base of an API, a first acid, a second acid, and a hydrophilic-high molecular weight polymer. Such amorphous solid dispersions are interchangeable with an amorphous solid dispersion comprising an acidic salt of an API, a second acid, and a hydrophilic-high molecular weight polymer, wherein the acidic salt of the API is formed from the reaction of the free base API and the first acid. In some embodiments, the acidic salt of the API is generated in situ. In some embodiments, the acidic salt of the API is in the solid state and is dissolved during the formation of the amorphous solid dispersion.

An amorphous solid dispersion disclosed herein can comprise a salt of an API. In some embodiments, an amorphous solid dispersion comprises at least partially protonated API that comprises a cation present in a pharmaceutically acceptable salt. Pharmaceutically acceptable salts include, but are not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like. Pharmaceutically acceptable salts further include, without limitation, bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafuorobutyrate), bis(pentaflu oropropionate), bis(pyridine carboxylate), bis(trifluoroacetate), chlorhydrate, and sulfate pentahydrate. Other representative pharmaceutically acceptable salts include, e.g., water-soluble and water-insoluble salts, such as the acetate, amsonate(4,4-diaminostilbene-2, 2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. In some embodiments, the salt of the API can be formed by reacting the API free base with an acid, such as an acid described in the present disclosure. In some embodiments the API is palbociclib or a pharmaceutically acceptable salt thereof. In some embodiments the API is neratinib or a pharmaceutically acceptable salt thereof, such as neratinib maleate. In some embodiments, the API is one listed in Table A, or a pharmaceutically acceptable salt thereof.

In some embodiments, a pharmaceutical composition and/or an amorphous solid dispersion provided herein comprises an API (such as palbociclib or neratinib) in an amount of 10 mg to 1000 mg. In some embodiments, the API is present in an amount of 20 mg to 500 mg. In some embodiments, the API is present in an amount of 25 mg to 250 mg. In some embodiments, the API is present in an amount of about 50 mg, about 100 mg or about 125 mg. In some embodiments, a pharmaceutical composition and/or an amorphous solid dispersion provided herein comprises an API (such as palbociclib or neratinib) in an amount of from about 1 mg to about 500 mg, from about 10 mg to about 400 mg, from about 10 mg to about 250 mg, from about 5 mg to about 250 mg, from about 25 mg to about 250 mg, from about 25 mg to about 200 mg, from about 50 mg to about 200 mg, from about 50 mg to about 150 mg, from about 75 mg to about 150 mg, from about 100 mg to about 150 mg, from about 125 mg to about 150 mg, from about 75 mg to about 125 mg, from about 100 mg to about 125 mg, from about 75 mg to about 125 mg, from about 50 mg to about 125 mg, from about 25 mg to about 125 mg, from about 75 mg to about 100 mg, from about 50 mg to about 100 mg, from about 25 mg to about 100 mg, from about 5 mg to about 100 mg, from about 50 mg to about 75 mg, from about 25 mg to about 75 mg, from about 5 mg to about 75 mg, from about 50 mg to about 55 mg, from about 5 mg to about 25 mg, from about 10 mg to about 25 mg, from about 5 mg to about 50 mg, from about 10 mg to about 50 mg, or from about 25 mg to about 50 mg, or any ranges therebetween. In some embodiments, a pharmaceutical composition and/or an amorphous solid dispersion is provided that comprises an API in an amount of at least 10 mg, at least 20 mg, at least 25 mg, at least 30 mg, at least 40 mg, at least 50 mg, at least 60 mg, at least 70 mg, at least 75 mg, at least 80 mg, at least 90 mg, at least 100 mg, at least 110 mg, at least 120 mg, at least 125 mg, at least 130 mg, at least 140 mg, at least 150 mg, at least 160 mg, at least 170 mg, at least 175 mg, at least 180 mg, at least 190 mg, or at least 200 mg. In some embodiments, a pharmaceutical composition described herein comprises an API in an amount of from about 5 mg to about 200 mg. In some embodiments, a pharmaceutical composition and/or an amorphous solid dispersion is provided that comprises an API in an amount of at most 1000 mg. In some embodiments, the API is present in an amount of at most 750 mg, at most 500 mg, at most 400 mg, at most 300 mg, at most 250 mg, at most 225 mg, at most 200 mg, at most 175 mg, at most 150 mg, at most 125 mg, at most 100 mg, at most 90 mg, at most 80 mg, at most 75 mg, at most 60 mg, at most 55 mg, at most 50 mg, at most 25 mg, or at most 10 mg. In some embodiments, the API is in a free base form. In some embodiments, the API is protonated or partially protonated. In some embodiments, the API is in a salt or solvate form. In some embodiments the API is palbociclib or a pharmaceutically acceptable salt or solvate thereof. In some embodiments the API is neratinib or a pharmaceutically acceptable salt thereof, such as neratinib maleate. In some embodiments, the API is one listed in Table A, or a pharmaceutically acceptable salt or solvate thereof.

In some embodiments, a pharmaceutical composition and/or an amorphous solid dispersion provided herein comprises an API (such as palbociclib or neratinib) that is present in an amount of from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In some embodiments, the API is in a free base form. In some embodiments, the API is protonated or partially protonated. In some embodiments, the API is in a salt or solvate form. In some embodiments, the API is one listed in Table A, or a pharmaceutically acceptable salt or solvate thereof.

In some embodiments, a pharmaceutical composition and/or an amorphous solid dispersion provided herein comprises palbociclib. In some embodiments, a pharmaceutical composition described herein comprises palbociclib or a salt or solvate thereof in an amount of equivalent to 50 mg of palbociclib free base. In some embodiments, a pharmaceutical composition described herein comprises palbociclib or a salt or solvate thereof in an amount of equivalent to 75 mg of palbociclib free base. In some embodiments, a pharmaceutical composition described herein comprises palbociclib or a salt or solvate thereof in an amount of equivalent to 100 mg of palbociclib free base. In some embodiments, a pharmaceutical composition described herein comprises palbociclib or a salt or solvate thereof in an amount of equivalent to 125 mg of palbociclib free base. In some embodiments, a pharmaceutical composition described herein comprises palbociclib or a salt or solvate thereof in an amount of equivalent to about 75 to about 125 mg of palbociclib free base. In some embodiments, a pharmaceutical composition described herein comprises palbociclib or a salt or solvate thereof in an amount of equivalent to about 25 to about 500 mg of palbociclib free base, or any ranges therebetween. In some embodiments, the palbociclib is at least partially protonated. In some embodiments, the pharmaceutical composition comprises palbociclib acetate, palbociclib chloride, palbociclib tartrate, palbociclib mesylate, or a combination thereof. In some embodiments, the pharmaceutical composition comprises palbociclib tartrate, palbociclib mesylate, or both.

In some embodiments, a pharmaceutical composition and/or an amorphous solid dispersion provided herein comprises neratinib. In some embodiments, a pharmaceutical composition described herein comprises neratinib or a salt or solvate thereof in an amount of equivalent to 20 mg of neratinib free base. In some embodiments, a pharmaceutical composition described herein comprises neratinib or a salt or solvate thereof in an amount of equivalent to 40 mg of neratinib free base. In some embodiments, a pharmaceutical composition described herein comprises neratinib or a salt or solvate thereof in an amount of equivalent to 60 mg of neratinib free base. In some embodiments, a pharmaceutical composition described herein comprises neratinib or a salt or solvate thereof in an amount of equivalent to 100 mg of neratinib free base. In some embodiments, a pharmaceutical composition described herein comprises neratinib or a salt or solvate thereof in an amount of equivalent to about 20 to about 100 mg of neratinib free base. In some embodiments, a pharmaceutical composition described herein comprises neratinib or a salt or solvate thereof in an amount of equivalent to about 30 to about 50 mg of neratinib free base, or any ranges therebetween. In some embodiments, the neratinib is at least partially protonated. In some embodiments, the pharmaceutical composition comprises neratinib maleate, neratinib malate, neratinib tartrate, neratinib mesylate, or a combination thereof. In some embodiments, the pharmaceutical composition comprises neratinib maleate, neratinib mesylate, or both.

In some embodiments, a pharmaceutical composition and/or an amorphous solid dispersion provided herein comprises an API (such as palbociclib or neratinib) in an amount of about 5%, about 10%, about 15%, about 20%, about 25%, about 30%, about 40%, about 50%, about 60%, or about 70% of the total weight of the composition. In some embodiments, a pharmaceutical composition and/or an amorphous solid dispersion provided herein comprises an API (such as palbociclib or neratinib) in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the total weight of the composition. In some embodiments, a pharmaceutical composition and/or an amorphous solid dispersion provided herein comprises an API (such as palbociclib or neratinib) in an amount of from about 0.1% to about 99%, from about 0.1% to about 80%, about 0.1% to about 60%, from about 0.10% to about 40%, from about 0.10% to about 20%, from about 0.10% to about 10%, from about 0.1% to about 1%, from about 20% to about 99%, from about 20% to about 80%, from about 20% to about 60%, from about 20% to about 40%, from about 25% to about 45%, from about 25% to about 50%, from about 25% to about 60%, from about 25% to about 75%, from about 30% to about 99%, from about 30% to about 80%, from about 30% to about 60%, from about 30% to about 50%, from about 30% to about 40%, from about 40% to about 99%, from about 40% to about 80%, from about 40% to about 60%, from about 40% to about 50%, or from about 40% to about 45% of the total weight of the composition. In some embodiments, the API is in a free base form. In some embodiments, the API is protonated or partially protonated. In some embodiments, the API is in a salt or solvate form. In some embodiments the API is palbociclib or a pharmaceutically acceptable salt or solvate thereof. In some embodiments the API is neratinib or a pharmaceutically acceptable salt thereof, such as neratinib maleate. In some embodiments, the API is one listed in Table A, or a pharmaceutically acceptable salt or solvate thereof.

Acids

In one aspect, described herein is an amorphous solid dispersion comprising an API and one or more acids. Also described herein is a pharmaceutical composition comprising an API and one or more acids. In some embodiments, the amorphous solid dispersion comprises an API, one or more acids, and a hydrophilic high-molecular weight material. In some embodiments, the amorphous solid dispersion comprises an API, a first acid, a second acid, and a hydrophilic high-molecular weight material. In some embodiments, the API is at least partially protonated.

In some embodiments, an amorphous solid dispersion and/or a pharmaceutical composition disclosed herein comprises one or more organic acids. In some embodiments, the organic acid has a pKa smaller than 1. In some embodiments, the organic acid has a pKa that is at most 2. In some embodiments, the organic acid has a pKa that is at most 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4.0, or 5.0. In some embodiments, the organic acid is completely ionized. In some embodiments, the organic acid is partially ionized. In some embodiments, the one or more organic acids comprise one or more of acetic acid, acrylic acid, adipic acid, alginic acid, amino acids, ascorbic acid, benzoic acid, benzenesulfonic acid, butyric acid, carbonic acid, citric acid, formic acid, fumaric acid, gluconic acid, isoascorbic acid, lactic acid, maleic acid, malic acid, methanesulfonic acid, fluorinated acids, trifluoromethanesulfonic acid, trifluoroacetic acid, oxalic acid, propionic acid, salicylic acid, stearic acid, succinic acid, tannic acid, tartaric acid, thioglycolic acid, aliphatic sulfonic acids (e.g., methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid), aromatic sulfonic acids (e.g., benzenesulfonic acid, tolylsulfonic acid, or naphthalenesulfonic acid) and uric acid. In some embodiments, the one or more organic acids comprise methanesulfonic acid, tartaric acid, or both. In some embodiments, the one or more organic acids comprise methanesulfonic acid and tartaric acid. In some embodiments, the one or more organic acids excludes acetic acid.

In some embodiments, the amorphous solid dispersion comprises an API, one or more acids, and a hydrophilic high-molecular weight material. In some embodiments, one or more acids comprises a first acid with a pKa of at most 2 and a second acid with a pKa of greater than 2. In some embodiments, the first acid is an organic acid. In some embodiments, the first acid is oxalic acid, maleic acid, trichloroacetic acid, dichloroacetic acid, trifluoroacetic acid, an aliphatic sulfonic acid, or an aromatic sulfonic acid. In some embodiments, the aliphatic sulfonic acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid. In some embodiments, the aromatic sulfonic acid is benzenesulfonic acid, tolylsulfonic acid, or naphthalenesulfonic acid. In some embodiments, the first acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid. In some embodiments, the second acid is tartaric acid, fumaric acid, succinic acid, citric acid, lactic acid, malic acid, or acetic acid.

In some embodiments, the one or more organic acids are present in the amorphous solid dispersion and/or in the pharmaceutical composition in an amount of from about 0.10% to about 99% by weight of the total composition. In some embodiments, the one or more organic acids are present in the amorphous solid dispersion and/or in the pharmaceutical composition in an amount of from about 1% to about 80%, from about 1% to about 60%, from about 1% to about 50%, from about 1% to about 25%, from about 1% to about 10%, from about 1% to about 5%, from about 10% to about 80%, from about 10% to about 60%, from about 10% to about 50%, from about 20% to about 80%, from about 20% to about 60%, from about 20% to about 50%, from about 30% to about 80%, from about 30% to about 60%, from about 30% to about 50%, or from about 30% to about 40% by weight of the total composition. In some embodiments, the one or more organic acids are present in the amorphous solid dispersion and/or in the pharmaceutical composition in an amount of about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45% by weight of the total composition. In some embodiments, the one or more organic acids comprise tartaric acid. In some embodiments, the one or more organic acids comprise methanesulfonic acid. In some embodiments, the one or more organic acids are present in the amorphous solid dispersion and/or in the pharmaceutical composition in an amount of about 1.0 mg to about 1000 mg, including but not limited to about 5.0 mg, 10.0 mg, 15.0 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, or 350 mg. In some embodiments, the one or more organic acids are present in the amorphous solid dispersion and/or in the pharmaceutical composition in an amount of 1 mg to 500 mg. In some embodiments, the one or more organic acids are present in an amount of from about from about 10 mg to about 400 mg, 20 mg to about 300 mg, from about 25 mg to about 200 mg, from about 50 mg to about 150 mg, from about 75 mg to about 125 mg, from about 75 mg to about 100 mg, from about 100 mg to about 125 mg, from about 1 mg to about 200 mg, or from about 50 mg to about 200 mg. In some embodiments, the one or more organic acids are present in an amount of 25 mg to 250 mg. In some embodiments, the one or more organic acids are present in an amount of 150 mg to 250 mg. In some embodiments, the one or more organic acids are present in an amount of 150 mg to 200 mg. In some embodiments, the one or more organic acids are present in an amount of 50 mg to 200 mg.

In some embodiments, the one or more organic acids are present in a molar ratio to the API of greater than 0.5:1, greater than 1:1, greater than 1.5:1, greater than 2:1, greater than 2.5:1, or greater than 3:1. In some embodiments, the one or more organic acids are present in a molar ratio to the API of about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the one or more organic acids comprise tartaric acid and methanesulfonic acid.

In some embodiments, an amorphous solid dispersion described herein comprises an API, one or more acids, and a hydrophilic high-molecular weight material. In some embodiments, one or more acids comprises a first acid with a pKa of at most 2 and a second acid with a pKa of greater than 2. In some embodiments, the molar ratio of the first acid to API is present in a molar ratio to the API of about 0.1:1 to about 10:1, about 0.5:1 to about 5:1, about 0.5:1 to about 3:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the molar ratio of the second acid to API is present in a molar ratio to the API of about 0.1:1 to about 10:1, about 1:1 to about 8:1, about 2:1 to about 7:1, about 4:1 to about 7:1, about 0.5:1 to about 3:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1. In some embodiments, the mass ratio of the second acid to API is present in a mass ratio to the API of about 0.1:1 to about 10:1, about 0.2:1 to about 5:1, about 0.5:1 to about 3:1, about 0.2:1 to about 1.2:1, about 0.4:1 to about 1:1, about 0.5:1 to about 1:1, about 0.5:1 to about 1.5:1, about 0.5:1 to about 2:1, about 0.5:1 to about 2.5:1, about 0.5:1 to about 3:1, about 1:1 to about 1.5:1, about 1:1 to about 2:1, about 1:1 to about 2.5:1, about 1:1 to about 3:1, about 1.5:1 to about 2:1, about 1.5:1 to about 2.5:1, about 1.5:1 to about 3:1, about 2:1 to about 2.5:1, about 2:1 to about 3:1, or about 2.5:1 to about 3:1.

In some embodiments, an amorphous solid dispersion and/or a pharmaceutical composition disclosed herein comprises one or more inorganic acids. In some embodiments, the one or more inorganic acids comprise one or more of hydrochloric acid, hydrobromic acid, hydriodic acid, sulfuric acid, nitric acid, boric acid, and phosphoric acid. In some embodiments, the one or more inorganic acids comprise hydrochloric acid. In some embodiments, the inorganic acid is completely ionized. In some embodiments, the inorganic acid is partially ionized. In some embodiments, partial ionization refers to an equilibrium in which 1% or more of the inorganic acid is ionized.

In some embodiments, the one or more inorganic acids are present in the amorphous solid dispersion and/or in the pharmaceutical composition in an amount of from about 0.10% to about 99% by weight of the total composition. In some embodiments, the one or more inorganic acids are present in the amorphous solid dispersion and/or in the pharmaceutical composition in an amount of from about 0.10% to about 80%, 1% to about 80%, from about 1% to about 60%, from about 1% to about 50%, from about 10% to about 80%, from about 10% to about 60%, from about 10% to about 50%, from about 20% to about 80%, from about 20% to about 60%, from about 20% to about 50%, from about 30% to about 80%, from about 30% to about 60%, from about 30% to about 50%, or from about 30% to about 40% by weight of the total composition. In some embodiments, the one or more inorganic acids are present in the amorphous solid dispersion and/or in the pharmaceutical composition in an amount of about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, or about 45% by weight of the total composition. In some embodiments, the one or more inorganic acids comprise hydrochloric acid. In some embodiments, the one or more inorganic acids are present in the amorphous solid dispersion and/or in the pharmaceutical composition in an amount of about 1.0 mg to about 1000 mg, including but not limited to about 1.0 mg, 2.0 mg, 3.0 mg, 4.0 mg, 5.0 mg, 10.0 mg, 15.0 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, or 350 mg. In some embodiments, the one or more inorganic acids are present in an amount of from about 0.1 mg to about 100 mg, from about 1 mg to about 50 mg, from about 2 mg to about 20 mg, from about 5 mg to about 15 mg, from about 7 mg to about 25 mg, from about 7 mg to about 20 mg, or from about 10 mg to about 18 mg.

In some embodiments, an amorphous solid dispersion disclosed herein comprises a first acid and a second acid. In some embodiments, a molar ratio of the second acid to the first acid is from about 0.05:1 to about 20:1. In some embodiments, the molar ratio of the second acid to the first acid is from about 0.5:1 to about 10:1. In some embodiments, the molar ratio of the second acid to the first acid is from about 1:1 to about 4:1. In some embodiments, the molar ratio of the second acid to the first acid is about 2:1. In some embodiments, a molar ratio of the API to the first acid is about 0.1:1 to about 10:1. In some embodiments, a molar ratio of the API to the first acid is from about 0.2:1 to about 5:1 or from about 0.5:1 to about 2:1. In some embodiments, a molar ratio of the API to the first acid is about 1:1. In some embodiments, a mass ratio of the API to the second acid is about 0.05:1 to about 20:1. In some embodiments, a mass ratio of the API to the second acid is from about 0.1:1 to about 5:1 or from about 0.2:1 to about 1:1. In some embodiments, a mass ratio of the API to the second acid is about 0.5:1.

In some embodiments, the first acid has a pKa smaller than 1. In some embodiments, the first acid has a pKa that is at most 2. In some embodiments, the first acid is an organic acid. In some embodiments, the first acid is an inorganic acid. In some embodiments, the second acid is an organic acid. In some embodiments, the second acid is an inorganic acid. In some embodiments, both the first and the second acids are organic acids. In some embodiments, the first acid is methanesulfonic acid. In some embodiments, the second acid is tartaric acid. In some embodiments, the first acid is present in the amorphous solid dispersion and/or in the pharmaceutical composition in an amount of 5 mg to 200 mg. In some embodiments, the first acid is present in an amount of from about 10 mg to about 100 mg, from about 15 mg to about 50 mg, from about 20 mg to about 40 mg, from about 20 mg to about 30 mg, or from about 25 mg to about 30 mg. In some embodiments, the second acid is present in the amorphous solid dispersion and/or in the pharmaceutical composition in an amount of 5 mg to 400 mg. In some embodiments, the second acid is present in an amount of from about 10 mg to about 400 mg, from about 20 mg to about 300 mg, from about 50 mg to about 200 mg, from about 50 mg to about 150 mg, from about 50 mg to about 100 mg, from about 30 mg to about 60 mg, from about 25 mg to about 75 mg, or from about 100 mg to about 200 mg.

Hydrophilic High-Molecular Weight Material

In some embodiments, an amorphous solid dispersion and/or a pharmaceutical composition described herein comprises a hydrophilic high-molecular weight material. In some embodiments, the hydrophilic high-molecular weight material comprises at least one of polyvinylpyrrolidone (povidone) (e.g., PVP-K30), vinylpyrrolidone-vinyl acetate copolymer (copovidone or PVP-VA64, e.g., sold under the trade name Kollidon® VA 64), polyvinyl alcohol (PVA), polysaccharide, hydroxypropyl methylcellulose (HPMC or Hypromellose; e.g., HPMC-E5), hydroxyethyl cellulose (HEC), hydroxypropyl cellulose (HPC), polyethylene oxide, hydroxypropyl-β-cyclodextrin (HP-β-CD), sulfobutylether-β-cyclodextrin, hydroxypropyl methylcellulose acetate succinate (HPMC-AS-HF), polyethylene glycol (PEG), polyvinyl caprolactam-polyvinyl acetate-polyethylene glycol graft copolymer (PVAc-PVCap-PEG, e.g., sold under the trade name Soluplus), polysaccharide, or a combination thereof. In some embodiments, the hydrophilic high-molecular weight material is PVP, copovidone, crospovidone, HPMC, or a combination thereof. In some embodiments, the hydrophilic high-molecular weight material comprises HPMC and crospovidone. In some embodiments, the hydrophilic high-molecular weight material comprises HPMC and PVP. In some embodiments, the hydrophilic high-molecular weight material comprises HPMC and copovidone. In some embodiments, the hydrophilic high-molecular weight material comprises copovidone and crospovidone.

In some embodiments, an amorphous solid dispersion described herein comprises a hydrophilic high-molecular weight material. In some embodiments, the hydrophilic high-molecular weight material comprises at least one of polyvinylpyrrolidone (povidone) (e.g., PVP-K30), vinylpyrrolidone-vinyl acetate copolymer (copovidone or PVP-VA64), Soluplus, polyvinyl alcohol (PVA), polysaccharide, hydroxypropyl methylcellulose (HPMC or Hypromellose; e.g., HPMC-E5), hydroxyethyl cellulose (HEC), hydroxypropyl cellulose (HPC), polyethylene oxide, hydroxypropyl-β-cyclodextrin (HP-β-CD), sulfobutylether-β-cyclodextrin, hydroxypropyl methylcellulose acetate succinate (HPMC-AS-HF), polyethylene glycol (PEG), polyvinyl caprolactam-polyvinyl acetate-polyethylene glycol graft copolymer (PVAc-PVCap-PEG, e.g., sold under the trade name Soluplus), polysaccharide, or a combination thereof. In some embodiments, the amorphous solid dispersion comprises PVP, HPMC, crospovidone, crospovidone, or a combination thereof. In some embodiments, the amorphous solid dispersion comprises HPMC. In some embodiments, the amorphous solid dispersion comprises PVP. In some embodiments, the amorphous solid dispersion comprises crospovidone. In some embodiments, the amorphous solid dispersion comprises crospovidone.

In some embodiments, the hydrophilic high-molecular weight material is present in a disclosed amorphous solid dispersion and/or a disclosed pharmaceutical composition in an amount of at least 10 mg, at least 20 mg, at least 25 mg, at least 30 mg, at least 40 mg, at least 50 mg, at least 60 mg, at least 70 mg, at least 75 mg, at least 80 mg, at least 90 mg, at least 100 mg, at least 110 mg, at least 120 mg, at least 125 mg, at least 130 mg, at least 140 mg, at least 150 mg, at least 160 mg, at least 170 mg, at least 175 mg, at least 180 mg, at least 190 mg, or at least 200 mg. In some embodiments, the hydrophilic high-molecular weight material is present in a disclosed amorphous solid dispersion and/or a disclosed pharmaceutical composition in an amount of at most 30 mg, at most 40 mg, at most 50 mg, at most 60 mg, at most 70 mg, at most 75 mg, at most 80 mg, at most 90 mg, at most 100 mg, at most 110 mg, at most 120 mg, at most 125 mg, at most 130 mg, at most 140 mg, at most 150 mg, at most 160 mg, at most 170 mg, at most 175 mg, at most 180 mg, at most 190 mg, at most 200 mg, at most 250 mg, or at most 300 mg. In some embodiments, the hydrophilic high-molecular weight material is present in a disclosed amorphous solid dispersion and/or a disclosed pharmaceutical composition in an amount of about 10 mg, about 20 mg, about 25 mg, about 30 mg, about 40 mg, about 50 mg, about 60 mg, about 70 mg, about 80 mg, about 90 mg, about 95 mg, about 100 mg, about 105 mg, about 110 mg, about 120 mg, about 125 mg, about 130 mg, about 140 mg, about 150 mg, about 160 mg, about 170 mg, about 180 mg, about 190 mg, about 200 mg, about 225 mg, or about 250 mg. In some embodiments, the hydrophilic high-molecular weight material is present in a disclosed amorphous solid dispersion and/or a disclosed pharmaceutical composition in an amount of 10 mg to 1000 mg. In some embodiments, the hydrophilic high-molecular weight material is present in an amount of from about 50 mg to about 150 mg, from about 55 mg to about 150 mg, from about 60 mg to about 150 mg, from about 65 mg to about 150 mg, from about 70 mg to about 150 mg, from about 75 mg to about 150 mg, from about 80 mg to about 150 mg, from about 85 mg to about 150 mg, from about 90 mg to about 150 mg, from about 95 mg to about 150 mg, from about 100 mg to about 150 mg, from about 105 mg to about 150 mg, from about 110 mg to about 150 mg, from about 115 mg to about 150 mg, from about 120 mg to about 150 mg, from about 125 mg to about 150 mg, from about 130 mg to about 150 mg, from about 135 mg to about 150 mg, from about 140 mg to about 150 mg, from about 145 mg to about 150 mg, from about 50 mg to about 145 mg, from about 50 mg to about 140 mg, from about 50 mg to about 130 mg, from about 50 mg to about 135 mg, from about 50 mg to about 125 mg, from about 50 mg to about 120 mg, from about 50 mg to about 115 mg, from about 50 mg to about 110 mg, from about 50 mg to about 105 mg, from about 50 mg to about 100 mg, from about 50 mg to about 95 mg, from about 50 mg to about 90 mg, from about 50 mg to about 85 mg, from about 50 mg to about 80 mg, from about 50 mg to about 75 mg, from about 50 mg to about 70 mg, from about 50 mg to about 65 mg, from about 50 mg to about 60 mg, or from about 50 mg to about 55 mg. In some embodiments, the hydrophilic high-molecular weight material is present in an amount of 20 mg to 500 mg, 20 mg to 400 mg, 20 mg to 300 mg, 25 mg to 250 mg, 30 mg to 200 mg, 50 mg to 200 mg, 50 mg to 150 mg, 50 mg to 125 mg, 75 mg to 200 mg, 75 mg to 150 mg, 100 mg to 125 mg, or 100 mg to 150 mg. In some embodiments, the hydrophilic high-molecular weight material comprises PVP, HPMC, copovidone, crospovidone, or a combination thereof. In some embodiments, the amorphous solid dispersion comprises about 100 mg of HPMC.

In some embodiments a composition is provided that comprises a hydrophilic high-molecular weight material (such as HPMC, PVP, copovidone, or a mixture thereof) that is present at an amount from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg.

In some embodiments, the hydrophilic high-molecular weight material is present in the disclosed amorphous solid dispersion in an amount of 5% to 80% of a total weigh of the amorphous solid dispersion. In some embodiments, the hydrophilic high-molecular weight material is present in an amount of from about 10% to about 60%, from about 30% to about 50%, from about 5% to about 60%, from about 20% to about 50%, from about 20% to about 40%, from about 25% to about 35%, from about 28% to about 32%, from about 25% to about 30%, or from about 20% to about 30% of a total weigh of the amorphous solid dispersion. In some embodiments, the hydrophilic high-molecular weight material comprises from about 20% to about 50% of the total weight of the amorphous solid dispersion. In some embodiments, the hydrophilic high-molecular weight material comprises from about 20% to about 40% of the total weight of the amorphous solid dispersion. In some embodiments, the hydrophilic high-molecular weight material is present in an amount of about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% of a total weigh of the amorphous solid dispersion. In some embodiments, the hydrophilic high-molecular weight material is present in an amount of about 28% of a total weigh of the amorphous solid dispersion.

In some embodiments, the hydrophilic high-molecular weight material is present in the disclosed pharmaceutical composition in an amount of 5% to 80% of a total weigh of the pharmaceutical composition. In some embodiments, the hydrophilic high-molecular weight material is present in an amount of from about 10% to about 60%, from about 30% to about 50%, from about 5% to about 60%, from about 20% to about 50%, from about 20% to about 40%, from about 25% to about 35%, from about 28% to about 32%, from about 25% to about 30%, or from about 20% to about 30% of a total weigh of the pharmaceutical composition. In some embodiments, the hydrophilic high-molecular weight material comprises from about 20% to about 50% of the total weight of the pharmaceutical composition. In some embodiments, the hydrophilic high-molecular weight material comprises from about 20% to about 40% of the total weight of the pharmaceutical composition. In some embodiments, the hydrophilic high-molecular weight material is present in an amount of about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% of a total weigh of the pharmaceutical composition.

In some embodiments, a hydrophilic high-molecular weight material is present in the disclosed pharmaceutical composition as an excipient. In some embodiments, a hydrophilic high-molecular weight material is present in the disclosed pharmaceutical composition as an excipient of the amorphous solid dispersion in an amount of about 0.10% to about 20% by weight, including about 0.1% to about 10%, about 3% to about 8%, about 1%, about 2%, about 3%, about 5%, about 6%, about 7%, about 8%, about 9% or about 10% by weight of the pharmaceutical composition. In some embodiments, a hydrophilic high-molecular weight material is present in the disclosed pharmaceutical composition as an excipient of the amorphous solid dispersion in an amount of about 5% by weight of the pharmaceutical composition.

The hydrophilic high-molecular weight material can have a low, medium, or high viscosity. In some embodiments, the viscosity of the hydrophilic high-molecular weight material is about 4.0-6.0 cP when measured at 2% in water at 20° C. In some embodiments, the viscosity of the hydrophilic high-molecular weight material is about 4.0-6.0 cP when measured at 2% in water at 20° C. In some embodiments, the viscosity of the hydrophilic high-molecular weight material is less than about 120 cP when measured at 2% in water at 20° C. In some embodiments, the viscosity of the hydrophilic high-molecular weight material is from about 100 cP to about 20,000 cP when measured at 2% in water at 20° C. In some embodiments, the viscosity of the hydrophilic high-molecular weight material is less than about 4000 cP when measured at 2% in water at 20° C. In some embodiments, the viscosity of the hydrophilic high-molecular weight material is from about 4000 cP to about 100,000 cP when measured at 2% in water at 20° C.

The hydrophilic high-molecular weight material can have a particle size distribution. In some embodiments, a median diameter of the hydrophilic high-molecular weight material is less than 500 μm, less than 250 μm, less than 150 μm, less than 125 μm, less than 100 μm, less than 75 μm, less than 50 μm, less than 40 μm, less than 30 μm, less than 20 μm, or less than 10 μm. In some embodiments, a median diameter of the hydrophilic high-molecular weight material is at least 100 nm, at least 500 nm, at least 1 μm, at least 5 μm, at least 10 μm, at least 20 μm, at least 25 μm, at least 50 μm, at least 75 μm, at least 100 μm, at least 125 μm, or at least 150 μm. In some embodiments, a median diameter of the hydrophilic high-molecular weight material is from about 50 nm to about 1000 μm, from about 100 nm to about 500 μm, from about 1 μm to about 250 μm, from about 1 μm to about 200 μm, from about 1 μm to about 150 μm, or from about 50 μm to about 150 μm.

Other Excipients and Additives

The present disclosure relates to pharmaceutical compositions and methods of administering thereof, the pharmaceutical compositions comprising an amorphous solid dispersion comprising an API. In some embodiments, the pharmaceutical compositions comprise one or more excipients or additives. In some embodiments, the pharmaceutical compositions comprise an API, one or more acids, and a first acid, wherein the first acid is organic; a second acid; and a high-molecular weight material. In some embodiments, the API is at least partially protonated. In some embodiments, the API is in a salt or solvate form. In some embodiments, the one or more acids comprise two organic acids.

Excipients and additives that can be used in a described pharmaceutical composition include additives well known in the art. Such additives include, but are not limited to, anti-adherents (anti-sticking agents, glidants, flow promoters, lubricants) (e.g., talc, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate) anticoagulants (e.g., acetylated monoglycerides), antifoaming agents (e.g., long-chain alcohols and silicone derivatives), antioxidants (e.g., BHT, BHA, gallic acid, propyl gallate, ascorbic acid, ascorbyl palmitate, 4hydroxymethyl-2,6-di-tert-butyl phenol, tocopherol, etc.), binders (adhesives), i.e., agents that impart cohesive properties to powdered materials through particle-particle bonding, (e.g., matrix binders (dry starch, dry sugars), film binders (PVP, starch paste, celluloses, bentonite, sucrose)), chemical binders (e.g., polymeric cellulose derivatives, such as carboxy methyl cellulose, crospovidone (i.e., cross linked polyvinyl N-pyrrolidone), HPC, hydroxypropyl methylcellulose (HPMC), etc., sugar syrups, corn syrup, water soluble polysaccharides (e.g., acacia, tragacanth, guar, alginates, etc), gelatin, gelatin hydrolysate, agar, sucrose, dextrose, non-cellulosic binders (e.g., PVP, PEG, vinyl pyrrolidone copolymers, pregelatinized starch, sorbitol, glucose, etc.), chelating agents (e.g., EDTA and EDTA salts), coagulants (e.g., alginates) colorants or opaquants, (e.g., titanium dioxide, food dyes, lakes, natural vegetable colorants, iron oxides, silicates, sulfates, magnesium hydroxide and aluminum hydroxide), coolants, (e.g. halogenated hydrocarbons (e.g., trichloroethane, trichloroethylene, dichloromethane, fluorotrichloromethane), diethylether and liquid nitrogen) cryoprotectants (e.g., trehelose, phosphates, gelatin, dextran, mannitol, etc.), diluents or fillers (e.g., lactose, mannitol, talc, magnesium stearate, sodium chloride, potassium chloride, citric acid, spray-dried lactose, hydrolyzed starches, directly compressible starch, microcrystalline cellulose (MCC), cellulosics, sorbitol, sucrose, sucrose-based materials, calcium sulfate, dibasic calcium phosphate and dextrose disintegrants or super disintegrants (e.g., croscarmellose sodium, starch, starch derivatives, clays, gums, cellulose, cellulose derivatives, alginates, crosslinked polyvinylpyrrolidone, sodium starch glycolate and microcrystalline cellulose), hydrogen bonding agents (e.g., magnesium oxide), flavorants or desensitizers, (e.g., spray-dried flavors, essential oils and ethyl vanillin), ion-exchange resins (e.g., styrene/divinyl benzene copolymers, and quaternary ammonium compounds), plasticizers (e.g., polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate), preservatives, parabens, phenols, benzyl alcohol, and quaternary ammonium compounds), solvents (e.g., alcohols, ketones, esters, chlorinated hydrocarbons and water) sweeteners, including natural sweeteners (e.g., maltose, sucrose, glucose, sorbitol, glycerin and dextrins), and artificial sweeteners (e.g., aspartame, saccharine and saccharine salts) and thickeners (viscosity modifiers, thickening agents) (e.g., sugars, polyvinylpyrrolidone, cellulosics, polymers and alginates).

Additives can also comprise materials such as proteins (e.g., collagen, gelatin, Zein, gluten, mussel protein, lipoprotein), carbohydrates (e.g., alginates, carrageenan, cellulose derivatives, pectin, starch, chitosan), gums (e.g., xanthan gum, gum arabic), spermaceti, natural or synthetic waxes, camuaba wax, fatty acids (e.g., stearic acid, hydroxystearic acid), fatty alcohols, sugars, shellacs, such as those based on sugars (e.g., lactose, sucrose, dextrose) or starches, polysaccharide-based polymers (e.g., maltodextrin and maltodextrin derivatives, dextrates, cyclodextrin and cyclodextrin derivatives), cellulosic-based polymers (e.g., microcrystalline cellulose, sodium carboxymethyl cellulose, hydroxypropyl methylcellulose, ethyl cellulose, hydroxypropyl cellulose, cellulose acetate, cellulose nitrate, cellulose acetate butyrate, cellulose acetate, trimellitate, carboxymethylethyl cellulose, hydroxypropyl methyl cellulose phthalate), inorganics, (e.g., dicalcium phosphate, hydroxyapitite, tricalcium phosphate, talc and titania), polyols (e.g., mannitol, xylitol and sorbitol polyethylene glycol esters) and polymers (e.g., alginates, poly(lactide coglycolide), gelatin, crosslinked gelatin and agar-agar).

In some embodiments, the pharmaceutical compositions comprise one or more preservatives. Preservatives can include anti-microbials, antioxidants, and agents that enhance sterility. Exemplary preservatives include ascorbic acid, ascorbyl palmitate, butylatedhydroxyanisole (BHA), Butylatedhydroxytoulene (BHT), propyl gallate, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like. In some embodiments, an amorphous solid dispersion composition or a pharmaceutical composition described herein comprises an antioxidant. In some embodiments, the antioxidant comprises a-tocopherol acetate, acetone sodium bisulfite, acetylcysteine, ascorbic acid, vitamin E, ascorbyl palmitate, BHA, BHT, cysteine, cysteine hydrochloride, d-a-tocopherol (natural or synthetic), dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, or tocopherols. In some embodiments, an antioxidant or mixture of antioxidants are included as part of a solid dispersion. Exemplary antioxidants include but are not limited to BHT, BHA, gallic acid, propyl gallate, ascorbic acid, ascorbyl palmitate, 4hydroxymethyl-2,6-di-tert-butyl phenol, and tocopherol. In some embodiments, a pharmaceutical composition is provided that comprises from about 0.001% to about 10% by weight of the preservative (e.g., antioxidant). In some embodiments, the percent weight of the preservative or antioxidant is from about 0.001% to about 0.01%, about 0.001% to about 0.1%, about 0.001% to about 1%, about 0.001% to about 5%, about 0.001% to about 10%, about 0.01% to about 1%, about 0.01% to about 5%, about 0.01% to about 10%, about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 10%, about 1% to about 2%, about 1% to about 5%, about 1% to about 6%, about 1% to about 7%, about 1% to about 8%, or about 1% to about 10%.

In some embodiments, the excipients or additives comprise a filler, a binder, a disintegrating agent, a lubricant, an adsorbent, an acid, or a combination thereof. In some embodiments, the filler and/or binder comprises microcrystalline cellulose, crospovidone, lactose, or a combination thereof. In some embodiments, the disintegrating agent comprises microcrystalline cellulose. In some embodiments, the lubricant comprises magnesium stearate (abbreviated MgSt). In some embodiments, the acid comprises an organic acid such as tartaric acid. In some embodiments, the adsorbent is silica. In some embodiments, the pharmaceutical composition comprises microcrystalline cellulose, lactose, crospovidone, magnesium stearate, silicon dioxide, an organic acid, or a combination thereof.

In some embodiments, the weight ratio of the excipients to the API is from about 0.1:1 to about 10:1. In some embodiments, the weight ratio of the excipients to the API is from about 0.5:1 to about 5:1, from about 0.5:1 to about 4:1, from about 0.5:1 to about 3:1, from about 0.6:1 to about 4:1, from about 0.7:1 to about 3:1, from about 0.8:1 to about 2:1, from about 0.9:1 to about 1.1:1, from about 1:1 to about 3:1, from about 1:1 to about 4:1, from about 1:1 to about 5:1, or from about 1:1 to about 6:1.

It should be appreciated that there is considerable overlap between the above listed components in common usage, since a given component is often classified differently by different practitioners in the field, or is commonly used for any of several different functions, or may have differing functions depending on the levels in the composition. Thus, the above-listed components should be taken as merely exemplary, and not limiting, of the types of components that can be included in compositions of the present invention.

In some embodiments, amorphous solid dispersions described herein comprise an API, a surfactant, a non-ionic hydrophilic polymer, and optionally an adsorbent. In some embodiments, the surfactant is selected from polymeric non-ionic surfactants and phospholipids. In some embodiments, the polymeric non-ionic surfactant comprises a block copolymer of polyethylene glycol and polypropylene glycol. In some embodiments, the polymeric non-ionic surfactant is Poloxamer 188. In some embodiments, the surfactant comprises one or more phospholipids. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the surfactant comprises lecithin.

Non-Ionic Hydrophilic Polymer

In some embodiments, amorphous solid dispersions described herein comprise a non-ionic hydrophilic polymer. In some embodiments, the non-ionic hydrophilic polymer comprises oligosaccharide, polysaccharide, vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropylmethylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof. In some embodiments, the non-ionic hydrophilic polymer comprises HPMC, copovidone, PVP, HP-β-CD, PVA, HPMCAS, PVAc-PVCap-PEG, or a combination thereof. In some embodiments, the non-ionic hydrophilic polymer comprises about 5% to about 70% of the total weight of the amorphous solid dispersion. In some embodiments, the non-ionic hydrophilic polymer comprises from about 5% to about 60%, from about 5% to about 50%, from about 10% to about 50%, from about 10% to about 40%, from about 20% to about 40%, or from about 20% to about 30% of the total weight of the amorphous solid dispersion.

Adsorbent

Amorphous solid dispersions described herein can comprise an adsorbent. In some embodiments, a disclosed amorphous solid dispersion comprises an API, one or more acids, an adsorbent and a hydrophilic high-molecular weight material. In some embodiments, the excipients or additives of described pharmaceutical compositions comprise an adsorbent. Adsorbents can be solid, porous or super porous adsorption materials. They can comprise numerous micro- or nano-pores within their structures, resulting in very large surface areas, for example, greater than 500 m²/g. Exemplary adsorbents include, without limitation, silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide.

In some embodiments, an adsorbent such as silicon dioxide is present in a pharmaceutical composition described herein in an amount of at least 5 mg, at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the adsorbent is present in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the adsorbent is present in an amount of no more than 300 mg, 250 mg, 225 mg, 200 mg, 175 mg, 150 mg, 125 mg, 100 mg, 90 mg, 80 mg, 75 mg, 60 mg, 55 mg, 50 mg, or 25 mg. In some embodiments, the adsorbent is present in an amount of from about 0.1 mg to about 500 mg. In some embodiments, the adsorbent is present in an amount of from about 0.1 mg, about 0.2 mg, about 0.5 mg, about 1 mg, or 2 about 1 mg to about 5 mg, about 10 mg, about 25 mg, about 50 mg, about 100 mg, or about 200 mg. In some embodiments, the adsorbent is present in an amount of from about 1 mg to about 50 mg, from about 1 mg to about 20 mg, from about 1 mg to about 10 mg, or from about 1 mg to about 5 mg.

In some embodiments, the amorphous solid dispersion is granulated and incorporated into a pharmaceutical composition with extra granular additives. In some embodiments, the silicon dioxide is present outside of the amorphous solid dispersion as an extra-granular additive. In some embodiments, silicon dioxide is present in the amorphous solid dispersion as well as being an extra-granular additive.

In some embodiments, an adsorbent such as silicon dioxide is present in the disclosed amorphous solid dispersion. In some embodiments, the adsorbent comprises from about 1% to about 50% of the total weight of the amorphous solid dispersion. In some embodiments, the adsorbent comprises from about 1% to about 40%, from about 1% to about 30%, from about 1% to about 25%, from about 1% to about 20%, from about 1% to about 15%, from about 1% to about 10%, from about 5% to about 40%, from about 5% to about 25%, from about 5% to about 20%, from about 5% to about 15%, or from about 5% to about 10% of the total weight of the amorphous solid dispersion.

In some embodiments, an adsorbent described herein has a median diameter of 1-1000 nm. In some embodiments, an adsorbent described herein has a median diameter of from about 1 nm to about 750 nm, from about 1 nm to about 500 nm, from about 1 nm to about 250 nm, from about 1 nm to about 150 nm, from about 1 nm to about 100 nm, from about 1 nm to about 50 nm, from about 1 nm to about 25 nm, from about 10 nm to about 500 nm, from about 10 nm to about 250 nm, from about 10 nm to about 150 nm, from about 10 nm to about 100 nm, from about 10 nm to about 50 nm, from about 10 nm to about 25 nm, from about 50 nm to about 500 nm, from about 50 nm to about 250 nm, from about 50 nm to about 150 nm, from about 50 nm to about 100 nm, or from about 25 nm to about 50 nm. In some embodiments, an adsorbent described herein has a median diameter of from about 100 nm to about 1000 nm, from about 100 nm to about 750 nm, from about 200 nm to about 1000 nm, from about 200 nm to about 750 nm, from about 500 nm to about 1000 nm, or from about 500 nm to about 750 nm. In some embodiments, an adsorbent described herein has a median diameter larger than 1000 nm.

Surfactant

In some embodiments, pharmaceutical compositions described herein comprise an API (such as palbociclib or neratinib, or a salt or solvate thereof), a hydrophilic polymer, and a surfactant. In some embodiments, the API, hydrophilic polymer, and the surfactant are formulated as an amorphous solid dispersion. In some embodiments, the surfactant is selected from polymeric non-ionic surfactants and phospholipids. In some embodiments, the surfactants are compounds or mixture of compounds comprising a hydrophobic group (usually a hydrocarbon chain) and a hydrophilic group. They may perform one or more roles including solubility enhancer, bioavailability enhancer, stability enhancer, antioxidant and emulsifying agent. Examples of surfactants include, but are not limited to, phospholipids, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, sodium dodecyl sulfate, lauromacrogol Arlasolve, Poloxamers, Labrafil, Labrasol, Tween 80, Tocopheryl polyethylene glycol 1000 succinate (simply TPGS or Vitamin E TPGS) and the like.

In some embodiments, the surfactant used in the present disclosure can be a non-ionic surfactant. A non-ionic surfactant has no charged groups in its head. Exemplary non-ionic surfactants include, without limitation, fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), polyethoxylated tallow amine (POEA), and Tocopheryl polyethylene glycol 1000 succinate (simply TPGS or Vitamin E TPGS). In some embodiments, the surfactant comprises two more repeating units, such as polyoxyalkylene units. In some embodiments, the surfactant is a non-ionic surfactant that comprises polyethylene glycol. In some embodiments, the surfactant is a block copolymer of polyethylene glycol and polypropylene glycol. In some embodiments, the surfactant is a poloxamer such as poloxamer 188.

In some embodiments, the non-ionic surfactant has a number average molecular weight of from about 1000 to about 100,000 Da, 2000 to about 20,000 Da, from about 4000 to about 15,000 Da, from about 6000 to about 12,000 Da, or from about 7000 to about 10,000 Da. In some embodiments, the non-ionic surfactant has a number average molecular weight of from about 7000 to about 10,000 Da. In some embodiments, the non-ionic surfactant has an ethylene glycol content of from about 30 wt % to about 99 wt %, from about 50 wt % to about 95 wt %, from about 60 wt % to about 95 wt %, from about 75 wt % to about 90 wt %, or from about 80 wt % to about 85 wt %. In some embodiments, the non-ionic surfactant has an ethylene glycol content of from about 80 wt % to about 85 wt %.

In some embodiments, the surfactants are selected from fatty acids, phospholipids, sphingolipids, saccharolipids, polyketides, sterol lipids, prenol lipids and the like. In some embodiments, phospholipids are made up of glycerol to which is attached a phosphate group and two fatty acids. Other terms in the art for phospholipids include glycerophospholipids, phosphoglycerides, diacylglycerides and the like. The phosphate group can be unmodified (i.e., in the structure below R=H) or modified by attachment (i.e., in the structure below R≠H) to simple organic molecules such as, but not limited to choline, ethanolamine or serine. Phospholipids may be further modified by substitution onto one or more for the hydrocarbon chains.

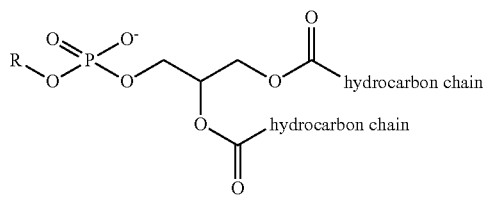

In some embodiments, phospholipids are selected from glycerophospholipid, sphingolipid, and/or phospholipid derivatives. In some embodiments, glycerophospholipids include, but are not limited to phosphatidylcholine, phosphatidyl ethanolamine, phosphatidyl ethanolamine, phosphatidyl serine, phosphatidyl glycerol, diphosphatidylglycerol, phosphatidylinositol, and mixtures thereof. Phospholipid derivatives according to the present invention include, but are not limited to dioleoylphosphatidylcholine, dimyristoylphosphatidylcholine, dipentadeanoylphosphatidylcholine, dilauroylphosphatidylchoine, dipalmitoylphosphatidylcholine (DPPC), distearoylphosphatidylcholine (DSPC), diarachidonyiphosphatidylcholine (DAPC), dioleoylphosphatidylethanolamine, dipalmitoylphosphatidylethanolamine (DPPE), and distearoylphosphatidylethanolamine (DSPE), disteraoylphosphatidylglycerol (DSPG), phosphatidylinositol, dipalmitoylphosphatidic acid (DPPA), distearoylphosphatidic acid (DSPA), and the like, and mixtures thereof. In some embodiments, the phospholipids comprise at least 40%, 50%, 60%, 70%, 80%, 90%, or 95% phosphatidylcholine by weight. In some embodiments, the phospholipids comprise greater than 80% phosphatidylcholine.

In some embodiments, the phospholipid is present in the pharmaceutical composition and/or in the amorphous solid dispersion in an amount of about 25 mg to about 200 mg. In some embodiments, the phospholipid is present in an amount of about 50 mg to 150 mg. In some embodiments, the phospholipids comprise 2.5%-20% of the total weight of the pharmaceutical composition. In some embodiments, the phospholipids comprise 5%-17% of the total weight of the pharmaceutical composition. In some embodiments, the phospholipids comprise greater than 80% phosphatidylcholine.

Phosphatidylcholines can refer to phospholipids wherein a choline group ($Me_3N^+$—$CH_2$—$CH_2$—O—) is attached to the phosphate group.

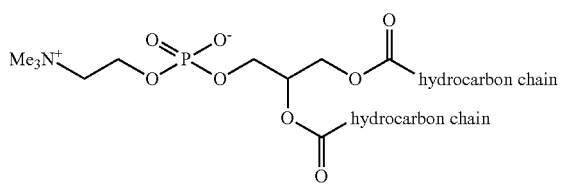

A non-limiting example of a phosphatidylcholine is 1-oleoyl-2-palmitoyl-phosphatidyl choline, as shown below:

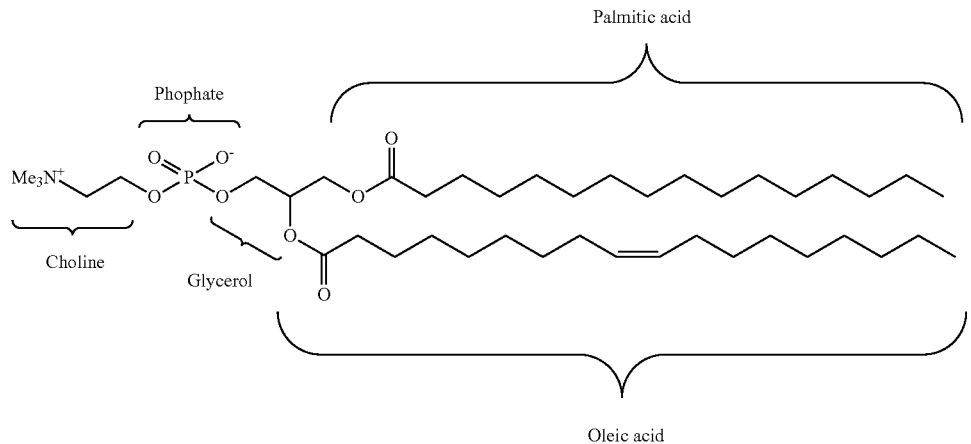

In some embodiments, the surfactant is a phospholipid. In some embodiments, the phospholipid is phosphatidylcholine. In some embodiments, the phospholipid is a mixture comprising phosphatidylcholine. In some embodiments, the surfactant is lecithin. In some embodiments, the lecithin is comprised of phosphatidylcholine. In some embodiments, the lecithin contains more than 25% of phosphatidylcholine. In some embodiments, the lecithin contains more than 80% of phosphatidylcholine. In some embodiments, the phosphatidylcholine is from egg origin. In some embodiments, the phosphatidylcholine is from or soybean origin.

In some embodiments, the surfactant is lecithin. The USP 40 definition of lecithin is "a complex mixture of acetone-insoluble phosphatides, which consist chiefly of phophatidylcholine, phosphatidylethanolamine, phosphatilinositol, and phosphatidic acid, present in conjunction with various amounts of other substances such as triglycerides, fatty acids, and carbohydrates, as separated from the crude vegetable oil source." In some embodiments, lecithin is a mixture of phospholipids. Lecithin can be isolated from various sources including, but not limited to eggs, soybeans, milk, marine sources, rapeseed, cottonseed and sunflower. In some embodiments, the lecithin used in the disclosed amorphous solid dispersions and/or pharmaceutical compositions is isolated from egg yolk.

In some embodiments, pharmaceutical compositions described herein include an API, a hydrophilic polymer, and a surfactant. In some embodiments, pharmaceutical compositions described herein comprises an API, a hydrophilic polymer, and a phospholipid or poloxamer. In some embodiments the API is palbociclib or a pharmaceutically acceptable salt thereof. In some embodiments, the API is palbociclib. In some embodiments, the API is a pharmaceutically acceptable salt of palbociclib. In some embodiments the API is neratinib or a pharmaceutically acceptable salt thereof, such as neratinib maleate. In some embodiments the API is neratinib. In some embodiments the API is neratinib maleate. In some embodiments, the surfactant is present in an amorphous solid dispersion and/or in a pharmaceutical composition disclosed herein in an amount of no less than 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the surfactant is present in an amorphous solid dispersion and/or in a pharmaceutical composition disclosed herein in an amount of no more than 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, 250 mg, 300 mg, or 500 mg. In some embodiments, the surfactant is present in an amorphous solid dispersion and/or in a pharmaceutical composition disclosed herein in an amount of about 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the surfactant is present in an amount of 50 mg to 500 mg. In some embodiments, the surfactant is present in an amount of 75 mg to 300 mg. In some embodiments, the surfactant is present in an amount of 100 mg to 200 mg. In some embodiments, the surfactant is present in an amount of 125 mg to 175 mg. In some embodiments, the surfactant comprises poloxamer or phospholipids such as lecithin. In some embodiments, the surfactant is a polymeric non-ionic surfactant such as poloxamer. In some embodiments, the surfactant comprises phospholipids such as lecithin. In some embodiments, the pharmaceutical composition described herein additionally comprise one or more adsorbents. In some embodiments, the pharmaceutical composition described herein additionally comprise one or more other additives. In some embodiments, other additives comprise organic and inorganic acids. In some embodiments, other additives comprise antioxidants.

In some embodiments, the surfactant (e.g., polymeric non-ionic surfactants or phospholipids) is present in an amorphous solid dispersion and/or in a pharmaceutical composition disclosed herein in an amount from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 350 mg, 400 mg, 450 mg, 455 mg, 460 mg, 465 mg, 470 mg, 475 mg, 480 mg, 485 mg, 490 mg, 495 mg, 500 mg, 550 mg, 600 mg, 650 mg, 700 mg, 750 mg, 800 mg, 850 mg, 900 mg, 950 mg, or 1000 mg.

In some embodiments, pharmaceutical compositions and/or amorphous solid dispersions described herein comprise an API, a hydrophilic polymer, and a surfactant. In some embodiments, the surfactant (e.g., polymeric non-ionic surfactants or phospholipids) comprises 0.1%-50% of the total weight of a herein described composition. In some embodiments, the composition is an amorphous solid dispersion. In some embodiments, the composition is a pharmaceutical composition. In some embodiments, the surfactant comprises 1%-30% of the total weight of the composition. In some embodiments, the surfactant comprises 5%-20% of the total weight of the composition. In some embodiments, the surfactant comprises 10%-17% of the total weight of the composition. In some embodiments, the surfactant comprises about 15%, about 16%, about 17%, about 18%, about 19% or about 20% of the total weight of the composition. In some embodiments, the ratio by weight of the hydrophilic polymer to the surfactant (e.g., polymeric non-ionic surfactants or phospholipids) is at least 0.75:1, at least 1:1, at least 1.1:1, at least 1.2:1, at least 1.3:1, at least 1.4:1, at least 1.5:1, or at least 2:1.

The compositions provided herein can be in unit-dosage forms or multiple-dosage forms. Unit-dosage forms, as used herein, refer to physically discrete units suitable for administration to human or non-human animal subjects and packaged individually. Each unit-dose can contain a predetermined quantity of an active ingredient(s) sufficient to produce the desired therapeutic effect, in association with the required pharmaceutical carriers or excipients. Examples of unit-dosage forms include, but are not limited to, individually packaged tablets and capsules. In some embodiments, the pharmaceutical compositions are administered as capsules.

The compositions may also be formulated as a modified release dosage form, including immediate-, delayed-, extended-, prolonged-, sustained-, pulsatile-, controlled-, extended, accelerated- and fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which are herein incorporated by reference in their entirety).

Pharmaceutical Compositions

Disclosed herein are pharmaceutical compositions comprising an amorphous solid dispersion that comprises an API. In some embodiments, the API is palbociclib or a salt or solvate thereof. In some embodiments, the API is palbociclib, wherein the palbociclib is at least partially protonated. In some embodiments, the API is neratinib or a salt or solvate thereof. In some embodiments, the API is neratinib, wherein the neratinib is at least partially protonated. In some embodiments, the API is one listed in Table A. In some embodiments, the amorphous solid dispersion comprises up to 99%, up to 90%, up to 85%, up to 80%, up to 75%, up to 70%, up to 65%, up to 60%, up to 55%, up to 50%, up to 45%, or up to 40% of the pharmaceutical composition by weight. In some embodiments, the amorphous solid dispersion comprises from 10% to 90%, 20% to 90%, 30% to 90%, 40% to 90%, 50% to 90%, 60% to 90%, 70% to 90%, 80% to 90%, 30% to 80%, 40% to 80%, 50% to 80%, 60% to 80%, 20% to 90%, 20% to 80%, 20% to 70%, 20% to 60%, or 20% to 50% of the pharmaceutical composition by weight.

In some embodiments, the pharmaceutical composition comprises the amorphous solid dispersion in an amount of about 50% to about 95% of a total weight of the pharmaceutical composition; microcrystalline cellulose in an amount of about 1% to about 12% of a total weight of the pharmaceutical composition; magnesium stearate in an amount of about 0.2% to about 5% of a total weight of the pharmaceutical composition; silica in an amount of about 0.2% to about 5% of a total weight of the pharmaceutical composition; and an organic acid in an amount of about 5% to about 20% of a total weight of the pharmaceutical composition. In some embodiments, the pharmaceutical composition comprises an amorphous solid dispersion that comprises about 70% to about 80% of a total weight of the pharmaceutical composition; microcrystalline cellulose in an amount of about 5% to about 6% of a total weight of the pharmaceutical composition; crospovidone in an amount of about 4.5% to about 5.5% of a total weight of the pharmaceutical composition; magnesium stearate in an amount of about 0.5% to about 1.5% of a total weight of the pharmaceutical composition; silica in an amount of about 1.5% to about 1.5% of a total weight of the pharmaceutical composition; and an organic acid in an amount of about 11% to about 13% of a total weight of the pharmaceutical composition.

In some embodiments, a pharmaceutical composition disclosed herein comprises an amorphous solid dispersion comprising palbociclib or a salt or solvate thereof, methanesulfonic acid, tartaric acid, and one or more excipients selected from HPMC; microcrystalline cellulose; crospovidone; magnesium stearate; silica; and an acid (such as tartaric acid). In some embodiments, the palbociclib is at least partially protonated. In some embodiments, the salt of palbociclib is palbociclib mesylate. In some embodiments, the amorphous solid dispersion comprises about 60% to about 90% of a total weight of the pharmaceutical composition. In some embodiments, the amorphous solid dispersion comprises about 75.7% of a total weight of the pharmaceutical composition. In some embodiments, the palbociclib or a salt or solvate thereof is present in an amount of about 30% to about 40% of a total weight of the amorphous solid dispersion. In some embodiments, the palbociclib or a salt or solvate thereof is present in an amount of about 35.5% of a total weight of the amorphous solid dispersion. In some embodiments, the amorphous solid dispersion comprises a mesylate salt of palbociclib. In some embodiments, the amorphous solid dispersion comprises methanesulfonic acid in an amount of from about 5% to about 15%, from about 2% to about 10%, or from about 2% to about 15% of a total weight of the amorphous dispersion. In some embodiments, the amorphous solid dispersion comprises methanesulfonic acid in an amount of about 7.6% of a total weight of the amorphous dispersion. In some embodiments, the amorphous solid dispersion comprises tartaric acid in an amount of from about 20% to about 40% or from about 25% to about 30% of a total weight of the amorphous dispersion. In some embodiments, the amorphous solid dispersion comprises tartaric acid in an amount of about 28.4% of a total weight of the amorphous dispersion. In some embodiments, the amorphous solid dispersion comprises a hydrophilic high-molecular weight material in an amount of from about 20% to about 40% or from about 25% to about 30% of a total weight of the amorphous dispersion. In some embodiments, the amorphous solid dispersion comprises HPMC in an amount of about 28.4% of a total weight of the amorphous dispersion. In some embodiments, microcrystalline cellulose is present in an amount of about 1% to about 10% of a total weight of the pharmaceutical composition. In some embodiments, microcrystalline cellulose is present in an amount of about 5.5% of a total weight of the pharmaceutical composition. In some embodiments, crospovidone is present in an amount of about 1% to about 10% of a total weight of the pharmaceutical composition. In some embodiments, crospovidone is present in an amount of about 5% of a total weight of the pharmaceutical composition. In some embodiments, magnesium stearate is present in an amount of about 0.1% to about 5% of a total weight of the pharmaceutical composition. In some embodiments, magnesium stearate is present in an amount of about 1% of a total weight of the pharmaceutical composition. In some embodiments, silica is present in an amount of about 0.1% to about 5% of a total weight of the pharmaceutical composition. In some embodiments, silica is present in an amount of about 1% of a total weight of the pharmaceutical composition.

In some embodiments, a pharmaceutical composition described herein comprises palbociclib, methanesulfonic acid, tartaric acid, HPMC, microcrystalline cellulose, crospovidone, magnesium stearate, silica, or a combination thereof. In some embodiments, the pharmaceutical composition comprises palbociclib in an amount equivalent to 75 mg, 100 mg, or 125 mg palbociclib free base. In some embodiments, the pharmaceutical composition described herein further comprises about 20 mg to 30 mg of methanesulfonic acid, about 125 mg to 175 mg of tartaric acid, about 75 mg to 100 mg of HPMC, about 20 mg to 30 mg of microcrystalline cellulose, about 20 mg to 30 mg of crospovidone, about 1 mg to 10 mg of magnesium stearate, and about 1 mg to 10 mg of silica. In some embodiments, the pharmaceutical composition described herein comprises about 26.7 mg of methanesulfonic acid, about 155 mg of tartaric acid, about 100 mg of HPMC, about 25.5 mg of microcrystalline cellulose, about 23.3 mg of crospovidone, about 4.7 mg of magnesium stearate, and about 4.7 mg of silica.

Pharmaceutical compositions described herein optionally comprise an inner matrix comprising an amorphous solid dispersion of the API, and an outer matrix comprising at least one pharmaceutically acceptable excipient. In some embodiments, the API is palbociclib. In some embodiments the API is neratinib or a pharmaceutically acceptable salt thereof, such as neratinib maleate. In some embodiments, the API is one listed in Table A. In some embodiments, the inner matrix comprises an amorphous solid dispersion and at least one pharmaceutically acceptable excipient. In some embodiments, the inner matrix is formed by mixing the amorphous solid dispersion with one or more pharmaceutically acceptable excipients, compressing the mixture, milling the compressed mixture, and screening the milled compressed mixture to produce particulates that are less than about 1000, 900, 800, 700, 600, 550, 500, 450, 400, 350, 300, 200, or 100 microns in size. In some embodiments, an outer matrix is added by mixing at least one pharmaceutically acceptable excipient with the particulates of the inner matrix. In some embodiments, the outer matrix encapsulates the inner matrix particulates. In some embodiments, the outer matrix partially encapsulates the inner matrix particulates. In some embodiments, the outer matrix creates a thin boundary between the majority of the inner matrix particulates. In some embodiments, the concentration of the API is higher in the inner matrix as compared to the outer matrix. In some embodiments, the inner and outer matrix share at least one pharmaceutically acceptable excipient. In some embodiments, the concentration of the at least one shared pharmaceutically acceptable excipient in the inner and outer matrices is non equal. In some embodiments, less than 20% of the API in the composition is present in the outer matrix. In some embodiments, less than 10% of the API in the composition is present in the outer matrix. In some embodiments, less than 5% of the API in the composition is present in the outer matrix. In some embodiments, less than 1% of the API in the composition is present in the outer matrix.

The present pharmaceutical compositions can take the form of solutions, suspensions, emulsion, tablets, pills, pellets, capsules, capsules containing liquids, powders, suppositories, emulsions, suspensions, or any other form suitable for use. Preferred pharmaceutical compositions are formulated for oral delivery. In one embodiment, the pharmaceutically acceptable vehicle is a capsule. Capsules may be hard capsules or soft capsules, push-fit capsules made of gelatin, as well as soft, sealed capsules made of gelatin and a plasticizer (such as glycerol or sorbitol). In some embodiments, the capsule contains about 1000 mg of the pharmaceutical composition. In some embodiments, the capsule contains less than 1000 mg of the pharmaceutical composition. Capsules can be of any size. Examples of standard sizes include, but are not limited to those listed in Table B, (#000, #00, #0, #1, #2, #3, #4, and #5). See, e.g., Remington's Pharmaceutical Sciences, page 1658-1659 (Alfonso Gennaro ed., Mack Publishing Company, Easton Pa., 18th ed., 1990), which is incorporated by reference. In some embodiments, the capsules used herein are of size #00 or #0.

TABLE B

| Size | Volume (mL) | Locked length (mm) | External diameter (mm) |
|---|---|---|---|
| 000 | 1.37 | 26.1 | 9.9 |
| 00 | 0.91 | 23.3 | 8.5 |
| 0 | 0.68 | 21.7 | 7.6 |
| 1 | 0.50 | 19.4 | 6.9 |
| 2 | 0.37 | 18.0 | 6.3 |

TABLE B-continued

| Size | Volume (mL) | Locked length (mm) | External diameter (mm) |
|---|---|---|---|
| 3 | 0.30 | 15.9 | 5.8 |
| 4 | 0.21 | 14.3 | 5.3 |

The amorphous solid dispersions described herein can increase the dissolution rate of the API, e.g., as shown in FIG. 1. In some embodiments, about 80% or more of the API is dissolved in about 10 minutes or less. In some embodiments, about 70% or more of the API is dissolved in about 10 minutes or less. In some embodiments, about 60% or more of the API is dissolved in about 10 minutes or less. In some embodiments, about 50% or more of the API is dissolved in about 10 minutes or less. In some embodiments, about 80% or more of the API is dissolved in about 20 minutes or less. In some embodiments, about 70% or more of the API is dissolved in about 20 minutes or less. In some embodiments, about 60% or more of the API is dissolved in about 20 minutes or less. In some embodiments, about 50% or more of the API is dissolved in about 20 minutes or less. In some embodiments, about 80% or more of the API is dissolved in about 30 minutes or less. In some embodiments, about 70% or more of the API is dissolved in about 30 minutes or less. In some embodiments, about 60% or more of the API is dissolved in about 30 minutes or less. In some embodiments, about 50% or more of the API is dissolved in about 30 minutes or less. In some embodiments, about 80% or more of the API is dissolved in about 60 minutes or less. In some embodiments, about 70% or more of the API is dissolved in about 60 minutes or less. In some embodiments, about 60% or more of the API is dissolved in about 60 minutes or less. In some embodiments, about 50% or more of the API is dissolved in about 60 minutes or less.

Methods of Treatment

In one aspect, disclosed herein are methods of treating a disease, wherein the method comprising administering a pharmaceutical composition or an amorphous solid dispersion described herein. Pharmaceutical compositions described herein can be administered for the treatment or prevention of diseases. When used to treat or prevent diseases or disorders, pharmaceutical compositions may be administered or applied singly, or in combination with other agents. Pharmaceutical compositions may also be administered or applied singly, in combination with other pharmaceutically active agents. Provided herein are methods of treatment and prophylaxis by administration to a subject in need of such treatment of a therapeutically effective amount of a pharmaceutical composition of the invention. The subject may be an animal, e.g., a mammal such as a human. In some embodiments, pharmaceutical compositions described herein are administered orally.

The pharmaceutical compositions described herein can be administered in prescribed regimens. In some embodiments, the pharmaceutical compositions are administered 3 times per day, twice per day, once per day, once every 2 days, once every 3 days, once every 4 days, once every 5 days, once every 6 days, once every week, twice every month, or once every month. In some embodiments, the dosage of API is 50 mg and is administered once a day. In some embodiments, the dosage of API is 75 mg and is administered once a day. In some embodiments, the dosage of API is 100 mg and is administered once a day. In some embodiments, the dosage of API is 125 mg and is administered once a day. In some embodiments, the dosage of API is 150 mg and is administered once a day. In some embodiments, the dosage of API is 200 mg and is administered once a day. In some embodiments, the dosage of API is 240 mg and is administered once a day. In some embodiments, the pharmaceutical composition is administered to the subject in an amount equivalent to 75 mg of palbociclib free base daily. In some embodiments, the pharmaceutical composition is administered to the subject in an amount equivalent to 100 mg of palbociclib free base daily. In some embodiments, the pharmaceutical composition is administered to the subject in an amount equivalent to 125 mg of palbociclib free base daily. In some embodiments, the pharmaceutical composition is administered to the subject in an amount equivalent to 125 mg of palbociclib free base daily for 21 days as a starting dose followed by 7 days off treatment. In some embodiments, 240 mg of neratinib maleate is administered daily. In some embodiments, neratinib maleate is administered following tratuzumab based therapy. In some embodiments, neratinib maleate is administered daily for one year. In some embodiments, loperamide is administered with the first dose of neratinib maleate and dosing continues for more than 50 days. In some embodiments, 240 mg of neratinib maleate is administered daily for up to one year. In some embodiments, 240 mg of neratinib maleate is administered once daily for 21 days in combination with capecitabine on days 1-14. In some embodiments, the dosage of 240 mg is divided into six 40 mg tablets. In some embodiments, the dosage is less than 240 mg.

The pharmaceutical compositions described herein can be administered with or without food. In some embodiments, the pharmaceutical composition is administered to the subject orally with food. In some embodiments, the pharmaceutical composition is administered to the subject orally without food. In some embodiments, the pharmaceutical composition is administered to the subject orally with food for 21 days followed by 7 days off treatment. In some embodiments, the pharmaceutical composition is administered to the subject orally with or without food for 21 days followed by 7 days off treatment. In some embodiments, the pharmaceutical composition is administered to the subject for a period of 1 to 7 weeks and followed by an off treatment of 1 to 2 weeks. In some embodiments, the pharmaceutical composition is administered to the subject for a period of one day to one year. In some embodiments, the pharmaceutical composition is administered approximately the same time each day.

The pharmaceutical compositions described herein can be administered for a cycle of 1 to 56 weeks. In some embodiments, a cycle comprises 28 days including 21 consecutive days of administering the pharmaceutical composition and 7 days off treatment. In some embodiments, the method comprises administering 500 mg of fulvestrant on days 1, 15 and 29 and once monthly thereafter.

In some embodiments, the dosages of the pharmaceutical composition is adjusted. In some embodiments, a starting dose of the pharmaceutical composition is equivalent to 125 mg of palbociclib free base daily. In some embodiments, a starting dose of the pharmaceutical composition is equivalent to 100 mg of palbociclib free base daily. In some embodiments, a starting dose of the pharmaceutical composition is equivalent to 50 mg of palbociclib free base daily. In some embodiments, the method of treating a disease comprises dose interruption and/or dose reductions based on individual safety and tolerability. In some embodiments, a first dose reduction comprises administering the pharmaceutical composition in an amount equivalent to 100 mg of palbociclib free base daily. In some embodiments, a second dose reduction comprises administering the pharmaceutical composition in an amount equivalent to 75 mg of palbociclib free base daily.

A pharmaceutical composition described herein can be used for treating a subject with cancer. In some embodiments, the subject is an adult patient with cancer. In some embodiments, the pharmaceutical compositions is used to treat or prevent breast cancer, liver cancer, ovarian epithelial carcinoma, leukemia, non-small cell lung cancer, multiple myeloma, colorectal cancer, liposarcoma, melanoma, melanoma cell lymphoma, or solid tumors. In some embodiments, a pharmaceutical composition described herein is used to treat a solid cancer. In some embodiments, the cancer is hormone receptor (HR)-negative, progesterone receptor (PR)-positive, and/or human epidermal growth factor receptor 2 (HER2)-positive breast cancer. In some embodiments, the cancer is a breast cancer. In some embodiments, the cancer is a hormone receptor (HR)-positive, human epidermal growth factor receptor 2 (HER2)-negative advanced, or metastatic breast cancer. In some embodiments, the pharmaceutical composition is used in combination with an aromatase inhibitor, and wherein the aromatase inhibitor is an initial endocrine based therapy in postmenopausal women. In some embodiments, the aromatase inhibitor is anastrozole, exemestane, or letrozole. In some embodiments, the pharmaceutical composition is used in combination with fulvestrant, wherein the subject is a women with disease progression following endocrine therapy. In some embodiments, the pharmaceutical composition is used in combination with capecitabine, for the treatment of adult patients with advanced or metastatic HER2-positive breast cancer who have received two or more prior anti-HER2 based regimens in the metastatic setting. In some embodiments, the pharmaceutical composition is used for the extended adjuvant treatment of adult patients with early stage HER2-positive breast cancer, to follow adjuvant trastuzumabbased therapy.

In some embodiments, a pharmaceutical composition described herein is used in combination with a second therapeutic agent. In some embodiments, the second therapeutic agent is an aromatase inhibitor. In some embodiments, the aromatase inhibitor is anastrozole, exemestane, or letrozole. In some embodiments, a pharmaceutical composition described herein is used in combination with an aromatase inhibitor as an initial endocrine-based therapy in postmenopausal women. In some embodiments, the second therapeutic agent is an estrogen receptor degrader. In some embodiments, the second therapeutic agent is fulvestrant. In some embodiments, a pharmaceutical composition described herein is used in combination with fulvestrant. Fulvestrant, or 7α-[9-[(4,4,5,5,5-Pentafluoropentyl)-sulfinyl]nonyl]estra-1,3,5(10)-triene-3,17β-diol, is a selective estrogen receptor degrader (SERD). Fulvestrant is sold under the brand name Faslodex, and alternative names of fulvestrant include ICI-182780, ZD-182780, and ZD-9238. In some embodiments, a pharmaceutical composition described herein can be used in combination with fulvestrant in patients with disease progression following endocrine therapy. In some embodiments, a pharmaceutical composition described herein is taken orally with food. In some embodiments, a pharmaceutical composition described herein is taken orally with food in combination with an aromatase inhibitor or fulvestrant. In some embodiments, the starting dose is 125 mg of palbociclib once daily taken with food for 21 days. In some embodiments, the starting dose is taken once daily with food for 21 days followed by 7 days off treatment. In some embodiments, the starting dose is taken for between 7 and 30 days, followed by at least 1 day of off treatment.

Methods of Manufacturing

In one aspect, disclosed herein is a method of manufacturing a pharmaceutical composition comprising an amorphous solid dispersion. In some embodiments, a method of manufacturing an amorphous solid dispersion, as disclosed herein, comprises one or more steps selected from (i) combining a solvent, a hydrophilic high-molecular weight material, and an API or a salt or solvate thereof, thereby producing a combined mixture; and (ii) removing at least a portion of the solvent from the mixture, thereby producing an amorphous solid dispersion. In some embodiments, a method of manufacturing an amorphous solid dispersion, as disclosed herein, comprises one or more steps selected from (i) combining a solvent, a hydrophilic high-molecular weight material, and an API or a salt or solvate thereof thereby producing a combined mixture; (ii) contacting the combined mixture with an adsorbent; and (iii) removing at least a portion of the solvent from the mixture, thereby producing an amorphous solid dispersion. In some embodiments, a method of manufacturing a pharmaceutical composition comprising an amorphous solid dispersion, as disclosed herein, comprises one or more steps selected from (i) combining a solvent, a hydrophilic high-molecular weight material, and an API or a salt or solvate thereof thereby producing a combined mixture; (ii) contacting the combined mixture with an adsorbent; (iii) removing at least a portion of the solvent from the mixture, thereby producing an amorphous solid dispersion; and (iv) mixing the amorphous solid dispersion with one or more pharmaceutically acceptable excipients or carriers. In some embodiments, the API or a salt or solvate thereof is at least partially protonated. In some embodiments, disclosed herein is a method of manufacturing a pharmaceutical composition comprising an amorphous solid dispersion, wherein the API is palbociclib. In some embodiments, the amorphous solid dispersion comprises a salt of palbociclib. In some embodiments, the amorphous solid dispersion comprises palbociclib mesylate. In some embodiments, the salt of palbociclib is formed in situ in the mixture. In some embodiments, disclosed herein is a method of manufacturing a pharmaceutical composition comprising an amorphous solid dispersion, wherein the API is neratinib. In some embodiments, the amorphous solid dispersion comprises a salt of neratinib. In some embodiments, the amorphous solid dispersion comprises neratinib maleate. In some embodiments, the salt of neratinib is formed in situ in the mixture.

In some embodiments, the method of manufacturing a pharmaceutical composition comprises concurrently combining a solvent, a hydrophilic high-molecular weight material, and an API or a salt or solvate thereof and contacting the combined mixture with an adsorbent; followed by removing the solvent (or a portion thereof) from the mixture. The adsorbent can added into the mixture before, concurrently, or after any one of the API or the pharmaceutically acceptable salt or solvate thereof, the hydrophilic high-molecular weight material, and the solvent. In some embodiments, the adsorbent is added into the solvent. In some embodiments, the method of manufacturing a pharmaceutical composition comprises first combining a solvent, a hydrophilic high-molecular weight material, and an API or a salt or solvate thereof, and then contacting the resultant mixture with an adsorbent. In some embodiments, a method of manufacturing a pharmaceutical composition comprising an amorphous solid dispersion, as disclosed herein, involves combining a solvent, a hydrophilic high-molecular weight material, and an API or a salt or solvate thereof; contacting the combined mixture with an adsorbent; removing the solvent (or a portion thereof) from the mixture, thereby producing an amorphous solid dispersion; and mixing the amorphous solid dispersion with one or more pharmaceutically acceptable excipients or carriers. In some embodiments, the adsorbent is silica. In some embodiments, one or more acids are combined with the API or a salt or solvate thereof in the mixture. In some embodiments, the one or more acids in the mixture comprise hydrochloric acid, hydrobromic acid, hydriodic acid, sulfuric acid, nitric acid, boric acid, and phosphoric acid, tartaric acid, fumaric acid, succinic acid, citric acid, lactic acid, malic acid, acetic acid, oxalic acid, an aliphatic sulfonic acid, an aromatic sulfonic acid, or a combination thereof.

In some embodiments, the method of manufacturing a pharmaceutical composition comprises combining a solvent, a hydrophilic high-molecular weight material, and an API or a salt or solvate thereof. In some embodiments, the combining comprises dissolving the API or a salt or solvent thereof, and the hydrophilic high-molecular weight material in the solvent. In some embodiments, the solvent comprises one or more organic solvents, water, or a combination thereof. In some embodiments, the solvent comprises water. In some embodiments, the solvent comprises water, wherein the ratio of the water to the API or a salt or solvate thereof is higher than 20:1. In some embodiments, the solvent comprises water, wherein the ratio of the water to the API or a salt or solvate thereof is higher than 15:1 or 10:1. In some embodiments, the solvent comprises alcohol such as ethanol. In some embodiments, the combining comprises heating the mixture to a certain temperature, such as 30° C., 45° C., 50° C., or 60° C. In some embodiments, the combining comprises mixing the API with other components in the mixture. In some embodiments, the solvent comprises dichloromethane, water, alcohol, or acetone. In some embodiments, alcohol is methanol, ethanol, propanol, any isomer or propanol, or any mixture thereof. In some embodiments, the solvent comprises water and one or more alcohols such as methanol, ethanol, propanol, etc. In some embodiments, the solvent comprises water and acetone. In some embodiments, the solvent comprises dichloromethane. In some embodiments, the solvent comprises dichloromethane and one or more alcohols. In some embodiments, the solvent comprises dichloromethane and acetone.

In some embodiments, the method of manufacturing comprises removing the solvent, or a portion thereof, to produce an amorphous solid dispersion. In some embodiments, removing the solvent, or a portion thereof, from the mixture comprises spray-drying or rotor evaporation. In some embodiments, a total solid content in the solution or mixture for spray drying is 5% (w/v) or more. In some embodiments, a total solid content in the solution or mixture for spray drying is 2% (w/v), 5% (w/v), 10% (w/v), 15% (w/v), 20% (w/v), 25% (w/v), or 30% (w/v) or more. In some embodiments, an amorphous solid dispersion collected in a sample container in a spray dryer during spray drying is more than 50% (w/w). In some embodiments, an amorphous solid dispersion collected in a sample container in a spray dryer during spray drying is at least 20% (w/w), at least 30% (w/w), at least 40% (w/w), at least 50% (w/w), at least 60% (w/w), at least 70% (w/w), or at least 80% (w/w). In some embodiments, removing the solvent, or a portion thereof, comprises spraying the mixture using a spray dryer. In some embodiments, the spray dryer configured to spray dry at a pressure of over 1.5 bar. In some embodiments, the spray dryer configured to spray dry at a pressure of over 2.0 to 2.5 bar. In some embodiments, the spray dryer configured to spray dry at a feed rate of over 1 mL/min. In some embodiments, the spray dryer configured to spray dry at a feed rate of about 5-12 mL/min. In some embodiments, the spray dryer configured to spray dry at a feed rate of about 5.8-9.8 mL/min. In some embodiments, the spray dryer is configured to produce particulates of an amorphous solid dispersion with a water content of less than 10%. In some embodiments, the spray dryer is configured to produce particulates of an amorphous solid dispersion with a water content of less than 8%.

In some embodiments, removing the solvent, or a portion thereof, comprises spraying the mixture onto the adsorbent. In some embodiments, the removing comprises drying in a fluid bed equipment. In some embodiments, the method further comprises compressing, milling or screening the amorphous solid dispersion with the one or more pharmaceutically acceptable excipients or carriers to form particulates.

In some embodiments, the components of the amorphous dispersion are mixed and heated in a solvent, and the solvent is removed to form the amorphous solid dispersion. In some embodiments, the solvent is water. In some embodiments, the solvent is a polar organic solvent. In some embodiments, the solvent is a protic solvent. In some embodiments, the solvent is selected from water, n-butanol, n-propanol, isopropanol, formic acid, nitromethane, ethanol, methanol, acetic acid, N-methylpyrrolidone, tetrahydrofuran, ethyl acetate, dimethylformamide, acetonitrile, dimethyl sulfoxide, and any combination thereof. In some embodiments, the solvent is selected from water, n-butanol, n-propanol, isopropanol, formic acid, nitromethane, ethanol, methanol, acetic acid, and any combination thereof. In some embodiments, the solvent is selected from water, ethanol and isopropanol.

Figure 2:
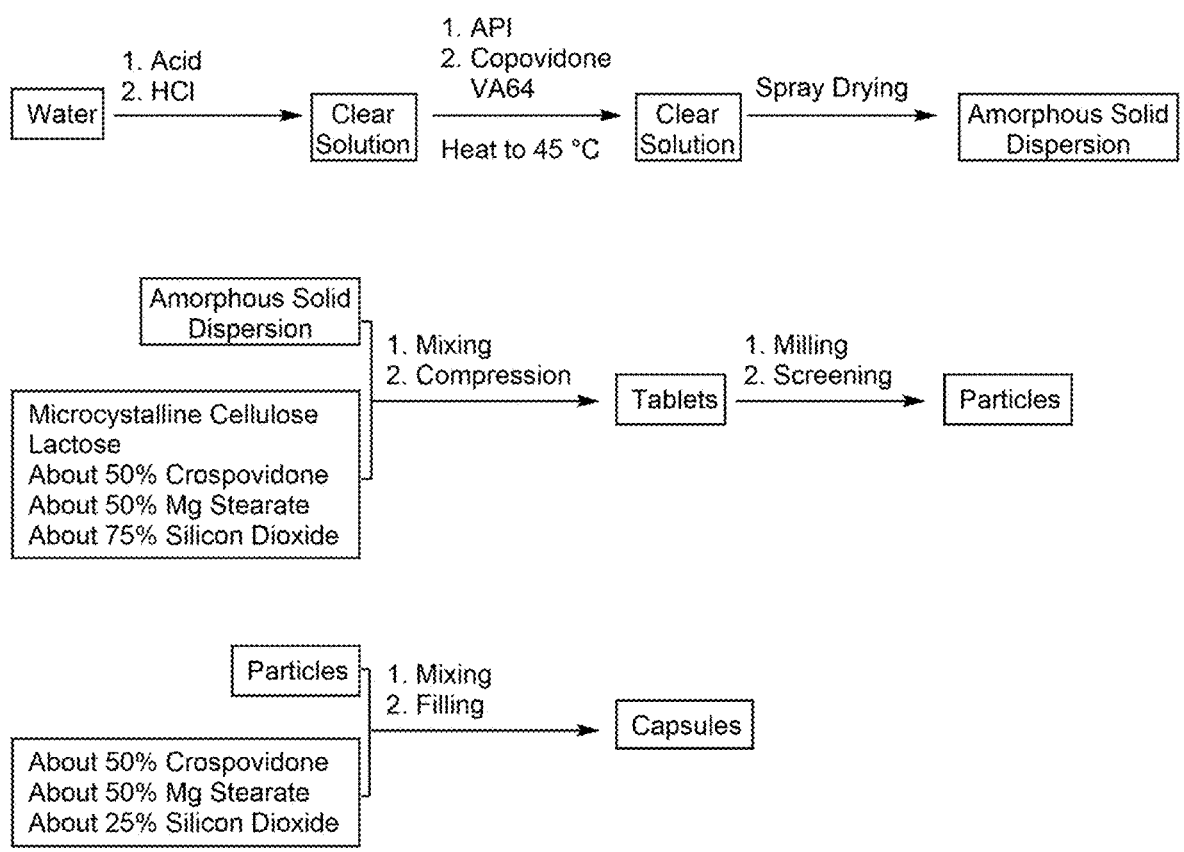
FIG. 2 is a workflow for manufacturing a pharmaceutical composition described herein.

In an exemplary manufacturing workflow, an amorphous solid dispersion is formed by first mixing tartaric acid and hydrochloric acid in water to form a clear solution. See FIG. 2. Next, an API and copovidone is added to the acidic clear solution, and the mixture is mixed and heated to 45° C. until a clear solution is formed. The clear solution comprising the API, acids and copovidone is then spray dried to form an amorphous solid dispersion. Following the formation of an amorphous solid dispersion, the amorphous solid dispersion is mixed with microcrystalline cellulose, lactose, about 50% of the total crospovidone used in the formulation, about 50% of the total magnesium stearate used in the formulation, and about 50% of the total silicon dioxide used in the formulation. The mixture is then pressed into tablets. The tablets are then milled and screened to form particles. The particles are then mixed with about 50% of the total crospovidone used in the formulation, about 50% of the total magnesium stearate used in the formulation, and about 25% of the total silicon dioxide. The mixture is then used to fill capsules. In some embodiments, hydrochloric acid is replaced with methanesulfonic acid.

In some embodiments, the pharmaceutical composition wherein the pharmaceutical composition comprises: a) an amorphous solid dispersion, the amorphous solid dispersion comprising: (i) an active pharmaceutical ingredient (API), or a pharmaceutically acceptable salt thereof; (ii) one or more interior acids; (iii) a hydrophilic high-molecular weight material; and (iv) optionally, an adsorbent; b) one or more exterior acids; and c) one or more pharmaceutically acceptable carriers or excipients, wherein the mass ratio of the one or more exterior acids to API is from about 0.1 to about 1:1.

The amorphous solid dispersion (ASD) is formed with the one or more interior acids without coming into contact with the one or more exterior acids. Following formation of the ASD, the ASD, the one or more exterior acids, and the one or more pharmaceutically acceptable carriers or excipients are mixed used to fill capsules.

Figure 3:
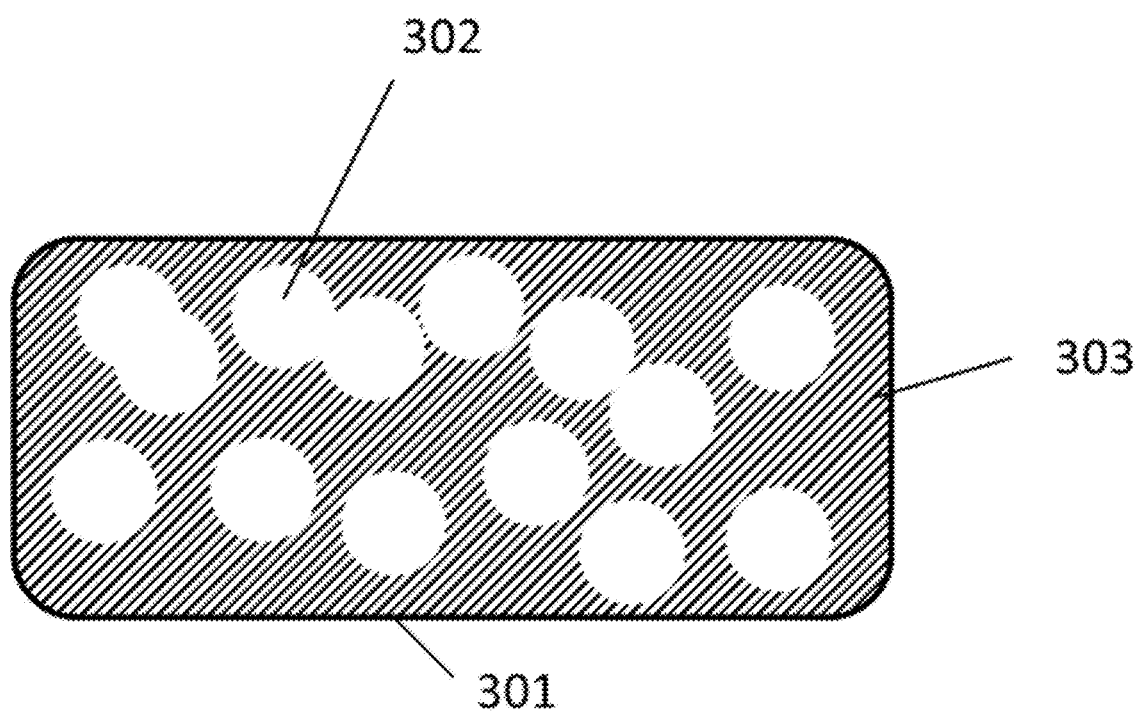
FIG. 3 is an illustration of a pharmaceutical composition having an inner and an outer matrix.
Figure 4:
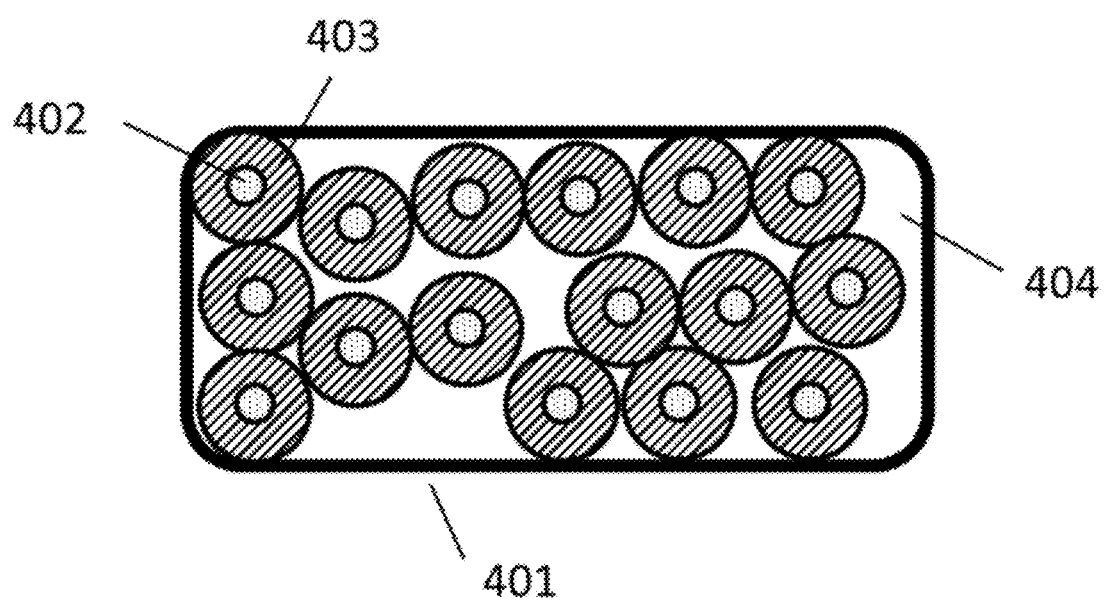
FIG. 4 is an illustration of a pharmaceutical composition having an inner and an outer matrix.

In some embodiments, multiple configurations of inner and outer matrices are disclosed herein. In a first exemplary configuration, a capsule or tablet 301 having an inner matrix 302 and outer matrix 303, wherein the inner matrix 302 comprises an amorphous solid dispersion described herein. The outer matrix 303 is in the space between the inner matrix particles. See FIG. 3. In some embodiments, particularly wherein the percent weight of the inner matrix 302 is greater than the percent weight of the outer matrix, the outer matrix 303 may form boundaries between particulates of the inner matrix. In some embodiments wherein the percent weight of the inner matrix 302 is greater than the percent weight of the outer matrix 303, the outer matrix 303 may fill the space or form pockets between particulates of the inner matrix 302. In some embodiments wherein the percent weight of the inner matrix is less than the percent weight of the outer matrix, the outer matrix may envelope the majority of inner matrix 302 particles. In a second configuration, a capsule 401 having an inner matrix 402 and outer matrix 403, wherein the inner matrix comprises an amorphous solid dispersion described herein. The outer matrix (403) wholly or partially encapsulates the inner matrix to form larger particulates within a capsule. In FIG. 4, wherein 401 is a capsule, the capsule may be partially filled with the ingredients of the composition, and partially filled with a gas 404, such as air or nitrogen. The pharmaceutical compositions described in FIGS. 3 and 4 may be in capsule or table form, among other forms described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

It is intended that the following claims define the scope of the invention and that methods and structures within the scope of these claims and their equivalents be covered thereby.

ADDITIONAL EMBODIMENTS

Embodiment 1. An amorphous solid dispersion, wherein the amorphous solid dispersion comprises:

a) a first acid, wherein the first acid is an organic acid that has a pKa of at most 2;

b) a second acid, wherein the second acid has a pKa greater than 2;

c) a hydrophilic high-molecular weight material; and d) palbociclib, a salt of palbociclib, or any combination thereof, wherein the salt of palbociclib comprises palbociclib and the first acid, wherein the molar ratio of the first acid to palbociclib is from about 0.5:1 to about 5:1, and wherein the weight ratio of the second acid to palbociclib is from about 0.1:1 to about 10:1.

Embodiment 2. The amorphous solid dispersion of embodiment 1, wherein palbociclib is at least partially protonated.

Embodiment 3. The amorphous solid dispersion of embodiment 1, wherein the salt of palbociclib is a monovalent palbociclib salt or a divalent palbociclib salt.

Embodiment 4. The amorphous solid dispersion of embodiment 1, wherein the salt of palbociclib comprises:
a) one or more cations comprising monoprotonated palbociclib, diprotonated palbociclib, or any combination thereof; and
b) one or more anions comprising a conjugate base of the first acid.

Embodiment 5. The amorphous solid dispersion of embodiment 2, wherein the at least partially protonated palbociclib contains about 1% or more of pronated palbociclib.

Embodiment 6. The amorphous solid dispersion of embodiment 5, wherein the at least partially protonated palbociclib contains about 10% or more of pronated palbociclib.

Embodiment 7. The amorphous solid dispersion of embodiment 6, wherein the at least partially protonated palbociclib contains about 50% or more of pronated palbociclib.

Embodiment 8. The amorphous solid dispersion of embodiment 1, wherein the first acid is oxalic acid, maleic acid, trichloroacetic acid, dichloroacetic acid, trifluoroacetic acid, an aliphatic sulfonic acid, or an aromatic sulfonic acid.

Embodiment 9. The amorphous solid dispersion of embodiment 1, wherein the first acid has a pKa of at most 1.

Embodiment 10. The amorphous solid dispersion of embodiment 1, wherein the first acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 11. The amorphous solid dispersion of embodiment 1, wherein the second acid has a pKa greater than 3.

Embodiment 12. The amorphous solid dispersion of embodiment 1, wherein the second acid has a pKa of about 2 to about 6.

Embodiment 13. The amorphous solid dispersion of embodiment 1, wherein the second acid is an inorganic acid.

Embodiment 14. The amorphous solid dispersion of embodiment 1, wherein the second acid is an organic acid.

Embodiment 15. The amorphous solid dispersion of embodiment 14, wherein the second acid is tartaric acid, fumaric acid, succinic acid, citric acid, lactic acid, malic acid, or acetic acid.

Embodiment 16. The amorphous solid dispersion of embodiment 15, wherein the second acid is tartaric acid.

Embodiment 17. The amorphous solid dispersion of embodiment 1, wherein the molar ratio of the first acid to palbociclib is from about 0.5:1 to about 3:1.

Embodiment 18. The amorphous solid dispersion of embodiment 1, wherein the molar ratio of the first acid to palbociclib is from about 1:1 to about 1.5:1.

Embodiment 19. The amorphous solid dispersion of embodiment 1, wherein a weight ratio of the second acid to palbociclib is from about 0.2:1 to about 5:1.

Embodiment 20. The amorphous solid dispersion of embodiment 1, wherein a weight ratio of the second acid to palbociclib is from about 0.2:1 to about 1.2:1.

Embodiment 21. The amorphous solid dispersion of embodiment 1, wherein the palbociclib is protonated on the pyridine nitrogen, the secondary piperazine nitrogen, or both.

Embodiment 22. The amorphous solid dispersion of embodiment 1, wherein the at least partially protonated palbociclib is a reaction product of the first acid with palbociclib free base or a salt thereof.

Embodiment 23. The amorphous solid dispersion of embodiment 1, wherein the amorphous solid dispersion comprises a salt of palbociclib, wherein the salt is a reaction product of palbociclib free base with the first acid.

Embodiment 24. The amorphous solid dispersion of embodiment 23, wherein the salt of palbociclib is formed in situ.

Embodiment 25. The amorphous solid dispersion of embodiment 1, wherein the amorphous solid dispersion consists of palbociclib mesylate, tartaric acid, a hydrophilic high molecular weight material, and an optional adsorbent.

Embodiment 26. The amorphous solid dispersion of embodiment 1, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 27. The amorphous solid dispersion of embodiment 26, wherein the hydrophilic high-molecular weight material is PVP, copovidone, HPMC, or a combination thereof.

Embodiment 28. The amorphous solid dispersion of embodiment 1, wherein the hydrophilic high-molecular weight material comprises from about 10% to about 80% of a total weight of the amorphous solid dispersion.

Embodiment 29. The amorphous solid dispersion of embodiment 1, wherein the hydrophilic high-molecular weight material comprises from about 20% to about 50% of a total weight of the amorphous solid dispersion.

Embodiment 30. The amorphous solid dispersion of embodiment 1, comprising:
the salt of palbociclib is palbociclib mesylate present in an amount of 20% to 60% of a total weight of the amorphous solid dispersion,
the second acid comprises tartaric acid present in an amount of 20% to 40% of a total weight of the amorphous solid dispersion, and
the hydrophilic high-molecular weight material is present in an amount of 20% to 40% of a total weight of the amorphous solid dispersion, and
wherein the hydrophilic high-molecular weight material is selected from HPMC, PVP, and copovidone.

Embodiment 31. The amorphous solid dispersion of embodiment 1, comprising:
the salt of palbociclib is palbociclib mesylate present in an amount of 40% to 45% of a total weight of the amorphous solid dispersion,
the second acid comprises tartaric acid present in an amount of 25% to 30% of a total weight of the amorphous solid dispersion, and
the hydrophilic high-molecular weight material is present in an amount of 25% to 30% of a total weight of the amorphous solid dispersion, wherein the hydrophilic high-molecular weight material is selected from HPMC, PVP, and copovidone.

Embodiment 32. The amorphous solid dispersion of embodiment 1, comprising:
the salt of palbociclib is palbociclib mesylate present in an amount of 25% to 45% of a total weight of the amorphous solid dispersion,
the first acid comprises methanesulfonic acid present in an amount of 1% to 15% of a total weight of the amorphous solid dispersion,
the second acid comprises tartaric acid present in an amount of 20% to 40% of a total weight of the amorphous solid dispersion, and
the hydrophilic high-molecular weight material in an amount of 20% to 40% of a total weight of the amorphous solid dispersion, wherein the hydrophilic high-molecular weight material is selected from HPMC, PVP, and copovidone.

Embodiment 33. The amorphous solid dispersion of embodiment 1, further comprising an adsorbent present in the amorphous solid dispersion in an amount of about 5% to about 50% of a total weight of the amorphous solid dispersion.

Embodiment 34. The amorphous solid dispersion of embodiment 1, further comprising an adsorbent selected from silica, active carbon, magnesium aluminum silicate, diatomite, microcrystalline cellulose (MCC), silicified microcrystalline cellulose (SMCC), talc, sugar, and sugar alcohol.

Embodiment 35. The amorphous solid dispersion of embodiment 34, wherein the adsorbent is silica.

Embodiment 36. An amorphous solid dispersion, wherein the amorphous solid dispersion comprises:
a) a first acid, wherein the first acid is an acid that has a pKa of at most 2;
b) a second acid, wherein the second acid has a pKa greater than 2;
c) a hydrophilic high-molecular weight material; and
d) palbociclib, a salt of palbociclib, or any combination thereof, wherein the salt of palbociclib comprises palbociclib and the first acid,
wherein a molar ratio of the first acid to palbociclib is from about 0.5:1 to about 3:1, and
wherein a weight ratio of the second acid to palbociclib is from about 0.2:1 to about 1.5:1.

Embodiment 37. The amorphous solid dispersion of embodiment 36, wherein palbociclib is at least partially protonated.

Embodiment 38. The amorphous solid dispersion of embodiment 36, wherein the salt of palbociclib is a monovalent palbociclib salt or a divalent palbociclib salt.

Embodiment 39. The amorphous solid dispersion of embodiment 36, wherein the salt of palbociclib comprises:
a) one or more cations comprising monoprotonated palbociclib, diprotonated palbociclib, or any combination thereof; and
b) one or more anions comprising a conjugate base of the first acid.

Embodiment 40. The amorphous solid dispersion of embodiment 37, wherein the at least partially protonated palbociclib contains about 1% or more of pronated palbociclib.

Embodiment 41. The amorphous solid dispersion of embodiment 37, wherein the at least partially protonated palbociclib contains about 10% or more of pronated palbociclib.

Embodiment 42. The amorphous solid dispersion of embodiment 37, wherein the at least partially protonated palbociclib contains about 50% or more of pronated palbociclib.

Embodiment 43. The amorphous solid dispersion of embodiment 36, wherein the first acid is oxalic acid, maleic acid, trichloroacetic acid, dichloroacetic acid, trifluoroacetic acid, an aliphatic sulfonic acid, or an aromatic sulfonic acid.

Embodiment 44. The amorphous solid dispersion of embodiment 36, wherein the first acid has a pKa of at most 1.

Embodiment 45. The amorphous solid dispersion of embodiment 36, wherein the first acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 46. The amorphous solid dispersion of embodiment 36, wherein the first acid is selected from hydrochloric acid, hydrobromic acid, hydriodic acid, sulfuric acid, and nitric acid.

Embodiment 47. The amorphous solid dispersion of embodiment 36, wherein the second acid has a pKa greater than 3.

Embodiment 48. The amorphous solid dispersion of embodiment 36, wherein the second acid has a pKa of about 2 to about 6.

Embodiment 49. The amorphous solid dispersion of embodiment 36, wherein the second acid is an inorganic acid.

Embodiment 50. The amorphous solid dispersion of embodiment 36, wherein the second acid is an organic acid.

Embodiment 51. The amorphous solid dispersion of embodiment 50, wherein the second acid is selected from tartaric acid, fumaric acid, succinic acid, citric acid, lactic acid, malic acid, and acetic acid.

Embodiment 52. The amorphous solid dispersion of embodiment 51, wherein the second acid is tartaric acid.

Embodiment 53. The amorphous solid dispersion of embodiment 36, wherein the molar ratio of the first acid to palbociclib is from about 1:1 to about 1.5:1.

Embodiment 54. The amorphous solid dispersion of embodiment 36, wherein a weight ratio of the second acid to palbociclib is from about 0.2:1 to about 1.2:1.

Embodiment 55. The amorphous solid dispersion of embodiment 36, wherein the palbociclib is protonated on the pyridine nitrogen, the secondary piperazine nitrogen, or both.

Embodiment 56. The amorphous solid dispersion of embodiment 36, wherein the at least partially protonated palbociclib is a reaction product of the first acid with palbociclib free base or a salt thereof.

Embodiment 57. The amorphous solid dispersion of embodiment 36, wherein the amorphous solid dispersion comprises a salt of palbociclib, wherein the salt is a reaction product of palbociclib free base with the first acid.

Embodiment 58. The amorphous solid dispersion of embodiment 57, wherein the salt of palbociclib is formed in situ.

Embodiment 59. The amorphous solid dispersion of embodiment 36, wherein the amorphous solid dispersion consists of palbociclib mesylate, tartaric acid, a hydrophilic high molecular weight material, and an optional adsorbent.

Embodiment 60. The amorphous solid dispersion of embodiment 36, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 61. The amorphous solid dispersion of embodiment 60, wherein the hydrophilic high-molecular weight material is PVP, copovidone, HPMC, or a combination thereof.

Embodiment 62. The amorphous solid dispersion of embodiment 36, wherein the hydrophilic high-molecular weight material is present in from about 10% to about 80% of a total weight of the amorphous solid dispersion.

Embodiment 63. The amorphous solid dispersion of embodiment 36, wherein the hydrophilic high-molecular weight material is present in from about 20% to about 50% of a total weight of the amorphous solid dispersion.

Embodiment 64. The amorphous solid dispersion of embodiment 36, wherein:
the salt of palbociclib is palbociclib mesylate present in an amount of 20% to 60% of a total weight of the amorphous solid dispersion,
the second acid comprises tartaric acid present in an amount of 20% to 40% of a total weight of the amorphous solid dispersion, and
the hydrophilic high-molecular weight material is present in 20% to 40% of a total weight of the amorphous solid dispersion, wherein the hydrophilic high-molecular weight material is selected from HPMC, PVP, and copovidone.

Embodiment 65. The amorphous solid dispersion of embodiment 36, comprising:
palbociclib mesylate in an amount of about 40% to about 45% of a total weight of the amorphous solid dispersion;
tartaric acid in an amount of about 25% to about 30% of a total weight of the amorphous solid dispersion; and
the hydrophilic high-molecular weight material in an amount of about 25% to about 30% of a total weight of the amorphous solid dispersion, wherein the hydrophilic high-molecular weight material is selected from HPMC, PVP, and copovidone.

Embodiment 66. The amorphous solid dispersion of embodiment 36, further comprising an adsorbent present in the amorphous solid dispersion in an amount of about 5% to about 50% of a total weight of the amorphous solid dispersion.

Embodiment 67. The amorphous solid dispersion of embodiment 36, further comprising an adsorbent selected from silica, active carbon, magnesium aluminum silicate, diatomite, microcrystalline cellulose (MCC), silicified microcrystalline cellulose (SMCC), talc, sugar, and sugar alcohol.

Embodiment 68. The amorphous solid dispersion of embodiment 67, wherein the adsorbent is silica.

Embodiment 69. An amorphous solid dispersion, wherein the amorphous solid dispersion comprises:
a) an active pharmaceutical ingredient (API), wherein the API comprises a compound of Formula (I),

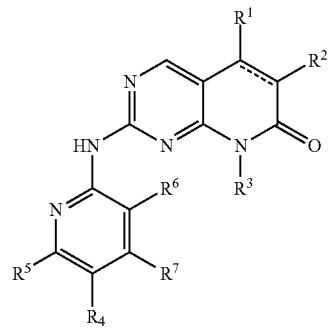

Formula (I)

or a pharmaceutically acceptable salt thereof,
wherein,
‒‒‒‒‒‒ represents a single bond or a double bond;
$R^1$ is $C_1$-$C_6$ alkyl;
$R^3$ is $C_1$-$C_8$ alkoxy, $C_3$-$C_7$ cycloalkyl, or $C_3$-$C_7$-heterocyclyl;
$R^2$ and $R^4$ are each independently selected from hydrogen, halogen, $C_1$-$C_8$ alkyl, $C_3$-$C_7$ cycloalkyl, $C_3$-$C_7$ heterocycloalkyl, $C_1$-$C_8$ alkoxy, $C_1$-$C_8$ alkoxyalkyl, $C_1$-$C_8$haloalkyl, $C_1$-$C_8$ hydroxyalkyl, $C_2$-$C_8$ alkenyl, $C_2$-$C_8$ alkynyl, nitrile, nitro, $OR^{10}$, $SR^{10}$, $NR^{10}R^{11}$, $N(O)R^{10}R^{11}$, $P(O)(OR^{10})(OR^{11})$, $(CR^{10}R^{11})_m NR^{12}R^{13}$, $COR^{10}$, $(CR^{10}R^{11})_m C(O)R^{12}$, $CO_2R^{10}$, $CONR^{10}R^{11}$, $C(O)NR^{10}SO_2R^{11}$, $NR^{10}SO_2R^{11}$, $C(O)NR^{10}R^{11}$, $S(O)_n R^{10}$, $SO_2NR^{10}R^{11}$, $P(O)(OR^{10})(OR^{11})$, $(CR^{10}R^{11})_m P(O)(OR^{12})(OR^{13})$, $(CR^{10}R^{11})_m$-aryl, $(CR^{10}R^{11})_m$-heteroaryl, and —$CR^{10}$=$CR^{11}C(O)R^{12}$;
each of $R^5$, $R^6$, and $R^7$ is independently hydrogen, halogen, $C_1$-$C_6$ alkyl, $C_1$-$C_6$haloalkyl, $C_1$-$C_8$ alkoxy, $C_1$-$C_8$ alkoxyalkyl, CN, $NO_2$, $OR^{10}$, $NR^{10}R^{11}$, $CO_2R^{10}$, $COR^{10}$, $S(O)_n R^{10}$, $CONR^{10}R^{11}$, $NR^{10}COR^{11}$, $NR^{10}SO_2R^{11}$, $SO_2NR^{10}R^{11}$, or $P(O)(OR^{10})(OR^{11})$;
each of $R^{10}$, $R^{11}$, $R^{12}$ and $R^{13}$ is independently hydrogen, $C_1$-$C_8$ alkyl, $C_2$-$C_8$ alkenyl, $C_2$-$C_8$ alkynyl, arylalkyl, cycloalkyl, heterocycloalkyl, aryl, or heteroaryl;
m is 0, 1, 2, 3, 4, 5, or 6; and
n is 0, 1 or 2;
b) a first acid, wherein the first acid is an organic acid that has a pKa of at most 2;
c) a second acid, wherein the second acid has a pKa greater than 2; and
d) a hydrophilic high-molecular weight material,
wherein the salt of Formula (I) comprises Formula (I) and the first acid
wherein a molar ratio of the first acid to Formula (I) is from about 0.5:1 to about 5:1, and
wherein a weight ratio of the second acid to Formula (I) is from about 0.1:1 to about 10:1.

Embodiment 70. The amorphous solid dispersion of claim 69, wherein ‒‒‒‒‒‒ represents a double bond.

Embodiment 71. The amorphous solid dispersion of claim 69, wherein each of $R^5$, $R^6$, and $R^7$ is hydrogen.

Embodiment 72. The amorphous solid dispersion of claim 69, wherein $R^1$ is methyl.

Embodiment 73. The amorphous solid dispersion of claim 69, wherein $R^2$ is $(CO)CH_3$.

Embodiment 74. The amorphous solid dispersion of claim 69, wherein $R^3$ is cyclopentyl.

Embodiment 75. The amorphous solid dispersion of claim 69, wherein $R^4$ is $C_3$-$C_7$ heterocycloalkyl.

Embodiment 76. The amorphous solid dispersion of claim 69, wherein $R^4$ is 6-membered heterocycloalkyl containing 1 or 2 ring nitrogen atoms.

Embodiment 77. The amorphous solid dispersion of embodiment 69, wherein the API comprises a pharmaceutically acceptable salt of Formula (I), wherein the pharmaceutically acceptable salt of Formula (I) is a monovalent salt or a divalent salt.

Embodiment 78. The amorphous solid dispersion of embodiment 69, wherein the API comprises a pharmaceutically acceptable salt of Formula (I), wherein the pharmaceutically acceptable salt of Formula (I) comprises:

a) one or more cations comprising monoprotonated API, diprotonated API, or any combination thereof; and b) one or more anions comprising a conjugate base of the first acid.

Embodiment 79. The amorphous solid dispersion of embodiment 69, wherein the first acid is oxalic acid, trichloroacetic acid, dichloroacetic acid, trifluoroacetic acid, an aliphatic sulfonic acid, or an aromatic sulfonic acid.

Embodiment 80. The amorphous solid dispersion of embodiment 69, wherein the first acid has a pKa smaller than 1.

Embodiment 81. The amorphous solid dispersion of embodiment 69, wherein the first acid is methanesulfonic acid or benzenesulfonic acid.

Embodiment 82. The amorphous solid dispersion of embodiment 69, wherein the API comprises mono-protonated API, di-protonated API, or both.

Embodiment 83. The amorphous solid dispersion of embodiment 69, wherein the second acid has a pKa larger than 1.

Embodiment 84. The amorphous solid dispersion of embodiment 69, wherein the second acid is an inorganic acid.

Embodiment 85. The amorphous solid dispersion of embodiment 69, wherein the second acid is an organic acid.

Embodiment 86. The amorphous solid dispersion of embodiment 69, wherein the second acid is selected from tartaric acid, fumaric acid, succinic acid, citric acid, lactic acid, malic acid, acetic acid, an aliphatic sulfonic acid, and an aromatic sulfonic acid.

Embodiment 87. The amorphous solid dispersion of embodiment 86, wherein the second acid is tartaric acid.

Embodiment 88. The amorphous solid dispersion of embodiment 69, wherein the molar ratio of the first acid to API is from about 0.5:1 to about 3:1.

Embodiment 89. The amorphous solid dispersion of embodiment 69, wherein the molar ratio of the first acid to API is from about 1:1 to about 1.5:1.

Embodiment 90. The amorphous solid dispersion of embodiment 69, wherein a weight ratio of the second acid to API is from about 0.2:1 to about 5:1.

Embodiment 91. The amorphous solid dispersion of embodiment 69, wherein a weight ratio of the second acid to API is from about 0.2:1 to about 1.2:1.

Embodiment 92. The amorphous solid dispersion of embodiment 69, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 93. The amorphous solid dispersion of embodiment 92, wherein the hydrophilic high-molecular weight material is PVP, copovidone, HPMC, or a combination thereof.

Embodiment 94. The amorphous solid dispersion of embodiment 69, wherein the hydrophilic high-molecular weight material comprises from about 10% to about 80% of a total weight of the amorphous solid dispersion.

Embodiment 95. The amorphous solid dispersion of embodiment 69, wherein the hydrophilic high-molecular weight material comprises from about 30% to about 50% of a total weight of the amorphous solid dispersion.

Embodiment 96. The amorphous solid dispersion of embodiment 69, wherein:

the API is a mesylate salt in an amount of 20% to 60% of a total weight of the amorphous solid dispersion, the second acid comprises tartaric acid present in an amount of 20% to 40% of a total weight of the amorphous solid dispersion, and the hydrophilic high-molecular weight material in an amount of 20% to 40% of a total weight of the amorphous solid dispersion, wherein the hydrophilic high-molecular weight material is selected from HPMC, PVP, and copovidone.

Embodiment 97. The amorphous solid dispersion of embodiment 69, wherein:

the API, wherein the API is present in 25% to 45% of a total weight of the amorphous solid dispersion;

the first acid comprises methanesulfonic acid present in an amount of 1% to 15% of a total weight of the amorphous solid dispersion;

the second acid comprises tartaric acid present in an amount of 20% to 40% of a total weight of the amorphous solid dispersion; and the hydrophilic high-molecular weight material in an amount of 20% to 40% of a total weight of the amorphous solid dispersion, wherein the hydrophilic high-molecular weight material is selected from HPMC, PVP, and copovidone.

Embodiment 98. The amorphous solid dispersion of embodiment 69, further comprising an adsorbent present in the amorphous solid dispersion in an amount of about 5% to about 50% of a total weight of the amorphous solid dispersion.

Embodiment 99. The amorphous solid dispersion of embodiment 69, further comprising an adsorbent selected from silica, active carbon, magnesium aluminum silicate, diatomite, microcrystalline cellulose (MCC), silicified microcrystalline cellulose (SMCC), talc, sugar, and sugar alcohol.

Embodiment 100. The amorphous solid dispersion of embodiment 99, wherein the absorbent is silica.

Embodiment 101. An amorphous solid dispersion, wherein the amorphous solid dispersion comprises:

a) a pharmaceutically acceptable salt of neratinib; and b) a hydrophilic high-molecular weight material.

Embodiment 102. The amorphous solid dispersion of embodiment 101, wherein the pharmaceutically acceptable salt of neratinib is a monovalent neratinib salt or a divalent neratinib salt.

Embodiment 103. The amorphous solid dispersion of embodiment 102, wherein the pharmaceutically acceptable salt of neratinib comprises:

a) one or more cations comprising monoprotonated neratinib, diprotonated neratinib, or any combination thereof, and b) one or more anions comprising a conjugate base of an acid.

Embodiment 104. The amorphous solid dispersion of embodiment 101, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 105. The amorphous solid dispersion of embodiment 104, wherein the hydrophilic high-molecular weight material is PVP, copovidone, HPMC, or a combination thereof.

Embodiment 106. The amorphous solid dispersion of embodiment 101, wherein the hydrophilic high-molecular weight material is present in from about 10% to about 60% of a total weight of the amorphous solid dispersion.

Embodiment 107. An amorphous solid dispersion, wherein the amorphous solid dispersion comprises:
a) neratinib, or a pharmaceutically acceptable salt thereof;
b) a two or more pharmaceutically acceptable acids; and
c) a hydrophilic high-molecular weight material,
wherein a molar ratio of the one or more acids to the API is from about 0.1:1 to about 20:1.

Embodiment 108. The amorphous solid dispersion of embodiment 107, wherein the pharmaceutically acceptable salt of neratinib is a monovalent neratinib salt or a divalent neratinib salt.

Embodiment 109. The amorphous solid dispersion of embodiment 108, wherein the pharmaceutically acceptable salt of neratinib comprises:
a) one or more cations comprising monoprotonated neratinib, diprotonated neratinib, or any combination thereof; and
b) one or more anions comprising a conjugate base of at least one of the two or more pharmaceutically acceptable acids.

Embodiment 110. The amorphous solid dispersion of 107, wherein the two or more pharmaceutically acceptable acids are organic acids.

Embodiment 111. The amorphous solid dispersion of 107, wherein the organic acids are selected from oxalic acid, maleic acid, trichloroacetic acid, dichloroacetic acid, trifluoroacetic acid, tartaric acid, fumaric acid, succinic acid, citric acid, lactic acid, malic acid, acetic acid, an aliphatic sulfonic acid, and an aromatic sulfonic acid.

Embodiment 112. The amorphous solid dispersion of embodiment 111, wherein the aliphatic sulfonic acid or the aromatic sulfonic acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 113. The amorphous solid dispersion of embodiment 107, wherein the molar ratio of the two or more pharmaceutically acceptable acids to neratinib is from about 2:1 to about 10:1.

Embodiment 114. The amorphous solid dispersion of embodiment 107, wherein the molar ratio of acid to neratinib is from about 2:1 to about 5:1.

Embodiment 115. The amorphous solid dispersion of embodiment 107, wherein the molar ratio of the two or more pharmaceutically acceptable acids to neratinib is from about 3:1 to about 4:1.

Embodiment 116. The amorphous solid dispersion of embodiment 107, wherein the salt of neratinib is formed in situ with at least one of the two or more pharmaceutically acceptable acids.

Embodiment 117. The amorphous solid dispersion of embodiment 107, wherein the amorphous solid dispersion comprises neratinib maleate, neratinib mesylate, or a combination thereof.

Embodiment 118. The amorphous solid dispersion of embodiment 107, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 119. The amorphous solid dispersion of embodiment 118, wherein the hydrophilic high-molecular weight material is PVP, copovidone, HPMC, or a combination thereof.

Embodiment 120. The amorphous solid dispersion of embodiment 107, wherein the hydrophilic high-molecular weight material is present in from about 10% to about 60% of a total weight of the amorphous solid dispersion.

Embodiment 121. The amorphous solid dispersion of embodiment 107, wherein the hydrophilic high-molecular weight material is present in from about 20% to about 50% of a total weight of the amorphous solid dispersion.

Embodiment 122. The amorphous solid dispersion of embodiment 107, comprising:
neratinib maleate in an amount of about 20% to about 60% of a total weight of the amorphous solid dispersion;
acid in an amount of about 10% to about 40% of a total weight of the amorphous solid dispersion; and
HPMC, PVP, or copovidone in an amount of about 20% to about 40% of a total weight of the amorphous solid dispersion.

Embodiment 123. An amorphous solid dispersion, wherein the amorphous solid dispersion comprises:
a) an active pharmaceutical ingredient (API), wherein the API comprises a compound of Formula (II),

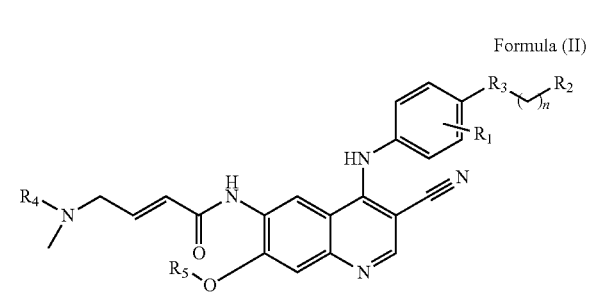

Formula (II)

or a pharmaceutically acceptable salt thereof,
wherein,
$R_1$ is halogen;
$R_2$ is a pyridinyl, thiophene, pyrimidine, thiazole, or phenyl optionally substituted with up to three substituents;
$R_3$ is —O— or —S—;
$R^4$ is $C_{1-3}$ alkyl or $C_{1-3}$ heteroalkyl;
$R^5$ is ethyl or methyl;
n is 0 or 1;
b) one or more acids; and
c) a hydrophilic high-molecular weight material.

Embodiment 124. The amorphous solid dispersion of embodiment 123, wherein $R_1$ is chlorine.

Embodiment 125. The amorphous solid dispersion of embodiment 123, wherein $R_2$ is pyridinyl.

Embodiment 126. The amorphous solid dispersion of embodiment 123, wherein $R_3$ is —O—.

Embodiment 127. The amorphous solid dispersion of embodiment 123, wherein $R_4$ is methyl.

Embodiment 128. The amorphous solid dispersion of embodiment 123, wherein $R_5$ is ethyl.

Embodiment 129. The amorphous solid dispersion of embodiment 123, wherein n is 1.

Embodiment 130. The amorphous solid dispersion of embodiment 123, wherein the compound of Formula (II) is a maleate salt.

Embodiment 131. The amorphous solid dispersion of embodiment 123, wherein the one or more acids comprise a first acid and a second acid.

Embodiment 132. The amorphous solid dispersion of embodiment 131, wherein the first acid has a pKa of at most 2 and the second has a pKa greater than 2.

Embodiment 133. The amorphous solid dispersion of embodiment 132, wherein the first acid has a pKa of at most 1, and second acid has a pKa greater than 1.

Embodiment 134. The amorphous solid dispersion of embodiment 131, wherein the molar ratio of the first acid to API is from about 0.5:1 to about 5:1 and wherein the weight ratio of the second acid to API is from about 0.1:1 to about 10:1.

Embodiment 135. The amorphous solid dispersion of embodiment 131, wherein the API is a pharmaceutically acceptable salt of Formula (II), wherein the pharmaceutically acceptable salt of Formula (II) is a monovalent salt or a divalent salt.

Embodiment 136. The amorphous solid dispersion of embodiment 135, wherein the API is a pharmaceutically acceptable salt of Formula (II), wherein the pharmaceutically acceptable salt of Formula (II) comprises:
a) one or more cations comprising monoprotonated API, diprotonated API, or any combination thereof; and
b) one or more anions comprising a conjugate base of the first acid.

Embodiment 137. An amorphous solid dispersion, wherein the amorphous solid dispersion comprises:
a) an active pharmaceutical ingredient (API),
wherein the API is at least partially protonated, and
wherein the API has a log P of at least 2;
b) one or more acids; and
c) a hydrophilic high-molecular weight material,
wherein a molar ratio of the one or more acids to the API is from about 0.1:1 to about 20:1.

Embodiment 138. The amorphous solid dispersion of embodiment 137, wherein the protonated API has a pKa of about 2 to about 10.

Embodiment 139. The amorphous solid dispersion of embodiment 137, wherein the protonated API has a pKa of about 3 to about 9.

Embodiment 140. The amorphous solid dispersion of embodiment 137, wherein the unprotonated API has a solubility of less than 0.1 mg/mL.

Embodiment 141. The amorphous solid dispersion of embodiment 137, wherein the unprotonated API has a solubility of less than 0.05 mg/mL.

Embodiment 142. The amorphous solid dispersion of embodiment 137, wherein the unprotonated API has a solubility of less than 0.01 mg/mL.

Embodiment 143. The amorphous solid dispersion of embodiment 137, wherein the API is gefitinib, erlotinib, or neratinib, or a salt or solvate thereof.

Embodiment 144. The amorphous solid dispersion of embodiment 137, wherein a ratio of a solubility of the protonated API to a solubility of the API as a free base is at least 10:1 in water.

Embodiment 145. The amorphous solid dispersion of embodiment 137, wherein a ratio of a solubility of the protonated API to a solubility of the API as a free base is at least 100:1 in water.

Embodiment 146. The amorphous solid dispersion of embodiment 137, wherein the API comprises mono-protonated API, di-protonated API, or both.

Embodiment 147. The amorphous solid dispersion of embodiment 137, wherein the one or more acids are partially or completely ionized acid.

Embodiment 148. The amorphous solid dispersion of embodiment 137, wherein the one or more acids comprise an organic acid.

Embodiment 149. The amorphous solid dispersion of embodiment 148, wherein the organic acid is oxalic acid, maleic acid, trichloroacetic acid, dichloroacetic acid, trifluoroacetic acid, tartaric acid, fumaric acid, succinic acid, citric acid, lactic acid, malic acid, and acetic acid an aliphatic sulfonic acid, or an aromatic sulfonic acid.

Embodiment 150. The amorphous solid dispersion of embodiment 149, wherein an aliphatic sulfonic acid or an aromatic sulfonic acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 151. The amorphous solid dispersion of embodiment 137, wherein the one or more acids comprise an inorganic acid.

Embodiment 152. The amorphous solid dispersion of embodiment 151, wherein the inorganic acid is selected from hydrochloric acid, hydrobromic acid, hydriodic acid, sulfuric acid, nitric acid, boric acid, and phosphoric acid.

Embodiment 153. The amorphous solid dispersion of embodiment 152, wherein the one or more acids comprise HCl.

Embodiment 154. The amorphous solid dispersion of embodiment 149, wherein the one or more acids comprise tartaric acid.

Embodiment 155. The amorphous solid dispersion of embodiment 137, wherein the one or more acids comprise a first acid and a second acid.

Embodiment 156. The amorphous solid dispersion of embodiment 155, wherein the first acid has a pKa of at most 2 and the second has a pKa greater than 2.

Embodiment 157. The amorphous solid dispersion of embodiment 155, wherein the first acid has a pKa of at most 1, and second acid has a pKa greater than 1.

Embodiment 158. The amorphous solid dispersion of embodiment 155, wherein the first acid is HCl and the second acid is tartaric acid.

Embodiment 159. The amorphous solid dispersion of embodiment 155, wherein the first acid is methanesulfonic acid and the second acid is tartaric acid.

Embodiment 160. The amorphous solid dispersion of embodiment 155, wherein the first acid is an organic or inorganic acid, and the second acid is an organic acid.

Embodiment 161. The amorphous solid dispersion of embodiment 155, wherein the first acid has a pKa equal to or smaller than 1, and second acid has a pKa larger than 1.

Embodiment 162. The amorphous solid dispersion of embodiment 155, wherein the API is at least partially protonated and is a reaction product of the first acid with a free base of the API.

Embodiment 163. The amorphous solid dispersion of embodiment 137, wherein the amorphous solid dispersion comprises a salt of the API, and wherein the salt is formed in situ.

Embodiment 164. The amorphous solid dispersion of embodiment 137, wherein the amorphous solid dispersion comprises a mesylate salt of the API or a hydrochloride salt of the API.

Embodiment 165. The amorphous solid dispersion of embodiment 137, wherein a molar ratio of the one or more acids to the API is from about 1:1 to about 4:1.

Embodiment 166. The amorphous solid dispersion of embodiment 137, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 167. The amorphous solid dispersion of embodiment 166, wherein the hydrophilic high-molecular weight material is PVP, copovidone, HPMC, or a combination thereof.

Embodiment 168. The amorphous solid dispersion of embodiment 137, wherein the hydrophilic high-molecular weight material is present in from about 10% to about 80% of a total weight of the amorphous solid dispersion.

Embodiment 169. The amorphous solid dispersion of embodiment 137, wherein the hydrophilic high-molecular weight material is present in from about 30% to about 50% of a total weight of the amorphous solid dispersion.

Embodiment 170. The amorphous solid dispersion of embodiment 137, wherein:
the API is present in an amount of about 25% to about 45% of a total weight of the amorphous solid dispersion;
one or more acids comprises tartaric acid present in an amount of about 20% to about 40% of a total weight of the amorphous solid dispersion; and
copovidone in an amount of about 20% to about 40% of a total weight of the amorphous solid dispersion.

Embodiment 171. The amorphous solid dispersion of embodiment 137, wherein:

a salt of the API comprising about 40% to about 60% of a total weight of the amorphous solid dispersion, wherein the salt of the API comprises a cation that is the protonated API and an anion from the one or more acids, and wherein the one or more acids are ionized; and
copovidone in an amount of about 40% to about 60% of a total weight of the amorphous solid dispersion.

Embodiment 172. The amorphous solid dispersion of embodiment 137, wherein the one or more acids is ionized HCl.

Embodiment 173. The amorphous solid dispersion of embodiment 137, further comprising an absorbent present in the amorphous solid dispersion in an amount of about 5% to about 50% of a total weight of the amorphous solid dispersion.

Embodiment 174. The amorphous solid dispersion of embodiment 137, further comprising an adsorbent selected from silica, active carbon, magnesium aluminum silicate, diatomite, microcrystalline cellulose (MCC), silicified microcrystalline cellulose (SMCC), talc, sugar, and sugar alcohol.

Embodiment 175. The amorphous solid dispersion of embodiment 174, wherein the adsorbent is silica.

Embodiment 176. An amorphous solid dispersion, wherein the amorphous solid dispersion comprises:
a) a first acid, wherein the first acid is an organic acid that has a pKa of at most 2;
b) a second acid, wherein the second acid has a pKa greater than 2;
c) a hydrophilic high-molecular weight material; and
d) an active pharmaceutical ingredient (API), a pharmaceutically acceptable salt of the API, or any combination thereof, wherein the pharmaceutically acceptable salt of the API comprises the API and the first acid,
wherein the molar ratio of the first acid to API is from about 0.5:1 to about 5:1, and
wherein the weight ratio of the second acid to API is from about 0.1:1 to about 10:1.

Embodiment 177. The amorphous solid dispersion of embodiment 176, wherein the pharmaceutically acceptable salt of the API is a monovalent salt or a divalent salt.

Embodiment 178. The amorphous solid dispersion of embodiment 177, wherein the pharmaceutically acceptable salt of the API comprises:
a) one or more cations comprising monoprotonated API, diprotonated API, or any combination thereof; and
b) one or more anions comprising a conjugate base of the first acid.

Embodiment 179. The amorphous solid dispersion of embodiment 176, wherein the molar ratio of the first acid to API is from about 0.5:1 to about 3:1, and the weight ratio of the second acid to API is from about 0.2:1 to about 1.5:1.

Embodiment 180. The amorphous solid dispersion of embodiment 176, wherein the first acid is oxalic acid, maleic acid, trichloroacetic acid, dichloroacetic acid, trifluoroacetic acid, an aliphatic sulfonic acid, or an aromatic sulfonic acid.

Embodiment 181. The amorphous solid dispersion of embodiment 180, wherein the first acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 182. The amorphous solid dispersion of embodiment 176, wherein the second acid is an inorganic acid.

Embodiment 183. The amorphous solid dispersion of embodiment 176, wherein the second acid is an organic acid.

Embodiment 184. The amorphous solid dispersion of embodiment 183, wherein the second acid is selected from tartaric acid, fumaric acid, succinic acid, citric acid, lactic acid, malic acid, and acetic acid.

Embodiment 185. The amorphous solid dispersion of embodiment 176, wherein the molar ratio of the first acid to API is from about 0.8:1 to about 2:1.

Embodiment 186. The amorphous solid dispersion of embodiment 176, wherein the molar ratio of the first acid to API is from about 1:1 to about 1.5:1.

Embodiment 187. The amorphous solid dispersion of embodiment 176, wherein a weight ratio of the second acid to API is from about 0.2:1 to about 1.2:1.

Embodiment 188. The amorphous solid dispersion of embodiment 176, wherein the amorphous solid dispersion comprises a salt of the API, wherein the salt is a reaction product of the API free base with the first acid.

Embodiment 189. The amorphous solid dispersion of embodiment 188, wherein the salt of the API is formed in situ.

Embodiment 190. The amorphous solid dispersion of embodiment 176, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-O-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 191. The amorphous solid dispersion of embodiment 190, wherein the hydrophilic high-molecular weight material is PVP, copovidone, HPMC, or a combination thereof.

Embodiment 192. The amorphous solid dispersion of embodiment 176, wherein the hydrophilic high-molecular weight material is present in from about 10% to about 80% of a total weight of the amorphous solid dispersion.

Embodiment 193. The amorphous solid dispersion of embodiment 176, wherein the hydrophilic high-molecular weight material is present in from about 20% to about 50% of a total weight of the amorphous solid dispersion.

Embodiment 194. The amorphous solid dispersion of embodiment 176, comprising:
the API in an amount of about 20% to about 60% of a total weight of the amorphous solid dispersion;
acid in an amount of about 20% to about 40% of a total weight of the amorphous solid dispersion; and
hydrophilic high-molecular weight material in an amount of about 20% to about 40% of a total weight of the amorphous solid dispersion.

Embodiment 195. The amorphous solid dispersion of embodiment 176, comprising:
the API in an amount of about 40% to about 45% of a total weight of the amorphous solid dispersion;
acid in an amount of about 25% to about 30% of a total weight of the amorphous solid dispersion; and
hydrophilic high-molecular weight material in an amount of about 25% to about 30% of a total weight of the amorphous solid dispersion.

Embodiment 196. The amorphous solid dispersion of embodiment 176, further comprising an adsorbent present in the amorphous solid dispersion in an amount of about 5% to about 50% of a total weight of the amorphous solid dispersion.

Embodiment 197. The amorphous solid dispersion of embodiment 176, wherein the adsorbent is selected from silica, active carbon, magnesium aluminum silicate, diatomite, microcrystalline cellulose (MCC), silicified microcrystalline cellulose (SMCC), talc, sugar, and sugar alcohol.

Embodiment 198. The amorphous solid dispersion of embodiment 197, wherein the adsorbent is silica.

Embodiment 199. A pharmaceutical composition, wherein the pharmaceutical composition comprises:
a) an amorphous solid dispersion of any one of embodiments 1 to 198, and
b) one or more pharmaceutically acceptable carriers or excipients.

Embodiment 200. The pharmaceutical composition of embodiment 199, wherein the one or more pharmaceutically acceptable carriers or excipients comprise a filler, a binder, a disintegrating agent, a lubricant, an adsorbent, an acid, or a combination thereof.

Embodiment 201. The pharmaceutical composition of embodiment 199, wherein the one or more pharmaceutically acceptable carriers or excipients comprise microcrystalline cellulose, lactose, crospovidone, magnesium stearate, silicon dioxide, an organic acid, or a combination thereof.

Embodiment 202. The pharmaceutical composition of embodiment 199, wherein:
a) the amorphous solid dispersion is present in an amount of about 50% to about 95% of a total weight of the pharmaceutical composition;
b) microcrystalline cellulose is present in an amount of about 1% to about 12% of a total weight of the pharmaceutical composition;
c) crospovidone is present in an amount of about 1% to about 10% of a total weight of the pharmaceutical composition;
d) magnesium stearate is present in an amount of about 0.2% to about 5% of a total weight of the pharmaceutical composition;
e) silica is present in an amount of about 0.2% to about 5% of a total weight of the pharmaceutical composition; and
f) an organic acid is present in an amount of about 5% to about 20% of a total weight of the pharmaceutical composition.

Embodiment 203. The pharmaceutical composition of embodiment 199, wherein:
a) the amorphous solid dispersion is present in an amount of about 70% to about 80% of a total weight of the pharmaceutical composition,
wherein the amorphous solid dispersion comprises:
i. palbociclib in an amount of about 25% to about 45% of a total weight of the amorphous solid dispersion;
ii. the first acid in an amount of about 1% to about 15% of a total weight of the amorphous solid dispersion;
iii. the second acid in an amount of about 20% to about 40% of a total weight of the amorphous solid dispersion; and
iv. the hydrophilic high-molecular weight material in an amount of about 20% to about 40% of a total weight of the amorphous solid dispersion;
b) microcrystalline cellulose is present in an amount of about 5% to about 6% of a total weight of the pharmaceutical composition;
c) crospovidone is present in an amount of about 4.5% to about 5.5% of a total weight of the pharmaceutical composition;

d) magnesium stearate is present in an amount of about 0.5% to about 1.5% of a total weight of the pharmaceutical composition;

e) silica is present in an amount of about 1.5% to about 1.5% of a total weight of the pharmaceutical composition; and f) an organic acid is present in an amount of about 11% to about 13% of a total weight of the pharmaceutical composition.

Embodiment 204. The pharmaceutical composition of embodiment 199, wherein:

a) the amorphous solid dispersion is present in an amount of about 75.7% of a total weight of the pharmaceutical composition,
wherein the amorphous solid dispersion comprises:
  i. palbociclib in an amount of about 35.5% of a total weight of the amorphous solid dispersion;
  ii. methanesulfonic acid in an amount of about 7.6% of a total weight of the amorphous solid dispersion;
  iii. tartaric acid in an amount of about 28.4% of a total weight of the amorphous solid dispersion; and
  iv. HPMC in an amount of about 28.4% of a total weight of the amorphous solid dispersion;

b) microcrystalline cellulose is present in an amount of about 5.5% of a total weight of the pharmaceutical composition;

c) crospovidone is present in an amount of about 5% of a total weight of the pharmaceutical composition;

d) magnesium stearate is present in an amount of about 1% of a total weight of the pharmaceutical composition;

e) silica is present in an amount of about 1% of a total weight of the pharmaceutical composition; and f) tartaric acid is present in an amount of about 11.8% of a total weight of the pharmaceutical composition.

Embodiment 205. The pharmaceutical composition of embodiment 199, wherein:

a) palbociclib is present in an amount of equivalent to 125 mg of palbociclib free base;

b) methanesulfonic acid is present in an amount of about 26.7 mg;

c) tartaric acid is present in an amount of about 155 mg;

d) HPMC is present in an amount of about 100 mg;

e) microcrystalline cellulose is present in an amount of about 25.5 mg;

f) crospovidone is present in an amount of about 23.3 mg;

g) magnesium stearate is present in an amount of about 4.7 mg; and h) silica is present in an amount of about 4.7 mg.

Embodiment 206. The pharmaceutical composition of embodiment 199, wherein palbociclib is present in an amount of equivalent to about 75 mg, about 100 mg, or about 125 mg of palbociclib free base.

Embodiment 207. A pharmaceutical composition, wherein the pharmaceutical composition comprises:

a) an amorphous solid dispersion, the amorphous solid dispersion comprising:
  i. an active pharmaceutical ingredient (API), a pharmaceutically acceptable salt thereof, or any combination thereof;
  ii. one or more interior acids;
  iii. a hydrophilic high-molecular weight material; and
  iv. optionally, an adsorbent;

b) one or more exterior acids;

c) one or more pharmaceutically acceptable carriers or excipients,
wherein the mass ratio of the one or more exterior acids to API is from about 0.1 to about 1:1.

Embodiment 208. The pharmaceutical composition of embodiment 207, wherein the pharmaceutically acceptable salt of the API is a monovalent salt or a divalent salt.

Embodiment 209. The amorphous solid dispersion of embodiment 208, wherein the pharmaceutically acceptable salt of the API comprises:

a) one or more cations comprising monoprotonated API, diprotonated API, or any combination thereof; and b) one or more anions comprising a conjugate base an interior acid.

Embodiment 210. The pharmaceutical composition of embodiment 207, wherein the mass ratio of the one or more exterior acids to API is from about 0.2 to about 0.7:1.

Embodiment 211. The pharmaceutical composition of embodiment 207, wherein the mass ratio of the one or more exterior acids to API is from about 0.3 to about 0.5:1.

Embodiment 212. The pharmaceutical composition of embodiment 207, wherein a molar ratio of the one or more interior acids to the API is from about 0.1:1 to about 20:1.

Embodiment 213. The pharmaceutical composition of embodiment 207, wherein a molar ratio of the one or more interior acids to the API is from about 0.1:1 to about 10:1.

Embodiment 214. The pharmaceutical composition of embodiment 207, wherein a molar ratio of the one or more interior acids to the API is from about 1:1 to about 5:1.

Embodiment 215. The pharmaceutical composition of embodiment 207, wherein the one or more exterior acids comprises one or more organic acid.

Embodiment 216. The pharmaceutical composition of embodiment 207, wherein the one or more exterior acids is oxalic acid, maleic acid, trichloroacetic acid, dichloroacetic acid, trifluoroacetic acid, tartaric acid, fumaric acid, succinic acid, citric acid, lactic acid, malic acid, and acetic acid an aliphatic sulfonic acid, or an aromatic sulfonic acid.

Embodiment 217. The pharmaceutical composition of embodiment 216, wherein an aliphatic sulfonic acid or an aromatic sulfonic acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 218. The pharmaceutical composition of embodiment 216, wherein the one or more exterior acids is tartaric acid.

Embodiment 219. The pharmaceutical composition of embodiment 207, wherein the one or more exterior acids comprises one or more inorganic acid.

Embodiment 220. The pharmaceutical composition of embodiment 219, wherein the inorganic acid is selected from hydrochloric acid, hydrobromic acid, hydriodic acid, sulfuric acid, nitric acid, boric acid, and phosphoric acid.

Embodiment 221. The pharmaceutical composition of embodiment 207, wherein the protonated API has a pKa of about 2 to about 10.

Embodiment 222. The pharmaceutical composition of embodiment 207, wherein the protonated API has a pKa of about 3 to about 9.

Embodiment 223. The pharmaceutical composition of embodiment 207, wherein the unprotonated API has a solubility of less than 0.1 mg/mL.

Embodiment 224. The pharmaceutical composition of embodiment 207, wherein the unprotonated API has a solubility of less than 0.05 mg/mL.

Embodiment 225. The pharmaceutical composition of embodiment 207, wherein the unprotonated API has a solubility of less than 0.01 mg/mL.

Embodiment 226. The pharmaceutical composition of embodiment 207, wherein the API is palbociclib, gefitinib, erlotinib, or neratinib, or a salt or solvate thereof.

Embodiment 227. The pharmaceutical composition of embodiment 207, wherein the one or more interior acids in the amorphous solid dispersion comprises an organic acid.

Embodiment 228. The pharmaceutical composition of embodiment 227, wherein the organic acid is oxalic acid, maleic acid, trichloroacetic acid, dichloroacetic acid, trifluoroacetic acid, tartaric acid, fumaric acid, succinic acid, citric acid, lactic acid, malic acid, and acetic acid an aliphatic sulfonic acid, or an aromatic sulfonic acid.

Embodiment 229. The pharmaceutical composition of embodiment 228, wherein an aliphatic sulfonic acid or an aromatic sulfonic acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

Embodiment 230. The pharmaceutical composition of embodiment 227, wherein the one or more interior acids comprise tartaric acid.

Embodiment 231. The pharmaceutical composition of embodiment 207, wherein the one or more interior acids comprise maleic acid.

Embodiment 232. The pharmaceutical composition of embodiment 207, wherein the one or more interior acids in the amorphous solid dispersion comprises an inorganic acid.

Embodiment 233. The pharmaceutical composition of embodiment 232, wherein the inorganic acid is selected from hydrochloric acid, hydrobromic acid, hydriodic acid, sulfuric acid, nitric acid, boric acid, and phosphoric acid.

Embodiment 234. The pharmaceutical composition of embodiment 207, wherein the one or more interior acids comprise hydrochloric acid.

Embodiment 235. The pharmaceutical composition of embodiment 207, wherein the one or more interior acids comprise a first acid and a second acid.

Embodiment 236. The pharmaceutical composition of embodiment 235, wherein the first acid has a pKa of at most 2 and the second has a pKa greater than 2.

Embodiment 237. The pharmaceutical composition of embodiment 235, wherein the first acid has a pKa of at most 1, and second acid has a pKa greater than 1.

Embodiment 238. The pharmaceutical composition of embodiment 235, wherein the first acid is HCl and the second acid is tartaric acid.

Embodiment 239. The pharmaceutical composition of embodiment 235, wherein the first acid is an organic or inorganic acid, and the second acid is an organic acid.

Embodiment 240. The pharmaceutical composition of embodiment 235, wherein the first acid is methanesulfonic acid and the second acid is tartaric acid.

Embodiment 241. The pharmaceutical composition of embodiment 207, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-β-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

Embodiment 242. The pharmaceutical composition of embodiment 241, wherein the hydrophilic high-molecular weight material is PVP, copovidone, HPMC, or a combination thereof.

Embodiment 243. A method of manufacturing a pharmaceutical composition comprising an amorphous solid dispersion, the method comprising:
(a) combining
(i) an active pharmaceutical ingredient (API) or a salt or solvate thereof;
(ii) a hydrophilic high-molecular weight material; and
(ii) a solvent;
thereby producing a mixture;
(b) contacting the mixture with an adsorbent; and
(c) removing at least a portion of the solvent from the mixture, thereby producing an amorphous solid dispersion.

Embodiment 244. The method of embodiment 243, wherein the removing comprises spray-drying or rotor evaporation.

Embodiment 245. The method of embodiment 243, wherein the adsorbent is silica.

Embodiment 246. The method of embodiment 243, wherein the removing comprises drying in a fluid bed equipment.

Embodiment 247. The method of embodiment 243, wherein the combining comprises dissolving the API or a salt or solvent thereof, and the hydrophilic high-molecular weight material in the solvent.

Embodiment 248. The method of embodiment 243, wherein the solvent comprises one or more organic solvents, or a combination thereof.

Embodiment 249. The method of embodiment 243, wherein the solvent comprises alcohol.

Embodiment 250. The method of embodiment 243, wherein the solvent is water.

Embodiment 251. The method of embodiment 243, wherein a weight ratio of the solvent to the API or a salt or solvate thereof is higher than 10:1.

Embodiment 252. The method of embodiment 243, further comprising mixing the amorphous solid dispersion with one or more pharmaceutically acceptable excipients or carriers.

Embodiment 253. The method of embodiment 243, further comprising compressing, milling or screening the amorphous solid dispersion with the one or more pharmaceutically acceptable excipients or carriers to form particulates.

Embodiment 254. A method of manufacturing an amorphous solid dispersion comprising an amorphous solid dispersion, the method comprising:
(a) combining
(i) a first acid, wherein the first acid is an organic acid that has a pKa of at most 2;
(ii) a second acid, wherein the second acid has a pKa greater than 2; and
(iii) a hydrophilic high-molecular weight material,
(iv) palbociclib, a salt of palbociclib, or any combination thereof, wherein the salt of palbociclib comprises palbociclib and the first acid;
wherein the molar ratio of the first acid to palbociclib is from about 0.5:1 to about 5:1, and
wherein the weight ratio of the second acid to palbociclib is from about 0.1:1 to about 10:1
(v) a solvent;
thereby producing a mixture; and
(b) removing at least a portion of the solvent from the mixture, thereby producing an amorphous solid dispersion.

Embodiment 255. The method of embodiment 254, further comprising adding an adsorbent into the mixture.

Embodiment 256. The method of embodiment 254, wherein the removing comprises spray-drying or rotor evaporation.

Embodiment 257. The method of embodiment 254, wherein the removing comprises spraying the mixture onto an adsorbent.

Embodiment 258. The method of embodiment 257, wherein the adsorbent is silica.

Embodiment 259. The method of embodiment 254, wherein the removing comprises drying in a fluid bed equipment.

Embodiment 260. The method of embodiment 254, wherein the combining comprises dissolving the API or a salt or solvent thereof, and the hydrophilic high-molecular weight material in the solvent.

Embodiment 261. The method of embodiment 254, wherein the solvent comprises one or more organic solvents, or a combination thereof.

Embodiment 262. The method of embodiment 254, wherein the solvent comprises alcohol.

Embodiment 263. The method of embodiment 254, wherein the solvent is water.

Embodiment 264. The method of embodiment 254, wherein a weight ratio of the solvent to the total weight of the first acid, second acid, hydrophilic high-molecular weight material, and palbociclib or a salt of palbociclib is less than 20:1.

Embodiment 265. The method of embodiment 254, further comprising mixing the amorphous solid dispersion with one or more pharmaceutically acceptable excipients or carriers.

Embodiment 266. The method of embodiment 254, further comprising compressing, milling or screening the amorphous solid dispersion with the one or more pharmaceutically acceptable excipients or carriers to form particulates.

Embodiment 267. A method of treating cancer, comprising administering to a subject in need thereof a pharmaceutical composition or an amorphous solid dispersion of any one of embodiments 1 to 242.

Embodiment 268. The method of embodiment 267, wherein the amorphous solid dispersion or the pharmaceutical composition comprises palbociclib or a salt thereof.

Embodiment 269. The method of embodiment 268, wherein the palbociclib or a salt thereof is administered with or without food.

Embodiment 270. The method of embodiment 267, wherein the method comprises administering palbociclib once daily in an amount equivalent to 125 mg of palbociclib free base per day for 21 days.

Embodiment 271. The method of embodiment 268, wherein the cancer is a solid cancer.

Embodiment 272. The method of embodiment 268, wherein the cancer is breast cancer.

Embodiment 273. The method of embodiment 272, wherein the cancer is metastatic breast cancer.

Embodiment 274. The method of embodiment 273, wherein the cancer is hormone receptor (HR)-positive, human epidermal growth factor receptor 2 (HER2)-negative advanced or metastatic breast cancer.

Embodiment 275. The method of embodiment 268, further comprising administering an aromatase inhibitor as initial endocrine based therapy in postmenopausal women.

Embodiment 276. The method of embodiment 275, wherein the aromatase inhibitor is anastrozole, exemestane, or letrozole.

Embodiment 277. The method of embodiment 268, further comprising administering fulvestrant, wherein the subject is a women with disease progression following endocrine therapy.

Embodiment 278. Use of the pharmaceutical composition or the amorphous solid dispersion of any one of embodiments 1 to 242 for the treatment of cancer in a subject.

Embodiment 279. The use of embodiment 278, wherein the amorphous solid dispersion or the pharmaceutical composition comprises palbociclib or a salt thereof.

Embodiment 280. The use of embodiment 279, wherein the palbociclib or a salt thereof is administered with or without food.

Embodiment 281. The use of embodiment 279, wherein palbociclib is administered once daily in an amount equivalent to 125 mg of palbociclib free base per day for 21 days.

Embodiment 282. The use of embodiment 279, wherein the cancer is a solid cancer.

Embodiment 283. The use of embodiment 279, wherein the cancer is breast cancer.

Embodiment 284. The use of embodiment 283, wherein the cancer is metastatic breast cancer.

Embodiment 285. The use of embodiment 284, wherein the cancer is hormone receptor (HR)-positive, human epidermal growth factor receptor 2 (HER2)-negative advanced or metastatic breast cancer.

Embodiment 286. The use of embodiment 279, wherein the pharmaceutical composition or the amorphous solid dispersion is used in combination with an aromatase inhibitor, and
wherein the aromatase inhibitor is an initial endocrine based therapy in postmenopausal women.

Embodiment 287. The use of embodiment 279, wherein the aromatase inhibitor is anastrozole, exemestane, or letrozole.

Embodiment 288. The use of embodiment 279, wherein the pharmaceutical composition or the amorphous solid dispersion is used in combination with fulvestrant, wherein the subject is a women with disease progression following endocrine therapy.

Embodiment 289. The method of embodiment 267, wherein the Cmax value of the API does not vary for more than 5%, 10%, 15%, 20%, 30%, 40% or 50% when the pharmaceutical compositions is administered in a fed or fasted state.

EXAMPLES

Disclosed herein are amorphous solid dispersions comprising an active pharmaceutical ingredient, one or more acids, and a hydrophilic high-molecular weight material. The amorphous solid dispersions were prepared via spray drying or vacuum drying. Preparation by vacuum drying was typically utilized for small, bench scale preparation. Spray drying techniques were utilized for intermediate and large scale preparations.

Example 1: Formulation of Small Scale Compositions of Palbociclib Amorphous Solid Dispersions (ASD)

The Vacuum Drying Process

The active pharmaceutical ingredient (palbociclib), one or more acids, optional additional excipients, and hydrophilic high molecular weight polymer were dissolved in a solvent or solvent mixture at a room temperature and optionally heated and/or sonicated to form a clear solution. The solution was sparged with dinitrogen gas while being stirred and heated above 35° C. to remove excess water. Heating, sparging, and stirring were halted when the solution became gelatinous. The vessel containing the gel was placed into a vacuum dryer and dried overnight at 40° C. and removed the next day to yield an amorphous solid dispersion.

Compositions of Palbociclib Amorphous Solid Dispersions with Acid and a Polymer

The following tables, Table 1 to Table 2, list the compositions of some of the amorphous solid dispersions that have been prepared by the bench top spray drying technique above. Dissolution of the amorphous solid dispersion systems SD-1 to SD-8 are shown in FIG. 1.

TABLE 1

| Formulation | SD-1 | SD-2 | SD-3 | SD-4 | SD-5* |
|---|---|---|---|---|---|
| API | Palbociclib - 125 mg | Palbociclib - 125 mg | Palbociclib - 125 mg | Palbociclib - 125 mg | Palbociclib - 125 mg |
| First Acid | Hydrochloric Acid - 15.3 mg | Hydrochloric Acid - 15.3 mg | Hydrochloric Acid - 10 mg | Hydrochloric Acid - 15.3 mg | None |
| Second Acid | Tartaric Acid - 50 mg | Tartaric Acid - 100 mg | Acetic Acid - 15 mg | None | Acetic Acid - 30 mg |
| Polymer | Copovidone - 100 mg | Copovidone - 100 mg | Copovidone - 100 mg | Copovidone - 100 mg | Copovidone - 100 mg |

*heated to 130° C.

TABLE 2

| Formulation | SD-6** | SD-7 | SD-8 |
|---|---|---|---|
| API | Palbociclib - 125 mg | Palbociclib - 125 mg | Palbociclib - 125 mg |
| First Acid | None | Hydrochloric Acid - 15.3 mg | None |
| Second Acid | Acetic Acid - 30 mg | Succinic Acid - 50 mg | Acetic Acid - 33.5 mg; Malic Acid - 50 mg |
| Polymer | Copovidone - 100 mg | Copovidone - 100 mg | Copovidone - 100 mg |

**heated to 180° C.

Example 2: Formulation of Intermediate and Large Scale Compositions of Palbociclib Amorphous Solid Dispersions (ASD)

The Spray Drying Processes Using a Bench Top Spray Dryer

The active pharmaceutical ingredient (palbociclib), acid pharmaceutical excipient(s), and polymer were dissolved in a solvent or solvent mixture at a room temperature and up to 45° C. to form a clear solution. A bench top spray dryer (Brand: LabPlant; Model #: SD-06AG, Manufacturer: Lab-Plant UK. Ltd.) was preheated until a steady state was achieved. The solution was then introduced into the spray dryer via flash atomization at a feed rate of about 3-10 rpm, at an inlet drying gas temperature of about 120-200° C., and an outlet temperature of about 63-93° C., and a pressure of about 2-3 bar. After collection, the particles were placed into a vacuum tray dryer operated at 60° C.

The Spray Drying Processes Using a Lab Scale Spray Dryer

The active pharmaceutical ingredient (palbociclib), acid pharmaceutical excipient(s), and polymer were dissolved in a solvent or solvent mixture at a room temperature and up to 45° C. to form a clear solution. A pilot scale spray dryer (Mobile Minor, GEA) was preheated until a steady state was achieved. The solution was then introduced into the spray dryer via flash atomization at a feed rate of about 35-50 rpm, at an inlet drying gas temperature of about 180-200° C., and an outlet temperature of about 80-85° C., and a pressure of about 4-6 bar. After collection, the particles were placed into a vacuum tray dryer operated at 60° C.

Compositions of Palbociclib Amorphous Solid Dispersions with a Strong Acid and a Polymer The following tables, Table 3 to Table 4, list the compositions of some of the amorphous solid dispersions that have been prepared by spray drying.

TABLE 3

| | Formulation 1 | | | Formulation 2 | | |
|---|---|---|---|---|---|---|
| | Amount in one dose (mg) | % in formulation | Amount during preparation (g) | Amount in one dose (mg) | % in formulation | Amount during preparation (g) |
| API | Palbociclib - 125 mg | 52.0% | 62.5 | Palbociclib - 125 mg | 53.1% | 6.25 |
| Strong Acid | HCl - 15.3 mg[1] | 6.4% | 7.7[2] | HCl - 10.2 mg[3] | 4.3% | 0.51[4] |
| Polymer | Copovidone - 100 mg | 42.6 % | 50.0 | HPMC E5LV - 100 mg | 42.5% | 5.00 |
| Total | 240.3 mg | 100% | 120.2 | 235.2 mg | 100% | 11.76 |
| Solvent | Removed after spray drying | | Water - 1000 g | Removed after spray drying | | Water - 49.9 g, Ethanol 49.9 g |

[1]The molar ratio of palbociclib and HCl is 1:1.5
[2]HCl was added as 20.8 g of 37% concentrated HCl
[3]The molar ratio of palbociclib and HCl is 1:1.0
[4]HCl was added as 1.38 g of 37% concentrated HCl

TABLE 4

| | Formulation 3 | | |
|---|---|---|---|
| | Amount in one dose (mg) | % in formulation | Amount during preparation (g) |
| API | Palbociclib - 125 mg | 49.6% | 6.25 |
| Strong Acid | MeSO$_3$H - 26.8 mg[1] | 10.6% | 1.34 |
| Polymer | HPMC E5LV - 100 mg | 39.7% | 5.00 |
| Total | 251.8 mg | 100% | 12.59 |
| Solvent | Removed after spray drying | | Water - 99.91 g |

[1]The molar ratio of palbociclib and methanesulfonic acid (MeSO$_3$H) is 1: 1

Figure 5:
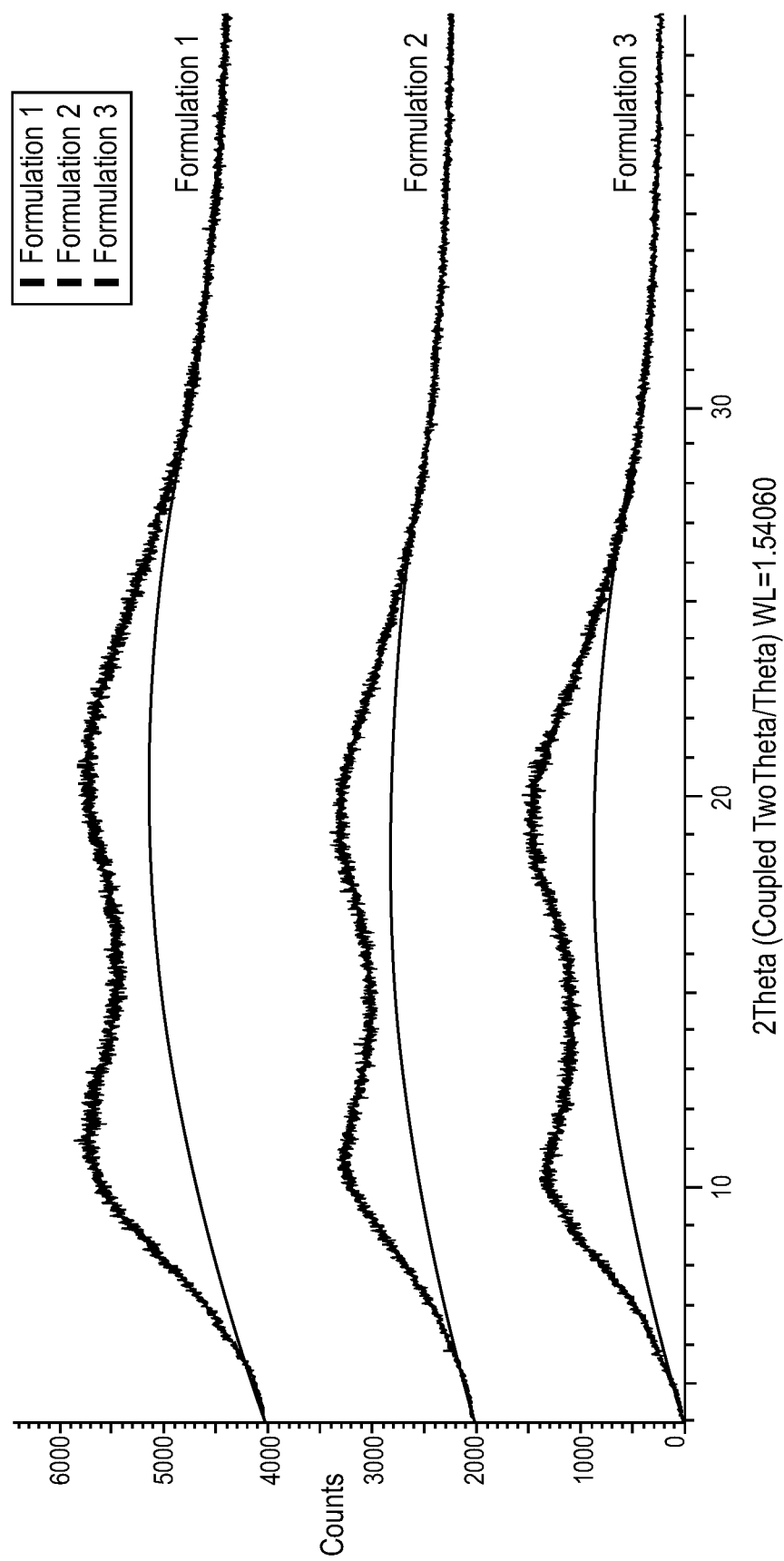
FIG. 5 shows the XRPD of palbociclib ASD Formulations 1, 2, and 3.

The amorphous solid dispersion powders of these three formulations in above two tables were shown to be amorphous in FIG. 5 by XRPD. The spray drying processes of these three formulations yielded greater than 30%.

Compositions of Palbociclib Amorphous Solid Dispersions with an Organic Acid and a Polymer The following tables, Table 5 to Table 6, list the compositions of some of the amorphous solid dispersions that have been prepared by spray drying of palbociclib an organic acid and a polymer solubilized in an aqueous solvent, per the preparation process shown in Example 2.

TABLE 5

| | Formulation 4 | | | Formulation 5 | | |
|---|---|---|---|---|---|---|
| | Amount in one dose (mg) | % in formulation | Amount during preparation (g) | Amount in one dose (mg) | % in formulation | Amount during preparation (g) |
| API | Palbociclib - 125 mg | 26.3 % | 12.5 | Palbociclib - 125 mg | 33.3% | 6.25 |
| Organic Acid | Tartaric Acid - 250 mg[1] | 52.6 % | 25.0 | Citric Acid - 150 mg[2] | 40.0% | 7.50 |
| Polymer | HPMC E5LV - 100 mg | 21.1% | 10.0 | Copovidone - 100 mg | 26.7% | 5.00 |
| Total | 475 mg | 100% | 47.5 | 375 mg | 100% | 18.75 |
| Solvent | Removed after spray drying | | Water - 427.5 g | Removed after spray drying | | Water - 308.75 g |

[1]The weight ratio of palbociclib and tartaric acid is 1:2, and the molar ratio of them is 1:6
[2]The weight ratio of palbociclib and citric acid is 1:1.2, and the molar ratio of them is 1:2.8

TABLE 6

| | Formulation 6 | | |
|---|---|---|---|
| | Amount in one dose (mg) | % in formulation | Amount during preparation (g) |
| API | Palbociclib - 125 mg | 38.2% | 18.75 |
| Organic Acid | Tartaric Acid - 100 mg | 30.5% | 15.00 |
| Polymer | Copovidone - 100 mg | 30.5% | 15.00 |
| Antioxidant | BHA - 2 mg, BHT - 0.4 mg | BHA - 0.6%, BHT - 0.1% | BHA - 0.3 g, BHT - 0.06 g |
| Total | 327.4 mg | 100% | 49.11 |
| Solvent | Removed after spray drying | | Ethanol - 711 g Water - 900 g |

[1]The weight ratio of palbociclib and tartaric acid is 1:0.8, and the molar ratio of them is 1:2.4

The solid content, the percentage of the total amount of solutes in the spray drying solution, of Formulation 4 was 10.0%, of Formulation 5 was 5.7%, and of Formulation 6 was 3.0%.

Figure 6:
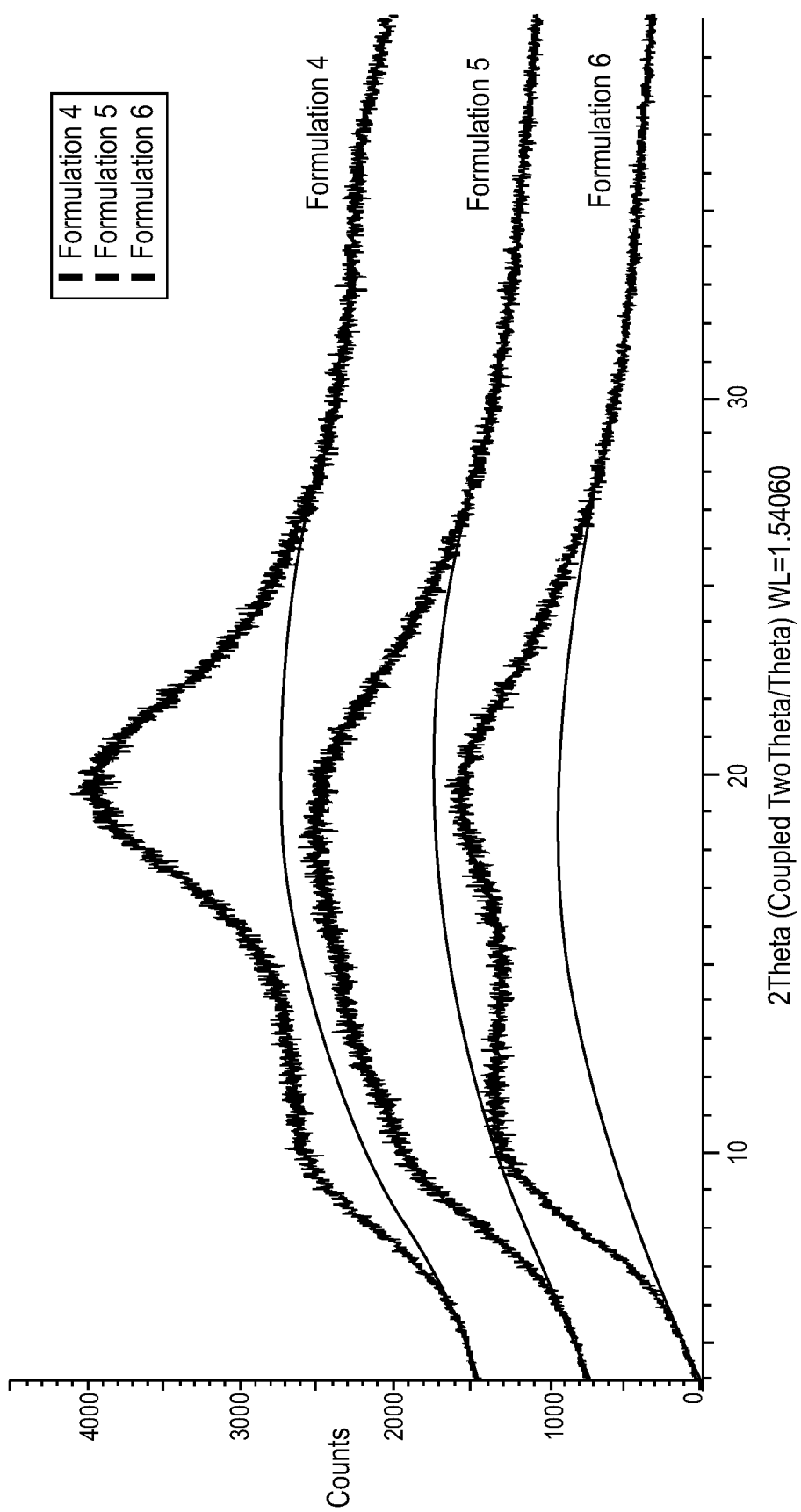
FIG. 6 shows the XRPD of palbociclib ASD Formulations 4, 5, and 6.

The amorphous solid dispersion powders of these three formulations were shown to be amorphous in FIG. 6 by XRPD. The yield of the spray drying process of Formulation 4 was less than 30%. The yield of Formulation 5 and Formulation 6 was more than 30%.

The antioxidants present in the amorphous solid dispersion powder of Formulation 6 are optional.

Compositions of Palbociclib Amorphous Solid Dispersions with a Strong Acid, an Organic Acid and a Polymer The following tables, Table 7 to Table 10, list the compositions of some of the amorphous solid dispersions that have been prepared by spray drying. In these examples, HCl or methanesulfonic acid was used as the first acid to dissolve palbociclib free base in an aqueous solvent (water or water alcohol mixture). The second acid and a polymer were further dissolved in the solution at room temperature or heated up to 45° C. The solutions were spray dried in either a bench top spray dryer (Formulation 7 to Formulation 10)

or a lab scale spray dryer (Formulation 11 to Formulation 13), according to the spray drying processes described in Example 2.

TABLE 7

|  | Formulation 7 | | | Formulation 8 | | |
|---|---|---|---|---|---|---|
|  | Amount in one dose (mg) | % in formulation | Amount during preparation (g) | Amount in one dose (mg) | % in formulation | Amount during preparation (g) |
| API | Palbociclib - 125 mg | 36.7% | 125.0 | Palbociclib - 125 mg | 36.7% | 7.50 |
| First Acid | HCl - 15.3 mg[1] | 4.5% | 15.3[2] | HCl - 15.3 mg[1] | 4.5% | 0.92[2] |
| Second Acid | Tartaric Acid - 100 mg[3] | 29.4% | 100.0 | Tartaric Acid - 100 mg[3] | 29.4% | 6.00 |
| Polymer | Copovidone - 100 mg | 29.4% | 100.0 | PVP K30 - 100 mg | 29.4% | 6.00 |
| Total | 340.3 mg | 100% | 340.3 | 340.3 mg | 100% | 20.42 |
| Solvent | Removed after spray drying | | Water - 2000 g | Removed after spray drying | | Water - 120 g |

[1] The molar ratio of palbociclib and HCl is 1:1.5
[2] HCl was added as 41.4 g of 37 % concentrated HCl in Formulation 7 and as 2.49 g of 37 % concentrated HCl in Formulation 8
[3] The weight ratio of palbociclib and tartaric acid is 1:0.8, and the molar ratio of them is 1:2.4

TABLE 8

|  | Formulation 9 | | | Formulation 10 | | |
|---|---|---|---|---|---|---|
|  | Amount in one dose (mg) | % in formulation | Amount during preparation (g) | Amount in one dose (mg) | % in formulation | Amount during preparation (g) |
| API | Palbociclib - 125 mg | 36.7% | 5.00 | Palbociclib - 125 mg | 43.1% | 62.5 |
| First Acid | HCl - 15.3 mg[1] | 4.5% | 0.61[2] | HCl - 15.3 mg[1] | 5.3% | 7.65[2] |
| Second Acid | Tartaric Acid - 100 mg[3] | 29.4% | 4.00 | Tartaric Acid - 50 mg[4] | 17.2% | 25.0 |
| Polymer | HPMC E5LV - 100 mg | 29.4% | 4.00 | Copovidone - 100 mg | 34.4% | 50.0 |
| Total | 340.3 mg | 100% | 13.61 | 290.3 mg | 100% | 145.15 |
| Solvent | Removed after spray drying | | Water - 80 g | Removed after spray drying | | Water - 1000 g |

[1] The molar ratio of palbociclib and HCl is 1:1.5
[2] HCl was added as 1.65 g of 37% concentrated HCl in Formulation 9 and as 20.68 g of 37 % concentrated HCl in Formulation 10
[3] The weight ratio of palbociclib and tartaric acid is 1:0.8, and the molar ratio of them is 1:2.4
[4] The weight ratio of palbociclib and tartaric acid is 1:0.4, and the molar ratio of them is 1:1.2

TABLE 9

|  | Formulation 11 | | | Formulation 12 | | |
|---|---|---|---|---|---|---|
|  | Amount in one dose (mg) | % in formulation | Amount during preparation (g) | Amount in one dose (mg) | % in formulation | Amount during preparation (g) |
| API | Palbociclib - 125 mg | 36.7% | 250.0 | Palbociclib - 125 mg | 35.5% | 625.0 |
| First Acid | HCl - 15.3 mg[1] | 4.5% | 30.6[2] | MeSO$_3$H - 26.8 mg[3] | 7.6% | 138.5 |
| Second Acid | Tartaric Acid - 100 mg[4] | 29.4% | 200.0 | Tartaric Acid - 100 mg[4] | 28.4% | 500.0 |

TABLE 9-continued

| | Formulation 11 | | | Formulation 12 | | |
|---|---|---|---|---|---|---|
| | Amount in one dose (mg) | % in formulation | Amount during preparation (g) | Amount in one dose (mg) | % in formulation | Amount during preparation (g) |
| Polymer | Copovidone - 100 mg | 29.4% | 200.0 | HPMC E5LV - 100 mg | 28.4% | 500.0 |
| Total Solvent | 340.3 mg | 100% Removed after spray drying | 680.6 Ethanol - 1580 g Water - 2000 g | 351.8 mg | 100% Removed after spray drying | 1763.5 Water - 9070 g |

[1] The molar ratio of palbociclib and HCl is 1:1.5
[2] HCl was added as 82.7 g of 37% concentrated HCl in Formulation 11
[3] The molar ratio of palbociclib and methanesulfonic acid (MeSO$_3$H) is 1:1
[4] The weight ratio of palbociclib and tartaric acid is 1:0.8, and the molar ratio of them is 1:2.4

Antioxidants are optionally added in amorphous solid dispersions of palbociclib, as shown in Table 10 (Formulation 13).

TABLE 10

| | Formulation 13 | | |
|---|---|---|---|
| | Amount in one dose (mg) | % in formulation | Amount during preparation (g) |
| API | Palbociclib - 125 mg | 36.5% | 1125 |
| First Acid | HCl - 15.3 mg[1] | 4.5% | 137.7[2] |
| Second Acid | Tartaric Acid - 100 mg | 29.2% | 900 |
| Polymer | Copovidone - 100 mg | 29.2% | 900 |
| Antioxidant | BHA - 2 mg, BHT - 0.4 mg | BHA - 0.6%, BHT - 0.1% | BHA - 18 g, BHT - 3.6 g |
| Total Solvent | 342.7 mg | 100% Removed after spray drying | 3084.3 Ethanol - 7110 g Water - 9000 g |

Figure 7:
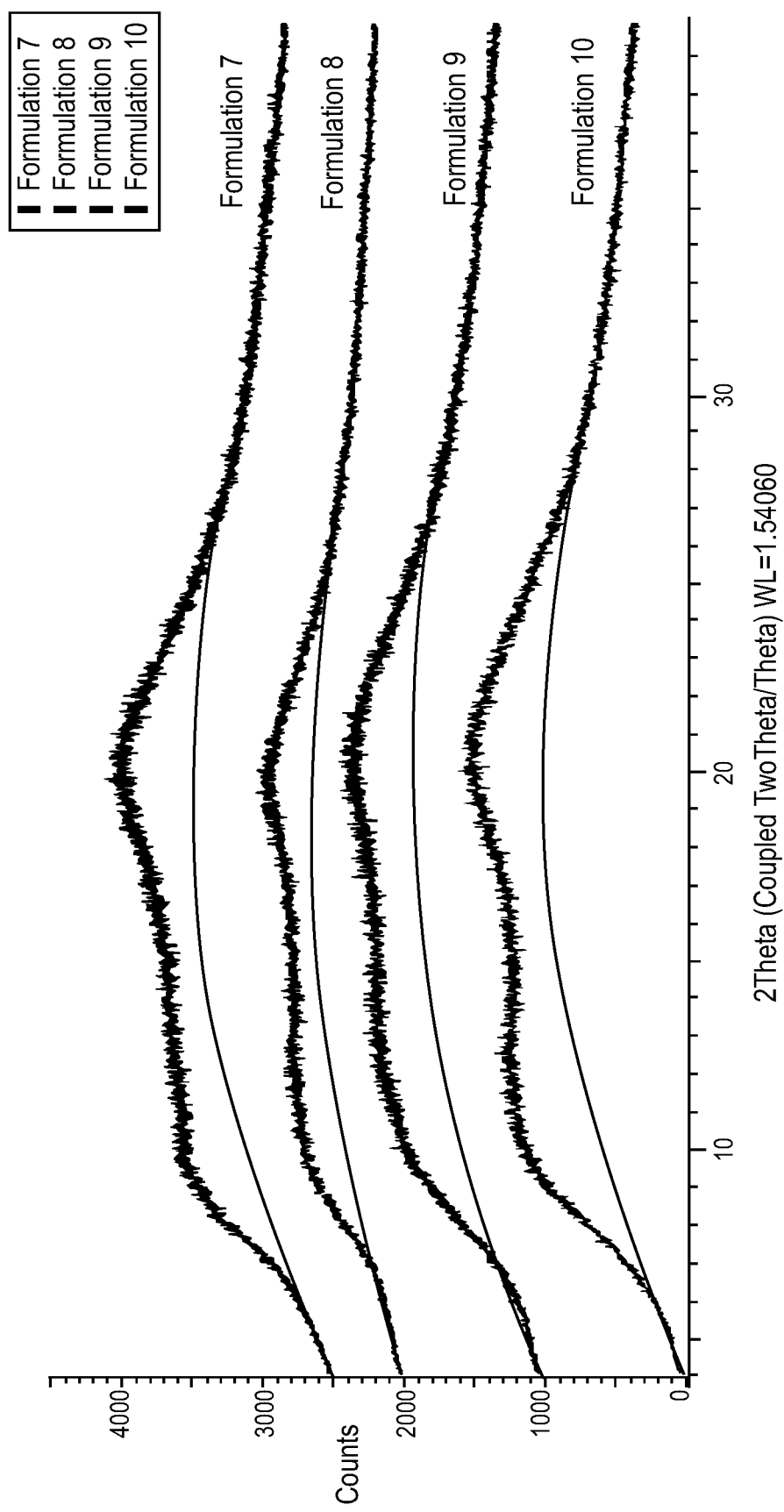
FIG. 7 shows the XRPD of palbociclib ASD Formulations 7, 8, 9, and 10.
Figure 8:
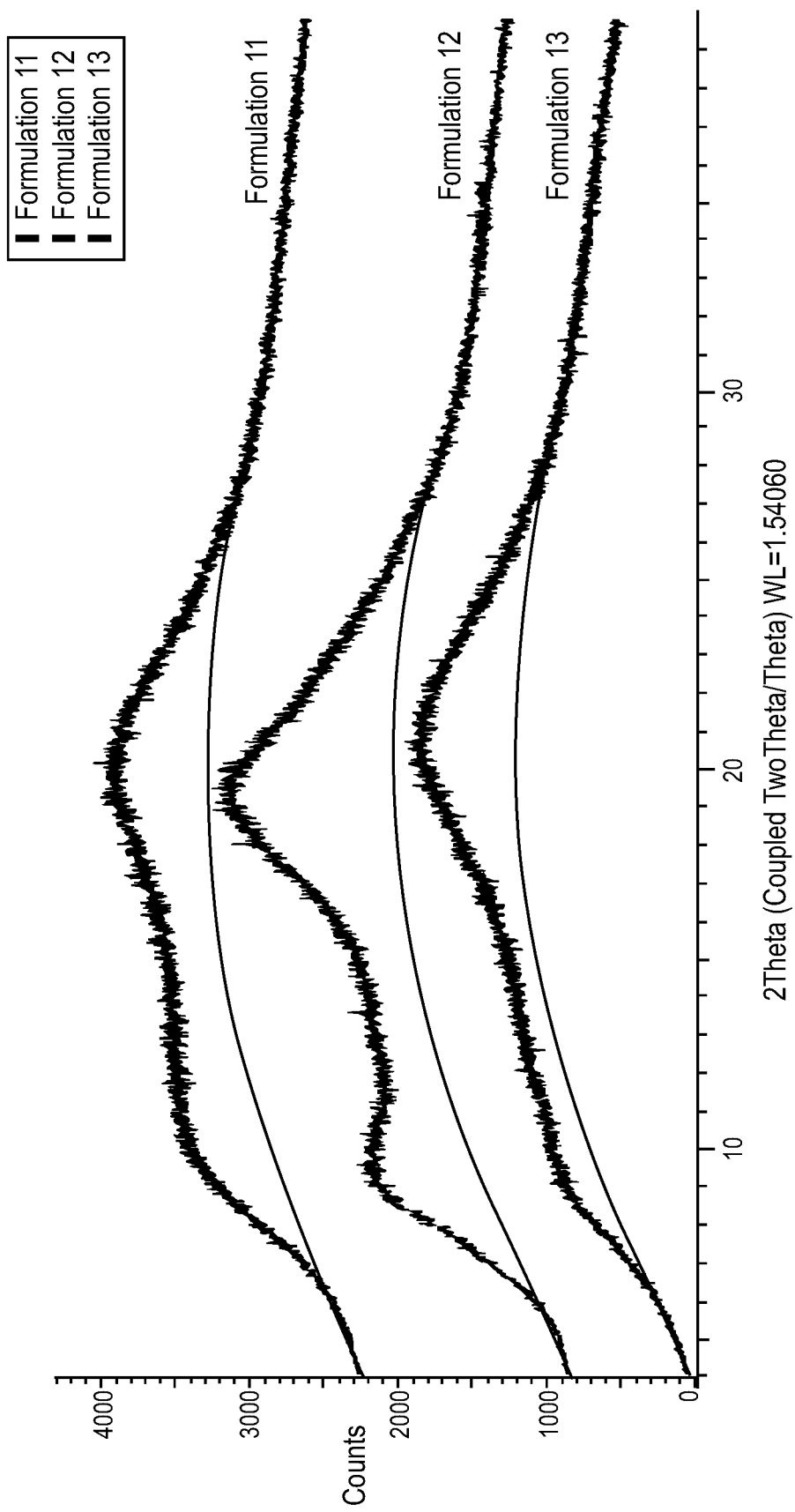
FIG. 8 shows the XRPD of palbociclib ASD Formulations 11, 12, and 13.

[1] The molar ratio of palbociclib and HCl is 1:1.5
[2] HCl was added as 372.2 g of 37% concentrated HCl The amorphous solid dispersion powders of the formulations in the above tables were shown to be amorphous in FIG. 7 and FIG. 8 by XRPD. The yields of the spray drying processes of these formulations were more than 30%. In addition, Formulation 11, Formulation 12 and Formulation 13 were prepared by a lab scale spray dryer, at a larger batch scale, indicating that the spray drying processes are scalable. Compositions of Amorphous Solid Dispersion of Palbociclib Salt Palbociclib mesylate salt was first prepared by the following process.

In a beaker with the mixture of 1275.2 grams of acetonitrile and 283.2 grams of purified water, 500 grams of palbociclib free base was added and mixed well in the solvent. Additionally, 108.3 grams of methanesulfonic acid was added and the suspension was stirred for 24 hours. The solid was collected by filtration and then dried at 60° C. under vacuum for 15 hours. The final solid was tested by NMR and sulfur elementary analysis, and the result was found to match stoichiometrically with the structure of palbociclib mesylate.

The palbociclib mesylate salt was further used to prepare the amorphous solid dispersion following the composition of Formulation 14 in Table 11 and the process shown in Example 2 by a bench top spray dryer.

TABLE 11

| | Formulation 14 | | |
|---|---|---|---|
| | Amount in one dose (mg) | % in formulation | Amount during preparation (g) |
| API | Palbociclib Mesylate- 151.8 mg | 43.1% | 1.52 |
| Organic Acid | Tartaric Acid - 100 mg | 28.4% | 1.0 |
| Polymer | Copovidone - 100 mg | 28.4% | 1.0 |
| Total Solvent | 351.8 mg | 100% Removed after spray drying | 3.52 Water - 19.93 g |

Figure 9:
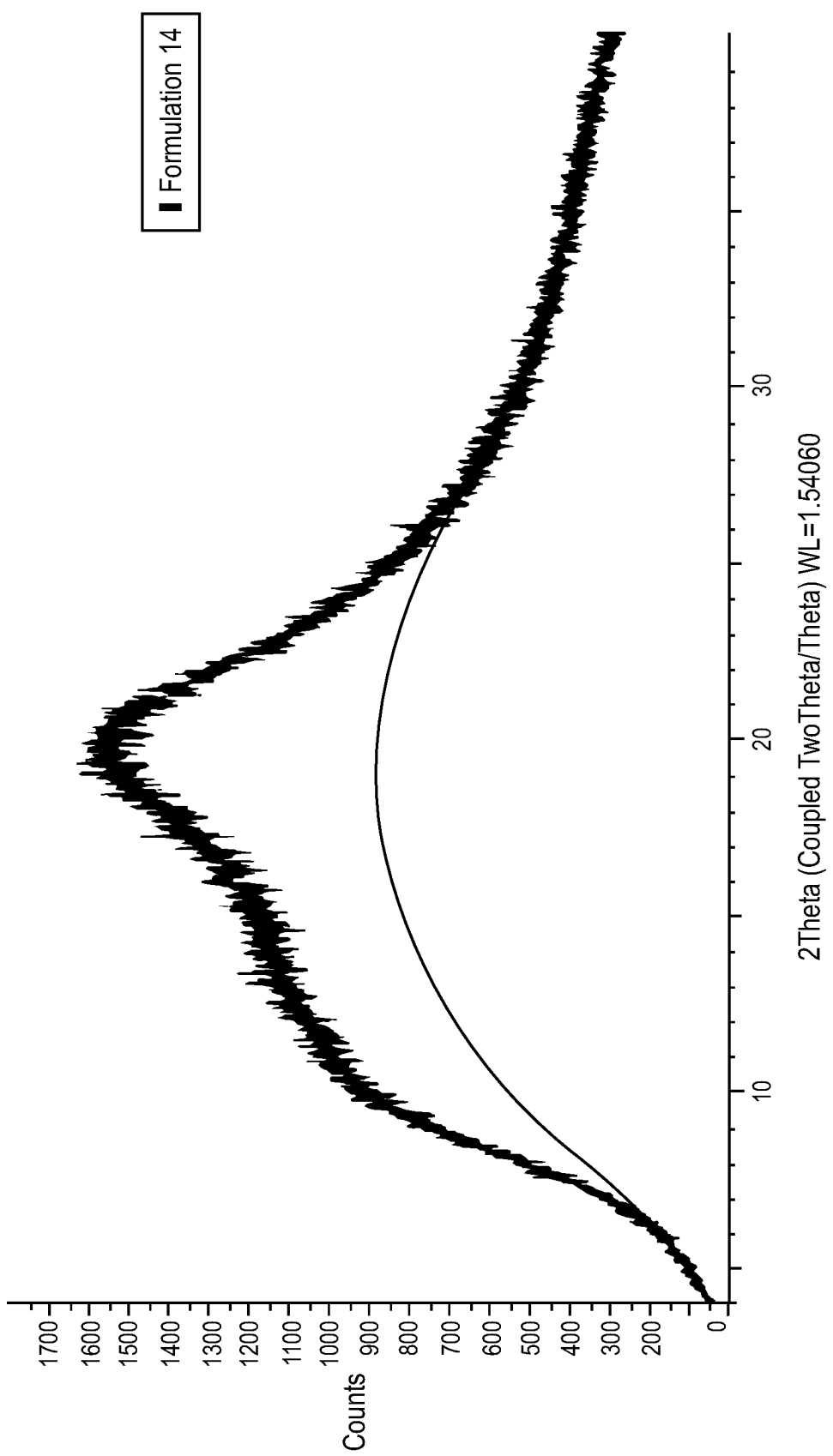
FIG. 9 shows the XRPD of ASD Formulation 14.

The amorphous solid dispersion powders of the formulations in the above table was shown to be amorphous in FIG. 9 by XRPD. This example shows that the first acid, could be used as part of salt of the drug substance, or could be used during the preparation of amorphous solid dispersions, as shown in Formulation 12.

Example 3: Capsule Formulations of Palbociclib Amorphous Solid Dispersions

Some of the amorphous solid dispersions of palbociclib shown in Examples 2 were further processed into capsule formulations, following Table 12 and Table 13.

The formulations in Table 12 were prepared by mixing the relative amounts of amorphous solid dispersions with other excipients for dry granulation. The dry granulation was performed by slugging, milling and screening to form dry granules and then hand filled into Size 0 gelatin capsules. The manufacturing workflow employed is generally summarized in FIG. 2 These capsule formulations were used to assess their in vitro dissolution and in vivo exposure in dogs and humans, as shown in the later Examples 5 and 6.

TABLE 12

| | Formulation 15 | Formulation 16 | Formulation 17 | Formulation 18 |
|---|---|---|---|---|
| Dry granulation materials | Formulation 1 ASD - 240.3 mg crospovidone - 23.3 mg MCC KG802 - 46.5 mg | Formulation 6 ASD - 327.4 mg crospovidone - 23.3 mg MCC KG802 - 49.8 mg | Formulation 10 ASD - 290.3 mg crospovidone - 23.3 mg MCC KG802 - 46.5 mg | Formulation 11 ASD - 340.3 mg crospovidone - 23.3 mg MCC KG802 - 46.5 mg |

TABLE 12-continued

|  | Formulation 15 | Formulation 16 | Formulation 17 | Formulation 18 |
| --- | --- | --- | --- | --- |
|  | Lactose - 41.2 mg | Lactose - 42.5 mg | Lactose - 41.2 mg | Lactose - 41.2 mg |
|  | Silica - 9.3 mg | Silica - 4.7 mg | Silica - 9.3 mg | Silica - 9.3 mg |
|  | MgSt - 4.7 mg | MgSt - 4.7 mg | MgSt - 4.7 mg | MgSt - 4.7 mg |
| Total weight | 365.3 mg | 452.4 mg | 415.3 mg | 465.3 mg |

The formulations in Table 13 were prepared by mixing the relative amounts of amorphous solid dispersions with "additional dry granulation materials" for dry granulation. The dry granulation was performed by roller compaction, milling and screening to form dry granules, further mixed with additional lubricant and then filled into Size 0 HPMC capsules by an encapsulation machine. These capsule formulations were used to assess their in vitro dissolution and in vivo exposure in human, as shown in the later Example 6.

TABLE 13

|  | Formulation 19 | Formulation 20 |
| --- | --- | --- |
| Dry granulation materials | Formulation 13 ASD - 342.7 mg crospovidone - 23.3 mg MCC KG802 - 41.7 mg Lactose - 42.6 mg Silica - 4.7 mg MgSt - 2.35 mg | Formulation 12 ASD - 351.8 mg crospovidone - 23.3 mg MCC KG802 - 25.5 mg L-Tartaric Acid - 55.0 mg Silica - 4.7 mg MgSt - 2.35 mg |
| External Excipient | MgSt - 2.35 mg | MgSt - 2.35 mg |
| Total weight | 459.7 mg | 465.0 mg |

Compositions of Amorphous Solid Dispersion of Palbociclib with a Surfactant

The amorphous solid dispersion of palbociclib containing a surfactant was prepared by the composition of Formulation 21 in Table 14 and the process shown in Example 1 by a bench top spray dryer. In this example, lecithin was used as a surfactant. Since lecithin is not soluble in water at the composition shown in the formulation table, the pre-spray drying solution is actually an emulsion.

TABLE 14

| | Formulation 21 | | |
| --- | --- | --- | --- |
|  | Amount in one dose (mg) | % in formulation | Amount during preparation (g) |
| API | Palbociclib - 125 mg | 31.1% | 12.5 |
| Strong Acid | MeSO$_3$H - 26.8 mg$^3$ | 6.7% | 2.68 |
| Organic Acid | Tartaric Acid - 100 mg$^4$ | 24.9% | 10.0 |
| Polymer | HPMC E5LV - 100 mg | 24.9% | 10.0 |
| Surfactant | Lecithin - 50 mg | 12.4 | 5.0 |
| Total | 401.8 mg | 100% | 40.18 |
| Solvent | Removed after spray drying | | Water - 209.8 g |

Figure 10:
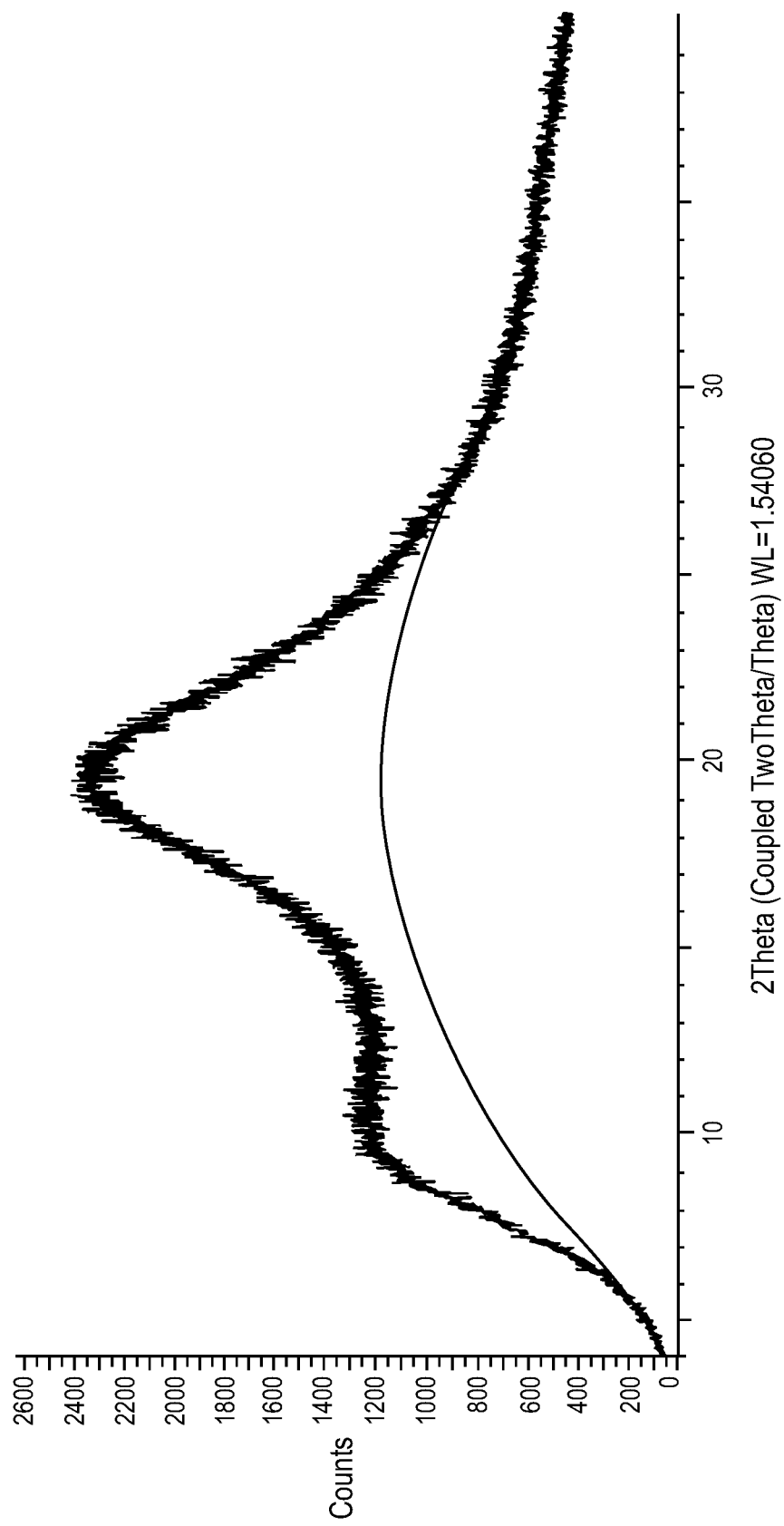
FIG. 10 shows the XRPD of ASD Formulation 21.

The amorphous solid dispersion powders of the formulations in the above table was shown to be completely amorphous in FIG. 10 by XRPD. This example shows that a surfactant, such as lecithin, could be added as part of the amorphous solid dispersion, as shown in the above formulation.

Example 4: In Vitro Performance and Comparisons of Palbociclib ASD Formulations

Figure 11:
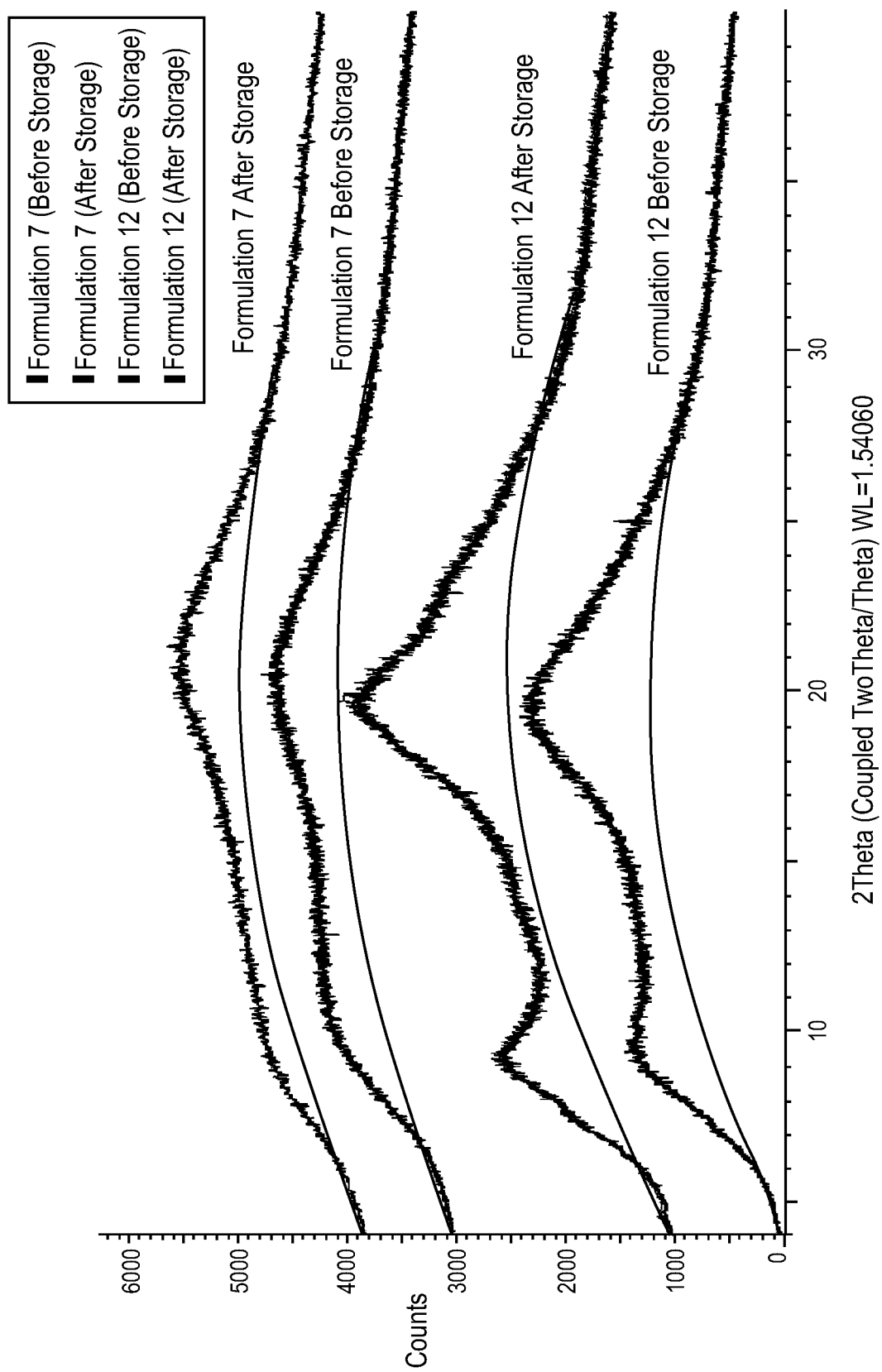
FIG. 11 shows the comparison of XRPD profiles of palbociclib ASD capsule Formulations 7 and 12 before and after storage.

Physical Stability of Palbociclib Amorphous Solid Dispersions and Capsule Formulations Palbociclib amorphous solid dispersions (ASD) (Formulation 7 and Formulation 12) were assessed for their long-term physical stability. When the ASD formulations were dried to less than 4% of moisture, encapsulated in HPMC capsules and stored in sealed HDPE bottles with desiccant under 40° C. and 75% RH, the ASD formulations were shown to be amorphous by XRPD after six months, as shown in FIG. 11.

Figure 12:
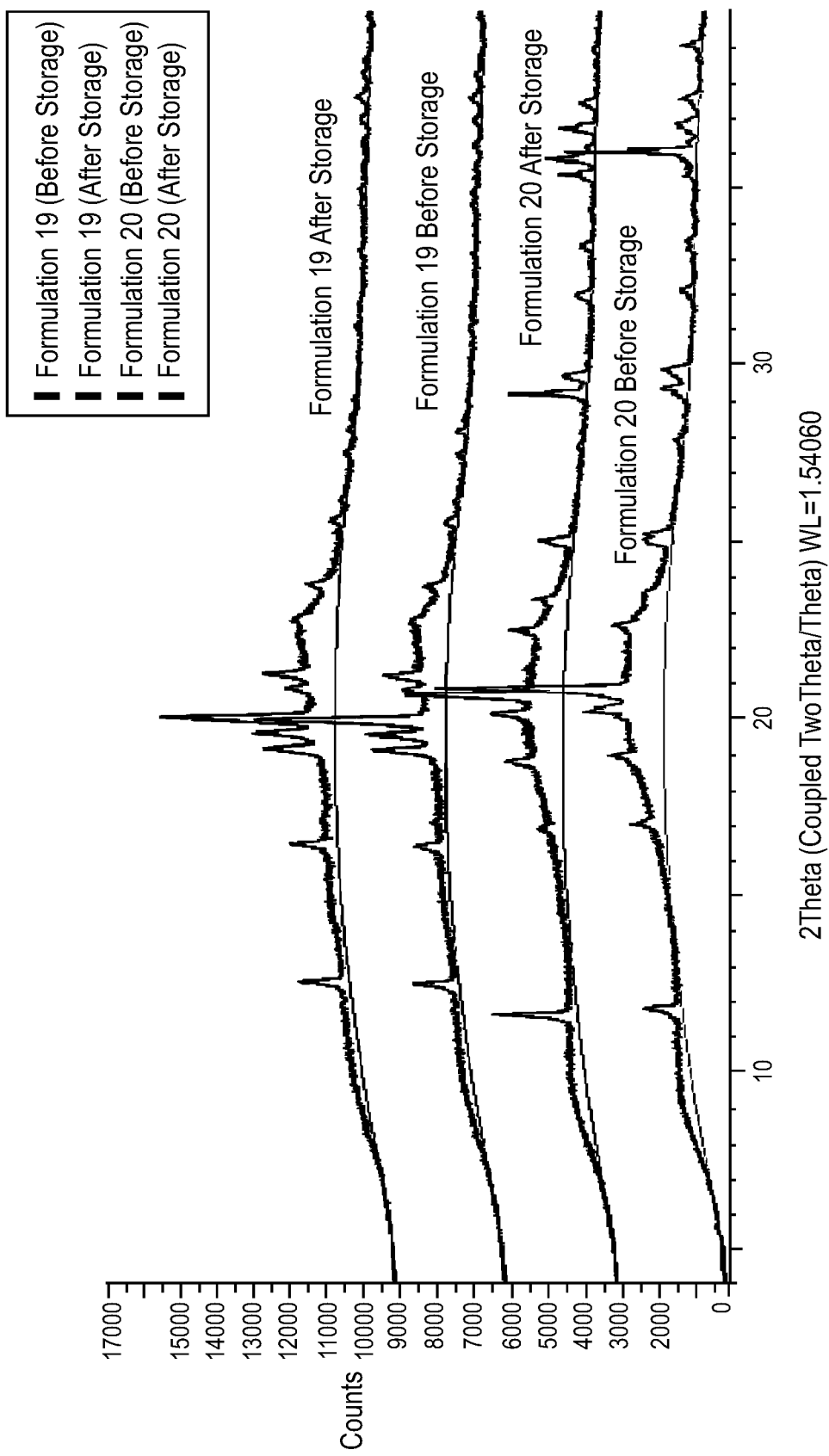
FIG. 12 shows the comparison of XRPD Profiles of palbociclib ASD capsule Formulations 19 and 20 before and after storage.

Capsule formulations of palbociclib ASD (Formulation 19 and Formulation 20) were assessed for their long-term physical stability. When the capsule formulations were controlled to less than 6% of moisture, encapsulated in HPMC capsules and stored in sealed HDPE bottles with desiccant under 40° C. and 75% RH, no additional XRPD peaks shown after six months, as shown in FIG. 12, showing that the capsule formulations are physically stable.

Kinetic Solubility Profiles of Palbociclib ASD Powders

The kinetic solubility profiles of different compositions of palbociclib ASD powders were assessed. The kinetic solubility profiles were performed by adding palbociclib ASD powders (containing 125 mg of palbociclib free base) into 300 ml of pH 6.5 phosphate buffer solution in a dissolution bath at 37 C and stirred at 200 rpm. The concentrations of palbociclib in the solution at different time points were determined by a HPLC method.

The kinetic solubility profiles ASD formulations of palbociclib with acidic excipients and polymer were compared with a reference ASD formulation of palbociclib without acidic excipient. This reference ASD was prepared by dissolving palbociclib free base API and the polymer PVP/VA 64 (the weight ratio of API and the polymer is 125:100) in an acetic acid aqueous solution (the weight ratio of API and acetic acid is 125:33.5 which is equivalent to molar ratio of 1:2). The total solid content in this solution is about 16%. The processing condition shown in Example 2 was applied to prepare this reference. Acetic acid in the solution was dried off during the spray drying process. Therefore, the material is a simple amorphous solid dispersion of the API and the polymer. This ASD was amorphous as determined by XRPD.

Figure 13:
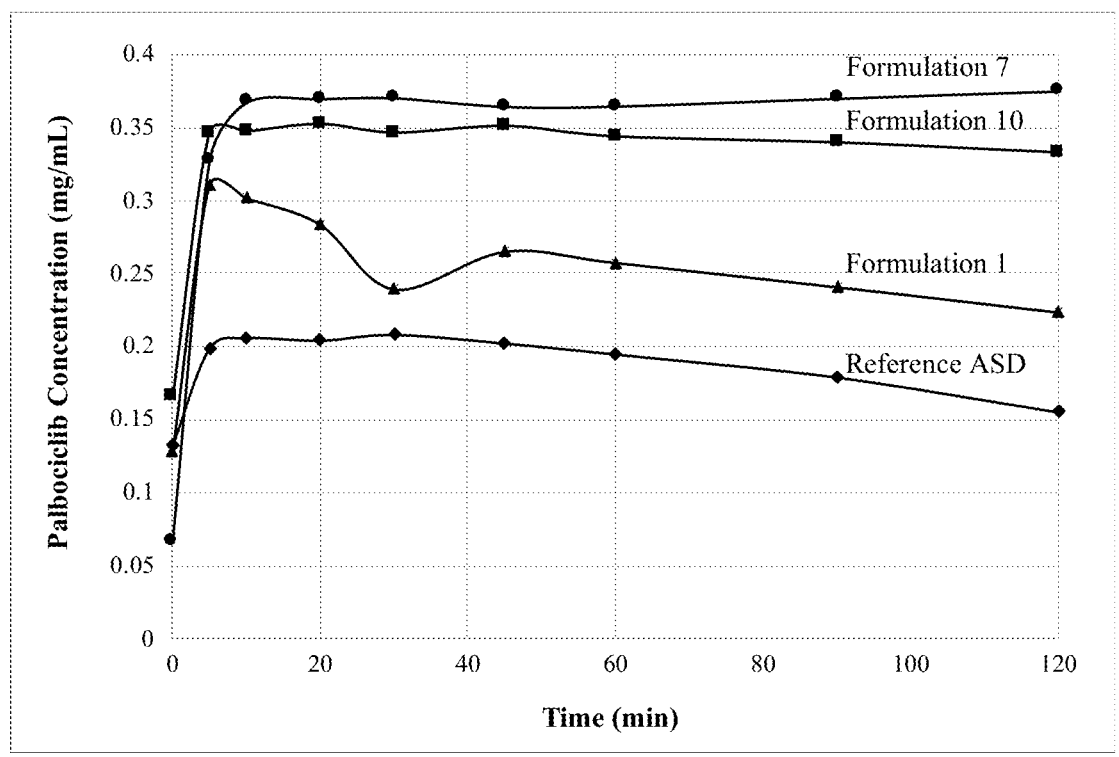
FIG. 13 shows the kinetic solubility of palbociclib ASD powders.

The comparison of the kinetic solubility profiles is shown in FIG. 13. The solubility of palbociclib crystalline free base is less than 0.01 mg/mL. The kinetic solubility of the reference ASD was improved, in comparison to the crystalline palbociclib. However, the ASD reference was significantly lower than the ASD containing an acidic excipient. The dissolution experiments also showed that the ASD of Formulation 7 was superior to Formulation 10. Formulation 10 had half of the tartaric acid of formulation 7.

The data of FIG. 13 are presented in termed of the concentration of dissolved palbociclib. These data may also be presented in terms of percent of palbociclib dissolved. Formulation 7 was shown to have a percent dissolution of approximately 88%.

In Vitro Dissolutions of Palbociclib Capsule Formulations

Several palbociclib formulations were assessed for their in vitro dissolution profiles. In this study, Formulation 18 was used to represent the amorphous solid dispersion of palbociclib with acidic excipients. The in vitro dissolution profile of this formulation was compared to the following three reference formulations.

Reference 1 is a capsule formulation of the reference ASD without any acidic component. Reference 1 was an ASD of 125 mg palbociclib and 100 mg of PVP/VA 64. Additional excipients similar to Table 12 were used to form dry granules and the granules were then filled into capsules. This formulation was prepared to represent a simple ASD formulation of palbociclib and a hydrophilic polymer.

Reference 2 is a conventional wet granulation formulation of palbociclib with an acidic excipient. Crystalline palbociclib free base API and tartaric acid (the weight ratio of API and the polymer is 125:100), in combination with other conventional excipients, were wet granulated and encapsulated. This formulation was prepared to represent a simple conventional formulation of palbociclib with simple mixture of an acidic excipient.

Reference 3 is IBRANCE®, which is the currently approved product on the market.

The dissolutions were performed in 900 ml of pH 6.5 phosphate buffer at 37° C., with a paddle method at 50 rpm and a sinker to hold the capsules in the dissolution media.

Figure 14:
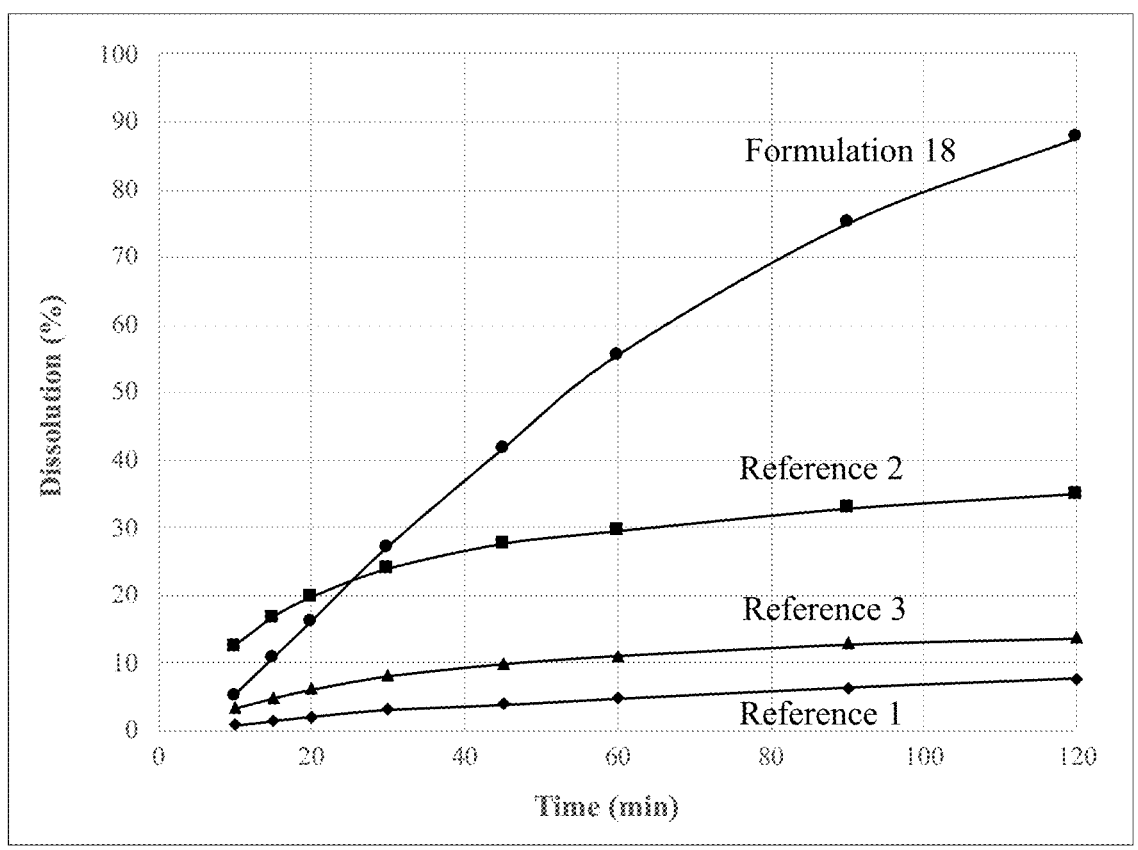
FIG. 14 shows the dissolution profiles of different palbociclib formulations.

As shown in FIG. 14, Formulation 19, the capsule formulation of palbociclib ASD with acidic excipients, showed a significantly higher dissolution, in comparison to the profiles of the three reference formulations.

Example 5: In Vivo Performance in Dogs and Comparisons of Palbociclib ASD Formulations Dog Pharmacokinetic Study of IBRANCE® Under Different Doing Pretreatments The reference product, IBRANCE® capsule, was tested orally in six Beagle dogs under three different dosing pretreatments, using a three-way crossover design. These three dosing pretreatments included an intramuscular injection of 6 μg/kg pentagastrin 45 minutes prior to dosing (labeled as Acidified Group in the results), an intravenous injection of 50 mg ranitidine hydrochloride 60 minutes prior to dosing (labeled as Antacid Group in the results), and feeding of 100 g of dog food, which is evenly mixed with 16.4 g hot butter (about 500 calories) (labeled as Fed Group in the results). During the study, the dogs were allowed to drink water freely and were fasted for 12 hours before administration. Except for the fed group, all dogs are given food 4 hours after drug administration. One IBRANCE® 125 mg capsule was given to each dog and was administered together with 50 ml water.

Blood samples were taken from each group of animals at the following time points: 0 h (before test drug administration), and 0.5, 1.0, 1.5, 2.0, 3.0, 4.0, 6.0, 8.0, 12, 24, 32 and 48 h after the drug administration. Palbociclib plasma concentrations were analyzed by an LC-MS/MS method. The non-compartment model of software WinNonlin was used to calculate the pharmacokinetic parameters of each dog, $C_{max}$, $AUC_t$ and $AUC_{inf}$. The geometric averages of each parameters were used for comparisons of the in vivo absorption under different doing pretreatments.

Table 15 shows the geometric mean values as well as coefficient of variation (CV) of the pharmacokinetic parameters of three dosing groups, and Table 16 shows the geometric mean ratios of the pharmacokinetic parameters of these three dosing groups.

TABLE 15

|  |  | Cmax ng/mL | AUClast h * ng/mL | AUCINF_obs h * ng/mL |
|---|---|---|---|---|
| Acidified (R1) | Geo Mean | 735.6 | 16451.7 | 18211.0 |
|  | CV (%) | 28.8% | 21.4% | 24.0% |
| Fed (R2) | Geo Mean | 724.7 | 16237.8 | 18490.3 |
|  | CV (%) | 39.5% | 34.7% | 34.5% |
| Antiacid (R3) | Geo Mean | 195.6 | 4940.8 | 7439.7 |
|  | CV (%) | 81.1% | 71.4% | 64.2% |

TABLE 16

| Geometric Mean Ratio | Cmax | AUClast | AUCINF_obs |
|---|---|---|---|
| R2/R1 | 98.5% | 98.7% | 101.5% |
| R3/R1 | 26.6% | 30.0% | 40.9% |
| R3/R2 | 27.0% | 30.4% | 40.2% |

Figure 15:
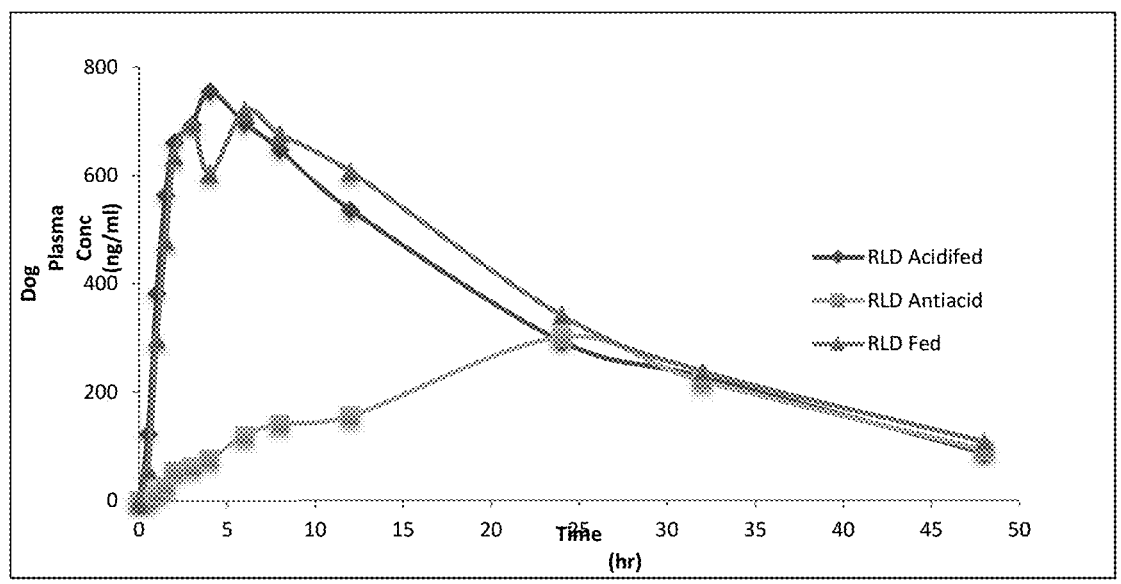
FIG. 15 shows the mean dog plasma palbociclib profiles of IBRANCE® after different dosing pretreatments.

The results in these two tables show that when IBRANCE® is co-administered with an anti-acid product, its in vivo exposure is significantly reduced. The mean plasma profiles of palbociclib concentration of these three groups are shown in FIG. 15.

Dog Pharmacokinetic Study of a Palbociclib ASD Formulation (Formulation 18) Under Different Dosing Pretreatments A palbociclib ASD capsule formulation, Formulation 18, was tested orally in six Beagle dogs under three different dosing pretreatments, using a three-way crossover design. The experimental design was exactly the same as that has described for the IBRANCE® dog study.

Table 17 shows the geometric mean values as well as coefficient of variation (CV) of the pharmacokinetic parameters of three dosing groups, and Table 18 shows the geometric mean ratios of the pharmacokinetic parameters of these three dosing groups.

TABLE 17

|  |  | Cmax ng/mL | AUClast h * ng/mL | AUCINF_obs h * ng/mL |
|---|---|---|---|---|
| Acidified (T1) | Average | 884.7 | 19278.4 | 22667.6 |
|  | CV (%) | 25.2% | 28.1% | 27.4% |
| Fed CM | Average | 811.0 | 18455.8 | 21308.8 |
|  | CV (%) | 19.3% | 14.7% | 16.5% |
| Antiacid (T3) | Average | 816.3 | 18168.3 | 20677.5 |
|  | CV (%) | 17.7% | 20.0% | 20.1% |

TABLE 18

| Geometric Mean Ratio | Cmax | AUClast | AUCINF_obs |
|---|---|---|---|
| T2/T1 | 91.7% | 95.7% | 94.0% |
| T3/T1 | 92.3% | 94.2% | 91.2% |
| T3/T2 | 100.7% | 98.4% | 97.0% |

Figure 16:
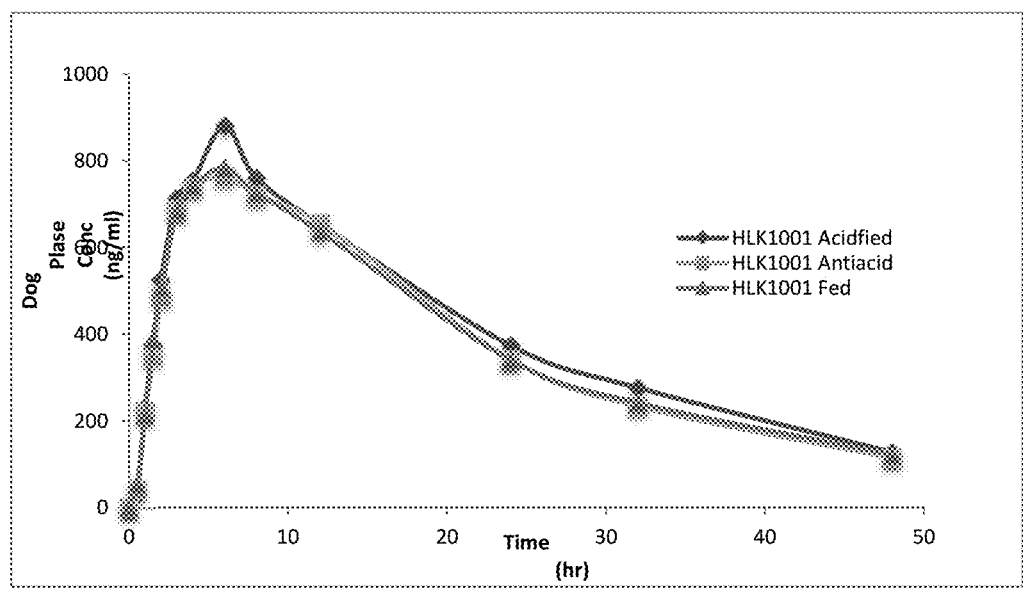
FIG. 16 shows the mean dog plasma palbociclib profiles of Formulation 18 after different dosing pretreatments.

The results in these two tables show that when palbociclib ASD capsule formulation, Formulation 18, is co-administered with an anti-acid product, its in vivo exposure is not significantly affected. The mean plasma profiles of palbociclib concentration of these three groups are shown to be similar among each other in FIG. 16.

Comparison of Dog Pharmacokinetic Parameters of Palbociclib ASD Formulations with Different Level of Tartaric Acid Palbociclib ASD formulations with different levels of the organic acid excipient were also tested in a dog study with a three-way crossover design to assess the in vivo exposure affected by the level of acidic excipient in the ASD formulation. The study followed the same design as designed above and all the dogs were pretreated with co-administration of anti-acid. All three palbociclib ASD formulations contain 1.5 M of HCl, but with 0, 50 mg and 100 mg tartaric acid (Formulation 15, Formulation 17 and Formulation 18). The results are shown in Table 19 and Table 20.

TABLE 19

|  |  | $C_{max}$ mg/mL | $AUC_t$ h * mg/mL | $AUC_{inf}$ h * mg/mL |
|---|---|---|---|---|
| Formulation 18 (T1) | Geo Mean | 795.3 | 18307.1 | 22025.5 |
|  | CV (%) | 20.7% | 18.1% | 21.0% |
| Formulation 17 (T2) | Geo Mean | 813.5 | 19592.8 | 23311.8 |
|  | CV (%) | 29.2% | 29.6% | 35.0% |
| Formulation 15 (T3) | Geo Mean | 774.6 | 16574.6 | 18986.6 |
|  | CV (%) | 27.9% | 39.2% | 43.9% |

TABLE 20

| Geometric Mean Ratio | $C_{max}$ | $AUC_t$ | $AUC_{inf}$ |
|---|---|---|---|
| T2/T1 | 102.3% | 107.0% | 105.8% |
| T3/T1 | 97.4% | 90.5% | 86.2% |

The tables show there is a notable but small (more or less than 10%) reduction of in vivo exposure for the ASD formulation with only 1.5 M HCl, but no tartaric acid (Formulation 15 or T3 in above tables), in comparison to the ASD formulation with additional tartaric acid (Formulation 17 or T2, Formulation 18 or T1). A smaller difference was observed between the ASD formulations with 50 mg and 100 mg of tartaric acid. Compared to the significant reduction of in vivo exposure of IBRANCE when co-administered with an anti-acid (shown in Table 16), this result shows that even a small amount of acid included in the palbociclib ASD formulation improves the in vivo exposure of palbociclib when co-administered with an anti-acid.

Comparison of Dog Pharmacokinetic Parameters of a Palbociclib Conventional Formulation and a Palbociclib ASD Formulation The in vivo exposure of a simple wet granulation formulation of palbociclib crystalline free base API with tartaric acid, the Reference 2 formulation described in Example 4, showed a reduction when co-administered with an anti-acid medication, in comparison to palbociclib ASD formulation with tartaric acid, as shown in Table 21 and Table 22. This dog study was performed in a crossover design the same as described above.

TABLE 21

|  |  | $C_{max}$ ng/mL | $AUC_t$ h * ng/mL | $AUC_{inf}$ h * ng/mL |
|---|---|---|---|---|
| Formulation 18 (T1) | Geo Mean | 802.5 | 15448.8 | 17501.5 |
|  | CV (%) | 11.2% | 10.0% | 10.3% |

TABLE 21-continued

|  |  | $C_{max}$ ng/mL | $AUC_t$ h * ng/mL | $AUC_{inf}$ h * ng/mL |
|---|---|---|---|---|
| Reference 2 (T2) | Geo Mean | 661.5 | 13086.0 | 14847.8 |
|  | CV (%) | 29.3% | 17.5% | 18.3% |

TABLE 22

| Geometric Mean Ratio | $C_{max}$ | $AUC_t$ | $AUC_{inf}$ |
|---|---|---|---|
| T2/T1 | 80.5% | 84.0% | 84.0% |

This result shows that the in vivo exposure of the palbociclib ASD formulation with acidic excipients outperforms the in vivo exposure of conventional formulations of API with acidic excipients.

Comparison of Dog Pharmacokinetic Parameters of Palbociclib ASD Formulations with and without Acidic Excipients The in vivo exposure of a simple palbociclib ASD formulation without any acidic excipient, as shown as Reference 1 describe in Example 4, showed a significant reduction when co-administered with an anti-acid medication, in comparison to palbociclib ASD formulation with tartaric acid, as shown in Table 23 and Table 24. This dog study was performed in a crossover design the same as described above.

TABLE 23

|  |  | $C_{max}$ ng/mL | $AUC_t$ h * ng/mL | $AUC_{inf}$ h * ng/mL |
|---|---|---|---|---|
| Formulation 18 (T1) | Geo Mean | 871.2 | 15613.3 | 19399.7 |
|  | CV(%) | 25.0% | 17.4% | 18.9% |
| Reference 1 (T2) | Geo Mean | 397.7 | 10587.8 | 13846.8 |
|  | CV(%) | 29.4% | 46.6% | 58.7% |

TABLE 24

| Geometric Mean Ratio | $C_{max}$ | $AUC_t$ | $AUC_{inf}$ |
|---|---|---|---|
| T2/T1 | 45.1% | 63.7% | 65.2% |

This result shows that the in vivo exposure of the palbociclib ASD formulation with acidic excipients outperforms the in vivo exposure of a simple ASD formulation API with a hydrophilic polymer only.

Comparison of Dog Pharmacokinetic Parameters of Scalable Palbociclib ASD Capsules Dog study results of two scalable palbociclib ASD capsule formulations are shown in Table 25 and Table 26. Both Formulation 19 and Formulation 20 have been prepared by lab scale equipment at kilo scales, representing scalable formulations.

A three-way crossover dog study was performed to assess and compare the pharmacokinetic parameters of these two capsule formulations following the dog study design described above. In this study, Formulation 19 and Formulation 20 were all given after overnight fasting. In addition, Formulation 20 was also co-administered with an anti-acid medication (ranitidine).

TABLE 25

|  |  | $C_{max}$ ng/mL | $AUC_t$ h * ng/mL | $AUC_{inf}$ h * ng/mL |
|---|---|---|---|---|
| Formulation 19 (T1) | Geo Mean | 1084.6 | 20533.8 | 22413.7 |
|  | CV(%) | 12.0% | 22.1% | 23.7% |
| Formulation 20 (T2) | Geo Mean | 1045.4 | 20104.7 | 21732.3 |
|  | CV(%) | 13.2% | 14.9% | 14.2% |
| Formulation 20-Antiacid (T3) | Geo Mean | 1082.7 | 19910.1 | 22036.1 |
|  | CV(%) | 15.4% | 23.3% | 25.9% |

TABLE 26

| Geometric Mean Ratio | $C_{max}$ | $AUC_t$ | $AUC_{inf}$ |
|---|---|---|---|
| T2/T1 | 96.4% | 97.9% | 97.0% |
| T3/T1 | 99.8% | 97.0% | 98.3% |
| T3/T2 | 99.0% | 99.0% | 101.4% |

The results in above two tables showed that the in vivo behaviors of these two formulations are the same. In addition, in vivo behavior of Formulation 20 is not affected by an anti-acid co-administration.

Example 6: Clinical Performance and Comparisons of Palbociclib ASD Formulations

Clinical Comparison of IBRANCE® Capsule and Palbociclib ASD Formulation Capsule

A capsule formulation containing 125 mg palbociclib that is analogous to Formulation 18 was tested in a clinical study to compare its in vivo performance in humans with IBRANCE® 125 mg capsule. Two crossover studies were performed to compare the pharmacokinetic parameters of both products in healthy volunteers, under the fed and fasted conditions. For the fasted condition, subjects were fasted overnight before drug administration. For the fed condition, a high-fat, high-calorie breakfast (approximately 800 to 1000 calories with 150, 250, and 500 to 600 calories from protein, carbohydrate, and fat, respectively) was finished before dosing. Blood samples were taken from each group of subjects at the following time points: 0 h (before test drug administration), and 1.0, 2.0, 3.0, 4.0, 5.0, 5.5, 6.0, 6.5, 7.0, 7.5, 8.0, 9.0, 10.0, 11.0, 12.0, 14.0, 16.0, 24, 48, 72, 96, 120 and 144 h after the drug administration. A total of 14 healthy volunteers completed the study. Palbociclib plasma concentrations were analyzed by an LC-MS/MS method. The non-compartment model of software WinNonlin® was used to calculate the pharmacokinetic parameters of each subject, $C_{max}$, $AUC_t$ and $AUC_{inf}$. The geometric least square means of the parameters were used for comparisons of the in vivo absorption of different products. The results from the fasted study were shown in Table 27 and the results from the fed study were shown in Table 28. The confidence interval of 90% of geometric least square mean ratio was calculated and used to compare the human in vivo exposure of both products. Typically, when a testing product is compared to a reference product, the 90% confidence interval of the parameters should be within 80.00% to 125.00% for two products to be considered as bioequivalent.

TABLE 27

|  |  | $C_{max}$ ng/mL | $AUC_t$ h * ng/mL | $AUC_{inf}$ h * ng/mL |
|---|---|---|---|---|
| IBRANCE (R) | Geometric Least Square Means | 50.2 | 1801.8 | 1843.5 |
| Palbociclib ASD (T) | Geometric Least Square Means | 66.4 | 2159.4 | 2200.0 |
| T/R | Geometric Least Square Mean Ratio | 132.18% | 119.85% | 119.34% |
| 90% Confidence Interval |  |  |  |  |
| T/R | Lower Limit | 103.82% | 103.40% | 103.10% |
|  | Upper Limit | 168.27% | 138.92% | 138.14% |

TABLE 28

|  |  | $C_{max}$ ng/mL | $AUC_t$ h * ng/mL | $AUC_{inf}$ h * ng/mL |
|---|---|---|---|---|
| IBRANCE (R) | Geometric Least Square Means | 75.1 | 2334.9 | 2377.0 |
| Palbociclib ASD (T) | Geometric Least Square Means | 77.2 | 2269.5 | 2393.0 |
| T/R | Geometric Least Square Mean Ratio | 102.8% | 97.2% | 100.7% |
| 90% Confidence Interval |  |  |  |  |
| T/R | Lower Limit | 96.62% | 88.13% | 94.35% |
|  | Upper Limit | 109.44% | 107.20% | 107.43% |

The results from above two tables show that the palbociclib ASD product developed with the current technology is bioequivalent to the IBRANCE® under the fed conditions and outperforms IBRANCE® under the fasting conditions.

The IBRANCE® capsule product label states that the pharmacokinetic parameters of $C_{max}$ and $AUC_{inf}$ of the product when administered under the overnight fasted conditions are about 38% and 21%, respectively, higher than the parameters of the product, when given with high-fat, high-calorie food. Due to this low in vivo exposure when administered fasted, the IBRANCE® capsule product is required to be taken with food.

The palbociclib ASD capsule product in this study showed higher $C_{max}$ and $AUC_{inf}$, about 32% and 19%, respectively, in comparison to the parameters of the IBRANCE® capsule product. Consequently, this result indicates a low or no food effect of the palbociclib ASD capsule product.

Clinical Drug-Drug Interaction Study of Palbociclib ASD Capsule Product

A palbociclib ASD capsule product, Formulation 19 (containing 125 mg palbociclib), was studied for its drug-drug interaction (DDI) with a proton pump inhibitor (PPI) in a clinical study.

This study is an open label, non-randomized, two-treatment, two-period, single-dose, drug-drug interaction study to evaluate the effects of an Omeprazole Delayed Release Capsules 40 mg, on the palbociclib ASD capsule product 125 mg in healthy, adult, human subjects under fasting conditions.

After an overnight fasting of at least 10.0 hours, a single oral dose of one capsule of the test product was administered with approximately 240 mL of room temperature water under fasting conditions on day-1 (Period 1 doing). A single oral dose of Omeprazole 40 mg Delayed Release Capsule was administered once before meals every morning with approximately 240 mL of room temperature water on day-8 to day-14. After an overnight fasting of at least 10.0 hours, a single oral dose of one capsule of the test product was administered with approximately 240 mL of room temperature water under fasting conditions on day-14 (Period 2 doing). Blood samples were taken from the subjects after each doing at the following time points: 0 h (before test drug administration), and 1.0, 2.0, 3.0, 4.0, 5.0, 5.5, 6.0, 6.5, 7.0, 7.5, 8.0, 8.5, 9.0, 10.0, 11.0, 12.0, 14.0, 16.0, 24, 48, 72, 96, 120 and 144 h after the drug administration. The rate and extent of absorption of the test product alone and after the administration of multiple dose Omeprazole Delayed Release Capsules 40 mg were calculated and compared using WinNonlin® software. The results are shown in Table 29.

TABLE 29

| | | $C_{max}$ ng/mL | $AUC_t$ h * ng/mL | $AUC_{inf}$ h * ng/mL |
|---|---|---|---|---|
| Formulation 19 (T1) | Geometric Least Square Means | 46.68 | 1164.9 | 1210.6 |
| Formulation 19 + PPI (T2) | Geometric Least Square Means | 43.57 | 1180.4 | 1228.0 |
| T2/T1 | Geometric Least Square Mean Ratio 90% Confidence Interval | 93.34% | 101.33% | 101.44% |
| T2/T1 | Lower Limit | 88.61% | 95.89% | 96.14% |
| | Upper Limit | 98.32% | 107.08% | 107.02% |

The above table shows that the rate and extent of absorption of the palbociclib ASD product, Formulation 19, are not affected by the proton pump inhibitor, a strong anti-acid medication. The product is considered as bioequivalent when administered along or co-administered with a PPI. However, in contrast, the IBRANCE capsule product label stated that coadministration of a single dose of IBRANCE with multiple doses of the PPI under fasted conditions decreased palbociclib $C_{max}$ and $AUC_{inf}$ by 80% and 62%, respectively, when compared to a single dose of IBRANCE administered alone.

Clinical Food Effect Study of Palbociclib ASD Capsule Product

Formulation 19, a palbociclib ASD capsule product containing 125 mg palbociclib, was studied for its food effect in a clinical study. This study is an open label, randomized, one-treatment, two-period, single-dose, oral bioavailability study of the test product in healthy, adult, human subjects under fasting and fed conditions.

For the subjects dosed under the fasting condition, after an overnight fast of at least 10.0 hours, a single oral dose of one capsule of the test product was administered with approximately 240 mL of room temperature water under fasting conditions. For the subjects dosed under the fed condition, after an overnight fast of at least 10.0 hours, and exactly 30 minutes after serving of a high-fat high-calorie breakfast, a single oral dose of one capsule of the test product was administered with approximately 240 mL of room temperature water under fed conditions. The rate and extent of absorption of a single dose of the test product under fasting and fed conditions were calculated and compared using WinNonlin® software. The results are shown in Table 30.

TABLE 30

| | | $C_{max}$ ng/mL | $AUC_t$ h * ng/mL | $AUC_{inf}$ h * ng/mL |
|---|---|---|---|---|
| Formulation 19 Fed (T1) | Geometric Least Square Means | 46.57 | 1125.3 | 1183.1 |
| Formulation 19 Fasted (T2) | Geometric Least Square Means | 39.81 | 979.4 | 1031.9 |
| T2/T1 | Geometric Least Square Mean Ratio 90% Confidence Interval | 85.48% | 87.03% | 87.22% |
| T2/T1 | Lower Limit | 80.30% | 83.04% | 83.36% |
| | Upper Limit | 90.99% | 91.21% | 91.26% |

The above table shows that the rate and extent of absorption of the palbociclib ASD product, Formulation 19, are minimally affected by food. The product is considered as bioequivalent when administered with or without high-fat, high-calorie food. However, in contrast, the IBRANCE® capsule product label states that compared to IBRANCE given under overnight fasted conditions, the pharmacokinetic parameters of $C_{max}$ and $AUC_{inf}$ of the product increased by about 38% and 21%, respectively, when given with high-fat, high-calorie food.

Example 7: Clinical Performance and Comparisons of Palbociclib ASD Formulation 20

Clinical Comparison of IBRANCE® Capsule and Palbociclib ASD Formulation Capsule

A capsule formulation containing 125 mg palbociclib that is analogous to Formulation 20 is tested in a clinical study to compare the in vivo performance in humans with IBRANCE® 125 mg capsule. Two crossover studies are performed to compare the pharmacokinetic parameters of both products in healthy volunteers, under the fed and fasted conditions. For the fasted condition, subjects are fasted overnight before drug administration. For the fed condition, a high-fat, high-calorie breakfast (approximately 800 to 1000 calories with 150, 250, and 500 to 600 calories from protein, carbohydrate, and fat, respectively) is finished before dosing. Blood samples are taken from each group of subjects at the following time points: 0 h (before test drug administration), and 1.0, 2.0, 3.0, 4.0, 5.0, 5.5, 6.0, 6.5, 7.0, 7.5, 8.0, 9.0, 10.0, 11.0, 12.0, 14.0, 16.0, 24, 48, 72, 96, 120 and 144 h after the drug administration. Palbociclib plasma concentrations are analyzed by an LC-MS/MS method. The non-compartment model of software WinNonlin® is used to calculate the pharmacokinetic parameters of each subject, $C_{max}$, $AUC_t$ and $AUC_{inf}$. The geometric least square means of the parameters is used for comparisons of the in vivo absorption of different products.

Clinical Drug-Drug Interaction Study of Palbociclib ASD Capsule Product

A palbociclib ASD capsule product, Formulation 20 (containing 125 mg palbociclib), is studied for its drug-drug interaction (DDI) with a proton pump inhibitor (PPI) in a clinical study. This study is an open label, non-randomized, two-treatment, two-period, single-dose, drug-drug interaction study to evaluate the effects of an Omeprazole Delayed Release Capsules 40 mg, on the palbociclib ASD capsule product 125 mg in healthy, adult, human subjects under fasting conditions.

After an overnight fasting of at least 10.0 hours, a single oral dose of one capsule of the test product is administered with approximately 240 mL of room temperature water under fasting conditions on day-1 (Period 1 doing). A single oral dose of Omeprazole 40 mg Delayed Release Capsule is administered once before meals every morning with approximately 240 mL of room temperature water on day-8 to day-14. After an overnight fasting of at least 10.0 hours, a single oral dose of one capsule of the test product is administered with approximately 240 mL of room temperature water under fasting conditions on day-14 (Period 2 doing). Blood samples are taken from the subjects after each dosing at the following time points: 0 h (before test drug administration), and 1.0, 2.0, 3.0, 4.0, 5.0, 5.5, 6.0, 6.5, 7.0, 7.5, 8.0, 8.5, 9.0, 10.0, 11.0, 12.0, 14.0, 16.0, 24, 48, 72, 96, 120 and 144 h after the drug administration. The rate and extent of absorption of the test product alone and after the administration of multiple dose Omeprazole Delayed Release Capsules 40 mg is calculated and compared using WinNonlin® software.

Clinical Food Effect Study of Palbociclib ASD Capsule Product

Formulation 20, a palbociclib ASD capsule product containing 125 mg palbociclib, is studied for its food effect in a clinical study. This study is an open label, randomized, one-treatment, two-period, single-dose, oral bioavailability study of the test product in healthy, adult, human subjects under fasting and fed conditions.

For the subjects dosed under the fasting condition, after an overnight fast of at least 10.0 hours, a single oral dose of one capsule of the test product is administered with approximately 240 mL of room temperature water under fasting conditions. For the subjects dosed under the fed condition, after an overnight fast of at least 10.0 hours, and exactly 30 minutes after serving of a high-fat high-calorie breakfast, a single oral dose of one capsule of the test product is administered with approximately 240 mL of room temperature water under fed conditions. The rate and extent of absorption of a single dose of the test product under fasting and fed conditions is calculated and compared using WinNonlin® software.

Example 8: The Spray Drying Processes of Neratinib Maleate Amorphous Solid Dispersions The Spray Drying Processes Using a Bench Top Spray Dryer The active pharmaceutical ingredient (neratinib maleate), acid pharmaceutical excipient(s), and polymer were dissolved in a solvent or solvent mixture at a room temperature to form a clear solution. A bench top spray dryer (Brand: LabPlant; Model #: SD-06AG, Manufacturer: Lab-Plant UK. Ltd.) was preheated until a steady state was achieved. The solution was then introduced into the spray dryer via flash atomization at a feed rate of about 3-10 rpm, at an inlet drying gas temperature of about 50-80° C. depending on the solvent used, and an outlet temperature of about 35-60° C., and a pressure of about 2-3 bar. After collection, the particles were placed into a vacuum tray dryer operated at 40° C.

Example 9: Formulation Compositions of Neratinib Maleate Amorphous Solid Dispersions (ASD)

Compositions of Neratinib Maleate Amorphous Solid Dispersions with an Organic Acid and a Polymer The following tables, Table 31 and Table 32, list the compositions of some of the amorphous solid dispersions that have been prepared by spray drying of neratinib maleate, an organic acid and a polymer solubilized in mixture solvent of DCM and methanol, per the preparation process shown in Example 8.

TABLE 31

|  | Formulation 22 | | | Formulation 23 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Neratinib maleate - 48.31 mg | 44.6% | 3.00 | Neratinib maleate - 48.31 mg | 37.6% | 2.5 |
| Organic Acid | Maleic Acid - 20 mg[1] | 18.5% | 1.24 | Maleic Acid - 40 mg[2] | 31.2% | 2.07 |
| Polymer | Copovidone - 40 mg | 36.9% | 2.48 | PVP K30 - 40 mg | 31.2% | 2.07 |
| Total | 108.31 mg | 100% | 6.72 | 128.31 mg | 100% | 6.64 |
| Solvent | Removed after spray drying | | DCM - 47.57 g Methanol - 12.19 g | Removed after spray drying | | DCM - 47.57 g Methanol - 12.19 g |

[1]The weight ratio of neratinib free base to maleic acid is 2:1, and the molar ratio of neratinib free base to maleic acid is 1:2.4
[2]The weight ratio of neratinib free base and maleic acid is 1:1, and the molar ratio of neratinib free base to maleic acid is 1:4.8

TABLE 32

| | Formulation 24 | | |
| --- | --- | --- | --- |
|  | Amount in one dose (mg) | % in formulation | Amount during preparation (g) |
| API | Neratinib maleate - 48.31 mg | 37.6% | 2.5 |
| Organic Acid | Malic Acid - 40 mg[1] | 31.2% | 2.07 |
| Polymer | Copovidone - 40 mg | 31.2% | 2.07 |
| Total | 128.31 mg | 100% | 6.64 |
| Solvent | Removed after spray drying | | DCM - 47.57 g Methanol - 12.19 g |

[1]The weight ratio of neratinib free base and malic acid is 1:1, and the molar ratio of neratinib free base to malic acid is 1:4.2

Figure 17:
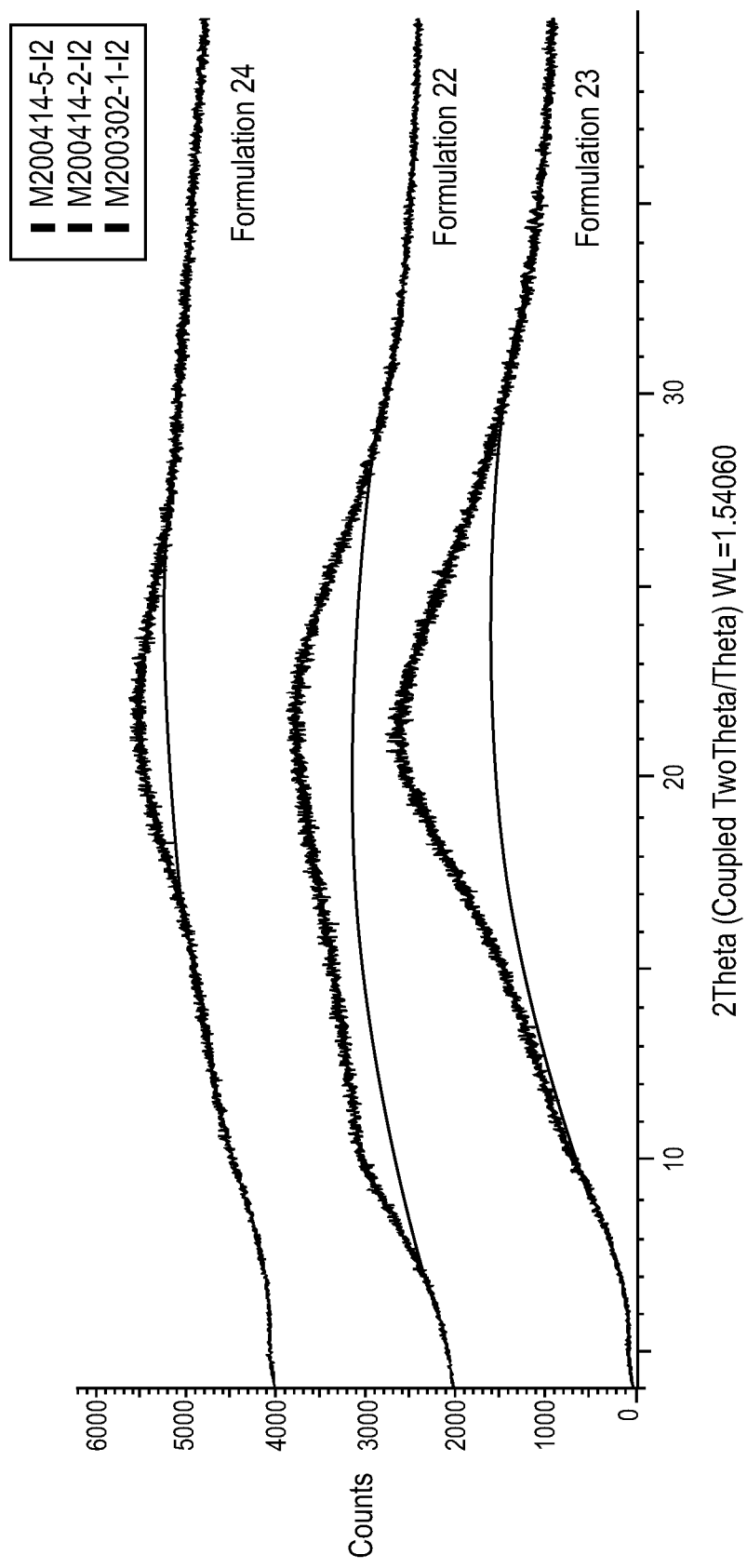
FIG. 17 shows the XRPD of neratinib maleate ASD Formulations 22, 23, and 24.

The solid content, the percentage of the total amount of solutes in the spray drying solution, of Formulation 22 to 24 was 10.0%. The amorphous solid dispersion powders of these three formulations were shown to be amorphous in FIG. 17 by XRPD.

Compositions of Neratinib Maleate Amorphous Solid Dispersions with a Strong Acid, an Organic Acid and a Polymer The following table list the compositions of the amorphous solid dispersions that have been prepared by spray drying. In this example, methanesulfonic acid was used as a first acid, and a second acid and a polymer were further dissolved at room temperature to achieve a complete dissolution. The solutions were further spray dried in a bench top spray dryer according to the spray drying process described in Example 8.

TABLE 33

Formulation 25

|  | Amount in one dose (mg) | % in formulation | Amount during preparation (g) |
|---|---|---|---|
| API | Neratinib maleate - 48.31 mg | 41.9 | 3.0 |
| First Acid | Methanesulfonic Acid - 6.9 mg[1] | 6.1 | 0.44 |
| Second Acid | Maleic Acid - 20 mg[2] | 17.3 | 1.24 |
| Polymer | Copovidone - 40 mg | 34.7 | 2.48 |
| Total | 115.2 mg | 100% | 7.16 |
| Solvent | Removed after spray drying | | Water: 21.09 Methanol: 38.98 |

[1]The molar ratio of neratinib free base and methanesulfonic acid is 1:1.
[2]The weight ratio of neratinib free base and maleic acid is 2:1, and the molar ratio of neratinib free base and maleic acid is 1:2.4.

Figure 18:
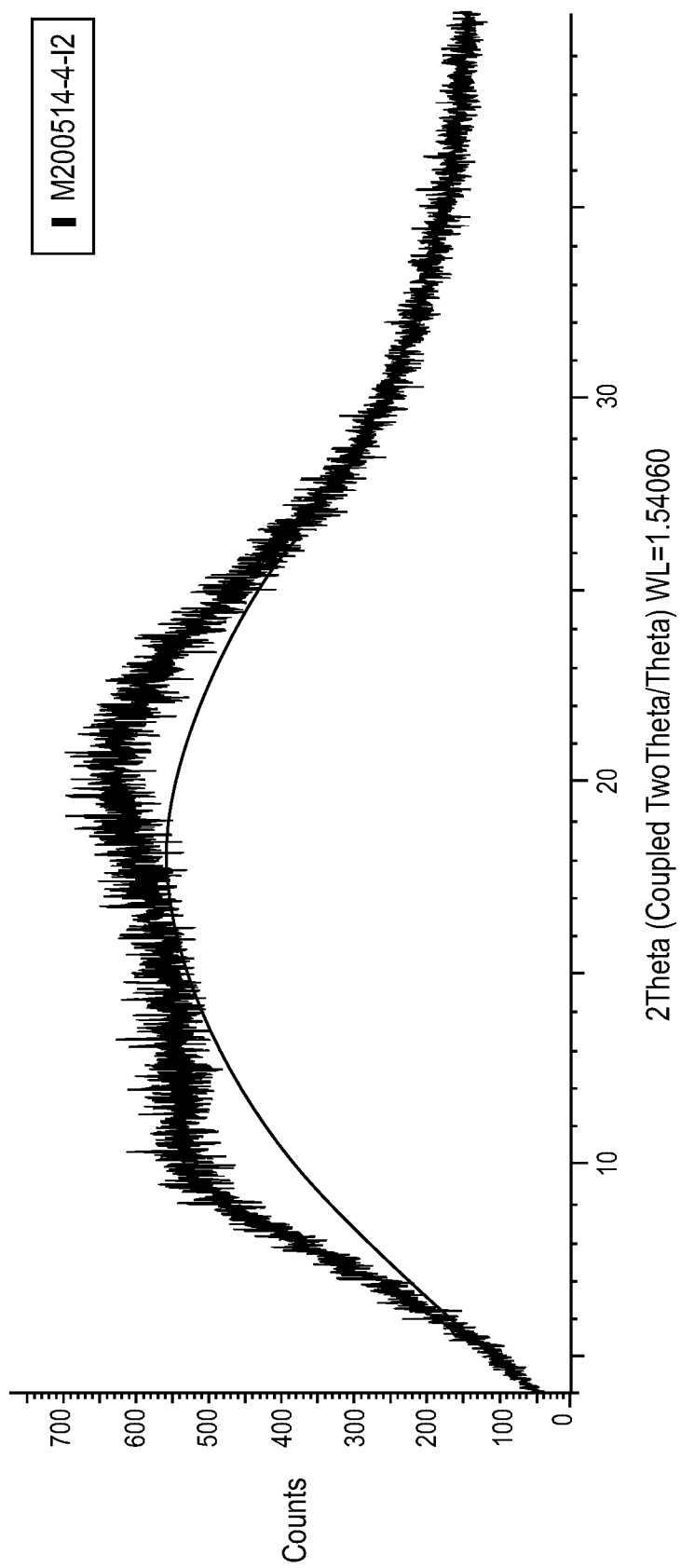
FIG. 18 shows the XRPD of neratinib maleate ASD Formulations 25.

The amorphous solid dispersion powders of the formulation in the above table was shown to be amorphous in FIG. 18 by XRPD.

Compositions of Neratinib Maleate Amorphous Solid Dispersions with an Organic Acid, a Surfactant and a Polymer The following table list the compositions of the amorphous solid dispersions that have been prepared by spray drying. In this example, an organic acid, a surfactant and a polymer were dissolved at room temperature to form a solution. The solutions were further spray dried in a bench top spray dryer according to the spray drying process described in Example 8.

TABLE 34

Formulation 26

|  | Amount in one dose (mg) | % in formulation | Amount during preparation (g) |
|---|---|---|---|
| API | Neratinib maleate - 48.31 mg | 37.6 | 3.00 |
| Organic Acid | Maleic Acid - 20 mg[1] | 15.6 | 1.24 |
| Polymer | PVP K30 - 40 mg | 31.1 | 2.48 |
| Surfactant | Lecithin - 20 mg | 15.7 | 1.25 |
| Total | 148.4 mg | 100% | 7.97 |
| Solvent | Removed after spray drying | | DCM - 57.31 g Methanol - 14.63 g |

[1]The weight ratio of neratinib free base and maleic acid is 2:1, and the molar ratio of neratinib free base and maleic acid is 1:2.4.

Figure 19:
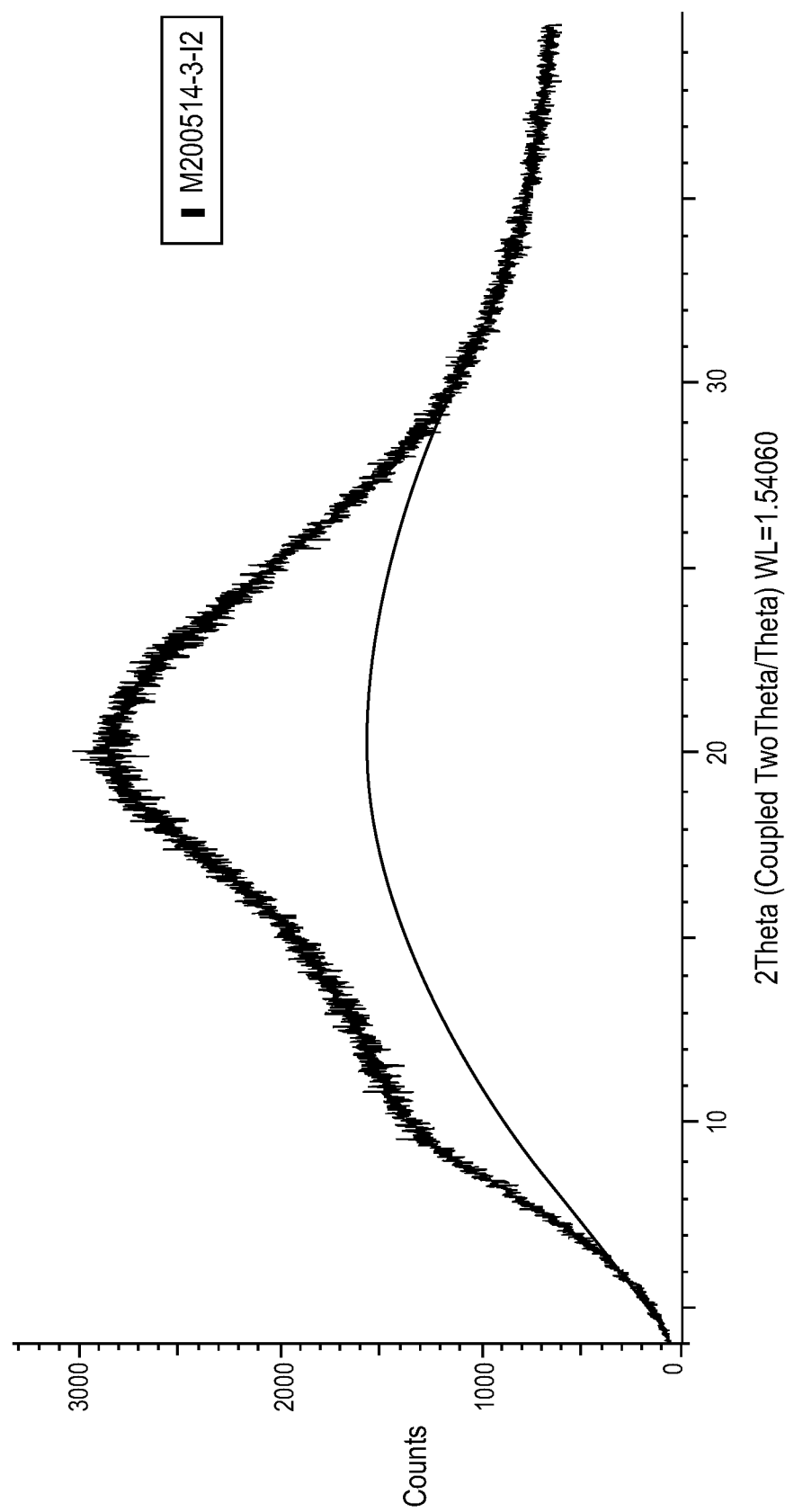
FIG. 19 shows the XRPD of neratinib maleate ASD Formulations 26.

The amorphous solid dispersion powders of the formulation in Table 34 was shown to be amorphous in FIG. 19 by XRPD.

Example 10: Tablet Formulations of Neratinib Maleate Amorphous Solid Dispersions Some of the amorphous solid dispersions of neratinib maleate shown in Examples 9 were further processed into tablet formulations.

The formulations in Table 35 were prepared by mixing the relative amounts of amorphous solid dispersions with other excipients for tablet pressing. These tablets formulations were used to assess their in vitro dissolution.

TABLE 35

|  | Formulation 27 | Formulation 28 |
|---|---|---|
| Dry granulation materials | Formulation 22 ASD - 108.4 mg Crospovidone - 25.6 mg MCC PH101 - 86.8 mg Mannitol - 96 mg Silica - 1.6 mg MgSt - 1.6 mg | Formulation 25 ASD - 115.3 mg Crospovidone - 25.6 mg MCC PH101 - 66.8 mg Mannitol - 96 mg Silica - 1.6 mg MgSt - 1.6 mg |
| Total weight | 320 mg | 320 mg |

Example 11: In Vitro Performance and Comparisons of Neratinib Maleate ASD Formulations Kinetic Solubility Profiles of Neratinib Maleate ASD Powders The kinetic solubility profiles of different compositions of neratinib maleate ASD powders were assessed. The kinetic solubility profiles were performed by adding neratinib maleate ASD powders (containing 240 mg of neratinib free base) into 250 ml of pH 4.0 phthalic acid buffer solution in a dissolution bath at 37° C. and stirred at 100 rpm. The concentrations of neratinib maleate in the solution at different time points were determined by a HPLC method.

In this study, the kinetic solubility profiles ASD formulations of neratinib maleate with acidic excipients and polymer were compared with a reference neratinib maleate. Formulation A and Formulation B are the ASD powder prepared with neratinib maleate, maleic acid and polymer at different ratio. The weight ratio of neratinib free base to maleic acid to polymer is 3:1:2 in Formulation A, and 1:1:1 in Formulation B.

Figure 20:
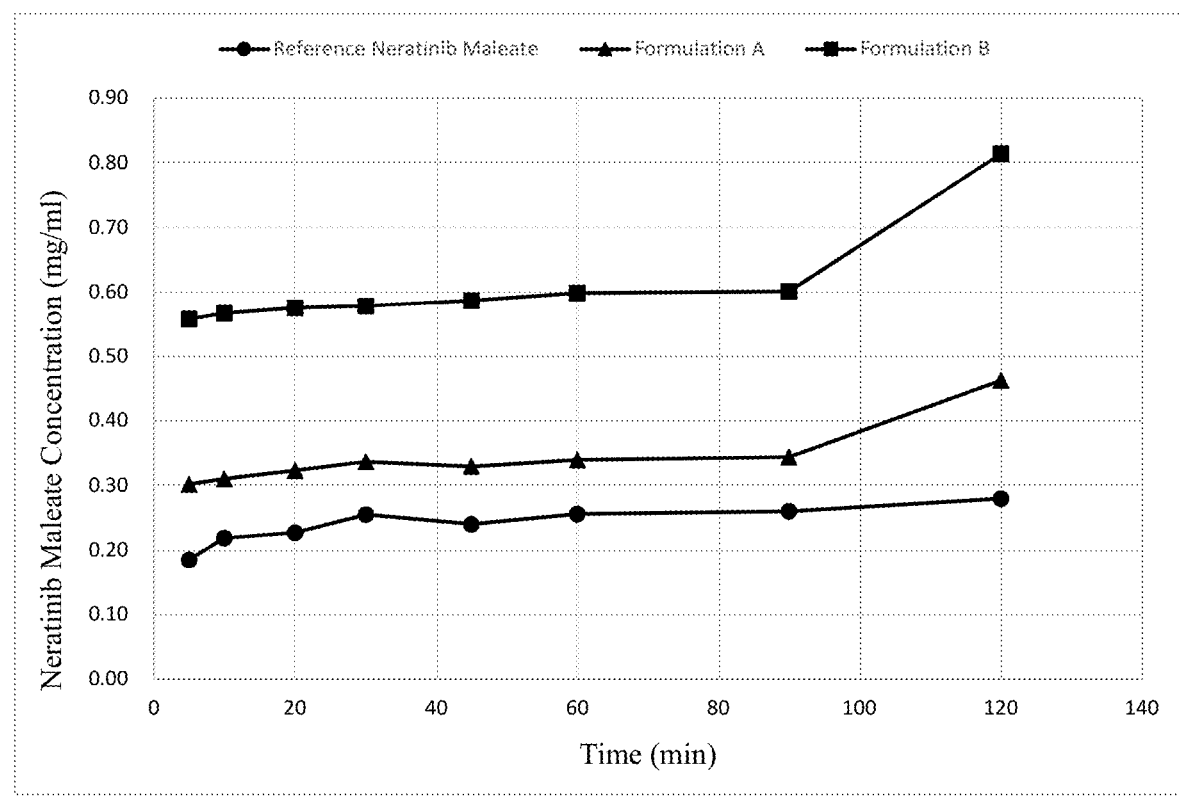
FIG. 20 shows the kinetic solubility of neratinib maleate ASD powders.

The comparison of the kinetic solubility profiles is shown in FIG. 20. The solubility of neratinib maleate crystalline free base is less than 0.3 mg/mL. The kinetic solubility of the ASD is improved, in comparison to the crystalline neratinib maleate.

In Vitro Dissolutions of Neratinib Maleate Tablet Formulations

Several neratinib maleate formulations were assessed for their in vitro dissolution profiles. In this study, Formulation 27 and 28 were used to represent the amorphous solid dispersion of neratinib maleate with acidic excipients. The in vitro dissolution profile of these formulation was compared to the following reference formulations.

Reference 1 is the tablet formulation of a conventional formulation of neratinib maleate crystalline API by wet granulation. This formulation was prepared to represent a simple reference formulation of neratinib maleate.

Reference 2 is a conventional wet granulation formulation of neratinib maleate crystalline API with an acidic excipient. Crystalline neratinib maleate API and maleate acid (the weight ratio of API as free base and the acid is 40:20), in combination with other conventional excipients, were wet granulated and compressed for tablets. This formulation was prepared to represent a simple conventional formulation of neratinib maleate with simple mixture of an acidic excipient.

The dissolutions were performed in 500 ml of pH 4.0 phthalic acid buffer at 37° C., with a paddle method at 50 rpm.

Figure 21:
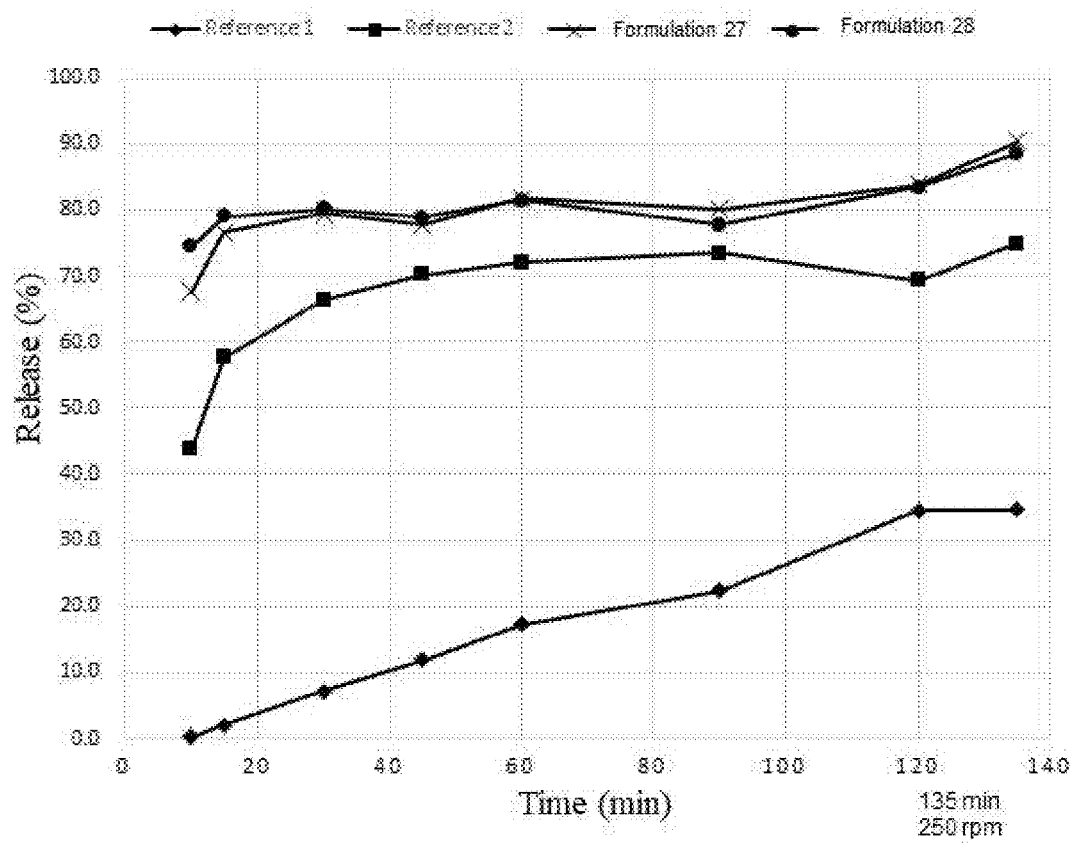
FIG. 21 shows the dissolution profiles of different neratinib maleate formulations.

As shown in FIG. 21, Formulation 27 and Formulation 28, the capsule formulation of neratinib maleate ASD with acidic excipients, showed a significantly higher dissolution, in comparison to the profiles of two reference formulations. The dissolution profile of Reference 2 is also improved, demonstrating the benefit of acidic excipients. The results show the combined benefit of combining an acidic excipient, API and a hydrophilic polymer to form an amorphous solid dispersion.

Example 12: Preparation of an Amorphous Solid Dispersion of Erlotinib 3.20 g of methanol was added to a container, followed by 7.95 g of dichloromethane to form the solvent (removed after spray drying). This was mixed well, and 100 mg of erlotinib hydrochloride was added, followed by 100 mg of copovidone. The solution, the formulation of which is shown in Table 36, was prepared and maintained at room temperature, and it was mixed continuously until completely dissolved. The solution was then spray dried. The spray drier was preheated at an inlet drying gas temperature of 75° C. Once the spray dryer reached steady-state, the pre-mixed solution was introduced into the spray dryer at a pressure of 2.0-2.5 bar and a feed rate of 10 rpm (20 g/min). The particles were collected at the outlet of the spray dryer, which was set to a temperature of 44° C. The XRPD profile of this spray dried dispersion showed that it is amorphous, with no detectable crystallinity.

TABLE 36

|  | Material | Targeted weight (g) | % in SDD | % in solution |
|---|---|---|---|---|
| Solvent (removed after dry spraying) | Methanol | 3.20 | / | 28.19 |
|  | Dichloromethane | 7.95 | / | 70.05 |
| Materials in SDD | Erlotinib hydrochloride | 0.100 | 50.00 | 0.88 |
|  | Copovidone | 0.100 | 50.00 | 0.88 |
| Total |  | 11.35 | 100 | 100 |

Example 13: Preparation of an Amorphous Solid Dispersion of Erlotinib 3.20 g of methanol was added to a container, followed by 7.95 g of dichloromethane to form the solvent (removed after spray drying). This was mixed well, and 100 mg of erlotinib hydrochloride was added, followed by 100 mg of tartaric acid, then 100 mg of PVP-VA64. The solution, the formulation of which is shown in Table 37, was prepared and maintained at room temperature, and it was mixed continuously until completely dissolved. The solution was then spray dried. The spray drier was preheated at an inlet drying gas temperature of 73° C. Once the spray dryer reached steady-state, the pre-mixed solution was introduced into the spray dryer at a pressure of 2.0-2.5 bar and a feed rate of 10 rpm (20 g/min). The particles were collected at the outlet of the spray dryer, which was set to a temperature of 43° C. The XRPD profile of this spray dried dispersion showed that it is amorphous, with no detectable crystallinity.

TABLE 37

|  | Material | Targeted weight (g) | % in SDD | % in solution |
|---|---|---|---|---|
| Solvent (removed after dry spraying) | Methanol | 3.20 | / | 27.95 |
|  | Dichloromethane | 7.95 | / | 69.44 |

TABLE 37-continued

|  | Material | Targeted weight (g) | % in SDD | % in solution |
|---|---|---|---|---|
| Materials in SDD | Erlotinib hydrochloride | 0.100 | 33.33 | 0.87 |
|  | Tartaric acid | 0.100 | 33.33 | 0.87 |
|  | Copovidone | 0.100 | 33.33 | 0.87 |
| Total |  | 11.45 | 100 | 100 |

Example 14: Preparation of an Amorphous Solid Dispersion of Gefitinib 7.50 g of methanol was added to a container, followed by 2.5 g of water to form the solvent (removed after spray drying). This was mixed well, and 100 mg of gefitiib was added, followed by 100 mg of tartaric acid, then 100 mg of PVP-VA64. The solution, the formulation of which is shown in Table 38, was prepared and maintained at room temperature, and it was mixed continuously until completely dissolved. The solution was then spray dried. The spray drier was preheated at an inlet drying gas temperature of 148° C. Once the spray dryer reached steady-state, the pre-mixed solution was introduced into the spray dryer at a pressure of 2.0-2.5 bar and a feed rate of 10 rpm (20 g/min). The particles were collected at the outlet of the spray dryer, which was set to a temperature of 73° C. The XRPD profile of this spray dried dispersion showed that it is amorphous, with no detectable crystallinity.

TABLE 38

|  | Material | Targeted weight (g) | % in SDD | % in solution |
|---|---|---|---|---|
| Solvent (removed after dry spraying) | Methanol | 7.50 | / | 72.82 |
|  | Water | 2.50 g | / | 24.27 |
| Materials in SDD | Gefitinib | 0.100 | 33.33 | 0.97 |
|  | Tartaric acid | 0.100 | 33.33 | 0.97 |
|  | Copovidone | 0.100 | 33.33 | 0.97 |
| Total |  | 10.30 | 100 | 100 |

What is claimed is:

1. An amorphous solid dispersion, wherein the amorphous solid dispersion comprises the following in an amorphous state:
    a) a first acid, wherein the first acid is an organic acid that has a pKa of at most 2;
    b) a second acid, wherein the second acid is an organic acid that has a pKa greater than 2;
    c) a hydrophilic high-molecular weight material; and
    d) palbociclib, a salt of palbociclib, or any combination thereof, wherein the salt of palbociclib comprises the palbociclib and the first acid,
        wherein the molar ratio of the first acid to palbociclib is from 0.5:1 to 5:1, and
        wherein the weight ratio of the second acid to palbociclib is from 0.1:1 to 10:1.

2. The amorphous solid dispersion of claim 1, wherein palbociclib is at least partially protonated.

3. The amorphous solid dispersion of claim 1, wherein the salt of palbociclib is a monovalent palbociclib salt or a divalent palbociclib salt.

4. The amorphous solid dispersion of claim 1, wherein the salt of palbociclib comprises:
   a) one or more cations comprising monoprotonated palbociclib, diprotonated palbociclib, or any combination thereof, and
   b) one or more anions comprising a conjugate base of the first acid.

5. The amorphous solid dispersion of claim 1, wherein the first acid is oxalic acid, maleic acid, trichloroacetic acid, dichloroacetic acid, trifluoroacetic acid, an aliphatic sulfonic acid, or an aromatic sulfonic acid.

6. The amorphous solid dispersion of claim 1, wherein the first acid is methanesulfonic acid, methanedisulfonic acid, triflic acid, ethanesulfonic acid, ethanedisulfonic acid, isethionic acid, 2-mercapto-1-ethansulfonic acid, propanesulfonic acid, butanesulfonic acid, benzylsulfonic acid, benzenesulfonic acid, tolylsulfonic acid, or naphthalenesulfonic acid.

7. The amorphous solid dispersion of claim 1, wherein the second acid has a pKa of 2 to 6.

8. The amorphous solid dispersion of claim 1, wherein the second acid is tartaric acid, fumaric acid, succinic acid, citric acid, lactic acid, malic acid, or acetic acid.

9. The amorphous solid dispersion of claim 1, wherein the molar ratio of the first acid to palbociclib is from 0.5:1 to 3:1.

10. The amorphous solid dispersion of claim 1, wherein the hydrophilic high-molecular weight material comprises vinylpyrrolidone-vinyl acetate copolymer (copovidone), polyvinylpyrrolidone (PVP or povidone), polyvinyl alcohol (PVA), polysaccharide, hydroxypropyl methylcellulose (HPMC or hypromellose), hydroxyethyl cellulose (HEC), hydroxypropyl cellulose (HPC), polyethylene oxide, hydroxypropyl-β-cyclodextrin (HP-β-CD), sulfobutylether-β-cyclodextrin, hydroxypropyl methylcellulose acetate succinate (HPMCAS), polyethylene glycol (PEG), polyvinyl caprolactam-polyvinyl acetate-polyethylene glycol graft copolymer (PVAc-PVCap-PEG), or a combination thereof.

11. The amorphous solid dispersion of claim 10, wherein the hydrophilic high-molecular weight material is PVP, copovidone, HPMC, or a combination thereof.

12. A pharmaceutical composition, wherein the pharmaceutical composition comprises
   1) an amorphous solid dispersion comprising the following in an amorphous state:
      a) a first acid, wherein the first acid is an organic acid that has a pKa of at most 2;
      b) a second acid, wherein the second acid is an organic acid that has a pKa greater than 2;
      c) a hydrophilic high-molecular weight material; and
      d) palbociclib, a salt of palbociclib, or any combination thereof, wherein the salt of palbociclib comprises the palbociclib and the first acid,
         wherein the molar ratio of the first acid to palbociclib is from 0.5:1 to 5:1, and
         wherein the weight ratio of the second acid to palbociclib is from 0.1:1 to 10:1; and
   2) one or more pharmaceutically acceptable carriers or excipients.

13. The pharmaceutical composition of claim 12, wherein the one or more pharmaceutically acceptable carriers or excipients comprise a filler, a binder, a disintegrating agent, a lubricant, an adsorbent, an acid, or a combination thereof.

14. The pharmaceutical composition of claim 13, wherein the acid is an exterior acid selected from oxalic acid, maleic acid, trichloroacetic acid, dichloroacetic acid, trifluoroacetic acid, tartaric acid, fumaric acid, succinic acid, citric acid, lactic acid, malic acid, and acetic acid an aliphatic sulfonic acid, or an aromatic sulfonic acid.

15. The pharmaceutical composition of claim 13, wherein the one or more pharmaceutically acceptable carriers or excipients comprise microcrystalline cellulose, lactose, crospovidone, magnesium stearate, silicon dioxide, an organic acid, or a combination thereof.

16. A method of treating breast cancer, comprising administering to a subject in need thereof the pharmaceutical composition of claim 12.

17. The method of claim 16, wherein the cancer is metastatic breast cancer.

18. The method of claim 17, wherein the breast cancer is hormone receptor (HR)-positive breast cancer.

19. The method of claim 17, wherein the breast cancer is human epidermal growth factor receptor 2 (HER2)-negative advanced breast cancer.

20. The amorphous solid dispersion of claim 1, wherein the first acid is methanesulfonic acid, and wherein the second acid is tartaric acid.

21. The pharmaceutical composition of claim 12, wherein the first acid is methanesulfonic acid, and wherein the second acid is tartaric acid.

* * * * *